United States Patent
Wang et al.

(10) Patent No.: US 10,793,913 B2
(45) Date of Patent: Oct. 6, 2020

(54) METHODS AND COMPOSITIONS FOR TREATMENT OF BREAST CANCER

(71) Applicant: City of Hope, Duarte, CA (US)

(72) Inventors: Shizhen Emily Wang, Glendora, CA (US); Xiwei Wu, Diamond Bar, CA (US)

(73) Assignee: City of Hope, Duarte, CA (US)

( * ) Notice: Subject to any disclaimer, the term of this patent is extended or adjusted under 35 U.S.C. 154(b) by 406 days.

(21) Appl. No.: 14/203,173

(22) Filed: Mar. 10, 2014

(65) Prior Publication Data

US 2014/0274769 A1    Sep. 18, 2014

Related U.S. Application Data

(60) Provisional application No. 61/775,243, filed on Mar. 8, 2013.

(51) Int. Cl.
   *C12Q 1/68*   (2018.01)
   *C12Q 1/6886* (2018.01)

(52) U.S. Cl.
   CPC ..... *C12Q 1/6886* (2013.01); *C12Q 2600/158* (2013.01); *C12Q 2600/178* (2013.01)

(58) Field of Classification Search
   None
   See application file for complete search history.

(56) References Cited

U.S. PATENT DOCUMENTS

| | | | | |
|---|---|---|---|---|
| 8,658,370 B2 * | 2/2014 | Croce | ............ | C12Q 1/6886 435/6.1 |
| 2007/0299030 A1 * | 12/2007 | Dmitrovsky | .......... | C12N 15/111 514/44 A |
| 2011/0003704 A1 * | 1/2011 | Skog | .............. | C12Q 1/6806 506/9 |
| 2011/0117565 A1 * | 5/2011 | Zhang | ............ | C12Q 1/6886 435/6.12 |
| 2011/0293653 A1 * | 12/2011 | Szabo | ............ | A61K 31/713 424/195.16 |
| 2013/0130927 A1 * | 5/2013 | Heneghan | ........... | C12Q 1/6886 506/9 |

OTHER PUBLICATIONS

Hui et al., Robust global micro-RNA profiling with formalin-fixed paraffin-embedded breast cancer tissues, Laboratory Investigation (2009) 89, 597-606.*
Mo et al., Cell-free Circulating miRNA Biomarkers in Cancer, Journal of Cancer 2012, 3:432-448.*
Mascellani et al., Using miRNA expression data for the study of human cancer, Minerva Biotec 2008;20:23-30.*
Kramer, Stem-Loop RT-qPCR for miRNAS, Curr Protoc Mol Biol. Jul. 2011 ; Chapter: Unit15.10.*
Applied Biosystems, TaqMan® Human MicroRNA Arrays, Printed in the USA. Jun. 2008 Publication 127MI68-01, Downloaded by Examiner on Jun. 22, 2016 from https://tools.thermofisher.com/content/sfs/manuals/cms_054742.pdf.*
Xu et al., Circulating MicroRNAs, miR-21, miR-122, and miR-223, in Patients With Hepatocellular Carcinoma or Chronic Hepatitis, Molecular Carcinogenesis 50:136-142 (2011).*
Heid et al., Real Time Quantitative PCR, Genome Res. 1996. 6: 986-994.*
Chen et al., Cell Research (2008) 18:997-1006.*
Asaga et al., "Direct serum assay for microRNA-21 concentrations in early and advanced breast cancer," Clin Chem, 57:84-91 (2011).
Blenkiron et al., "MicroRNA expression profiling of human breast cancer identifies new markers of tumor subtype," Genome Biology, 8:R214, 16 pages (2007).
Boutz et al., "Two-tiered approach identifies a network of cancer and liver disease-related genes regulated by miR-122," J Biol Chem 286:18066-18078 (2011).
Fassan et al., "MicroRNA expression profiling of male breast cancer," Breast Cancer Res, 11:R58, 10 pages (2009).
Fu et al., "miRNA Biomarkers in Breast Cancer Detection and Management," J Cancer 2:116-122 (2011).
Girard et al., "miR-122, a paradigm for the role of microRNAs in the liver," J Hepatol, 48:648-656 (2008).
Heneghan et al., "Circulating microRNAs as novel minimally invasive biomarkers for breast cancer," Ann Surg. 251(3):499-505 (2010).
Iorio et al., "MicroRNA gene expression deregulation in human breast cancer," Cancer Res. 65:7065-7070 (2005).
Jung et al., "Plasma miR-210 levels correlate with sensitivity to trastuzumab and tumor presence in breast cancer patients," Cancer, 118(10):2603-2614 (2012).
Kutay et al., "Downregulation of miR-122 in the rodent and human hepatocellular carcinomas," J Cell Biochem, Oct. 15, 2006; 99(3):671-678 (2006).
Lodes et al., "Detection of cancer with serum miRNAs on an oligonucleotide microarray," PLoS One, 4(7):e6229, 12 pages (2009).
Maillot et al., "Widespread estrogen-dependent repression of micromas involved in breast tumor cell growth," Cancer Res, 69:8332-8340 (2009).
Mattie et al., "Optimized high-throughput microRNA expression profiling provides novel biomarker assessment of clinical prostate and breast cancer biopsies," Mol Cancer, 5:24, 14 pages (2006).
Moore et al., "The role of microRNAs in cholesterol efflux and hepatic lipid metabolism," Annu Rev Nutr 31:49-63 (2011).

(Continued)

*Primary Examiner* — Mindy G Brown
(74) *Attorney, Agent, or Firm* — Mintz, Levin, Cohn, Ferris, Glovsky and Popeo, P.C.

(57) ABSTRACT

Provided are methods of treating breast cancer in a subject in need thereof comprising administering to the subject an effective amount of an inhibitor of miR-105 or an inhibitor of miR-122 are provided. Also provided herein are methods of determining a level of miR-105 or a level of miR-122 in a subject that has or is at risk for developing breast cancer. The method includes obtaining a biological sample from the subject and determining a level of miR-105 or a level of miR-122 or a combination thereof in the biological sample, wherein a higher level of miR-105 or miR-122 as compared to a control indicates that the subject has or is at risk of developing breast cancer.

33 Claims, 39 Drawing Sheets
Specification includes a Sequence Listing.

(56) References Cited

OTHER PUBLICATIONS

Pigati et al.,"Selective release of microRNA species from normal and malignant mammary epithelial cells," PLoS One, 5:e13515, 13 pages (2010).
Roth et al., "Circulating microRNAs as blood-based markers for patients with primary and metastatic breast cancer," Breast Cancer Res. 12:R90, 8 pages (2010).
Wu et al., "De novo sequencing of circulating miRNAs identifies novel markers predicting clinical outcome of locally advanced breast cancer," J Transl Med 10:42, 10 pages (2012).
Xu et al., "Circulating microRNAs, miR-21, miR-122, and miR-223, in patients with hepatocellular carcinoma or chronic hepatitis," Mol Carcinog, 50:136-142 (2011).
Zhang et al., "Plasma microRNA-122 as a biomarker for viral-, alcohol-, and chemical-related hepatic diseases," Clin Chem, 56:1830-1838 (2010).
Zhao et al., "A pilot study of circulating miRNAs as potential biomarkers of early stage breast cancer," PLoS One, 5:e13735, 12 pages (2010).
Zhu et al., "Circulating microRNAs in breast cancer and healthy subjects," BMC Res. Notes 2:89, 5 pages (2009).

\* cited by examiner

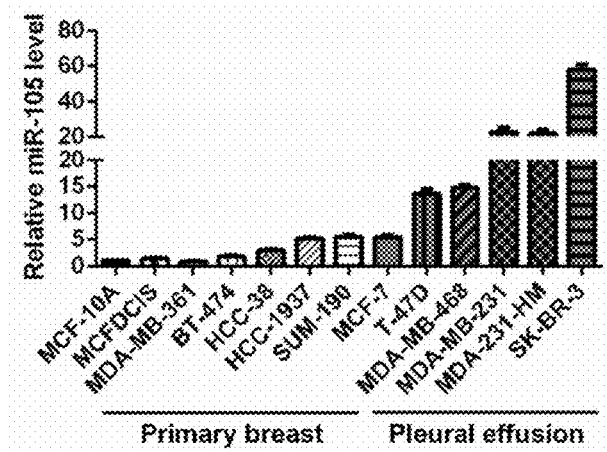
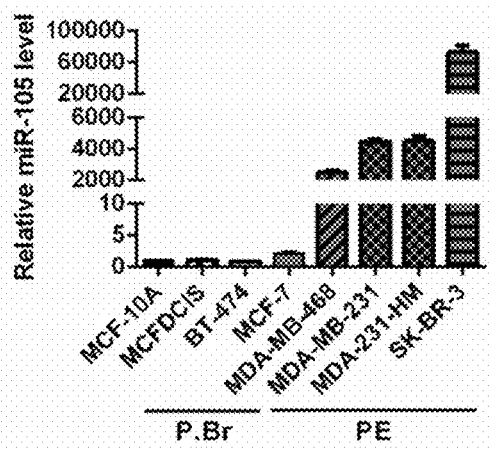
FIG. 2A
FIG. 2B
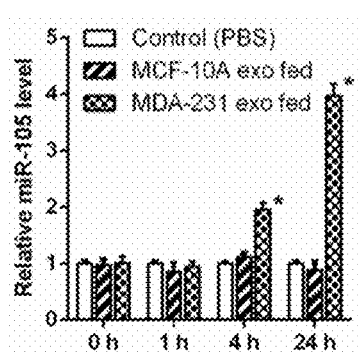
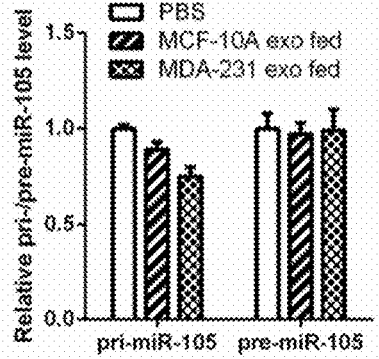
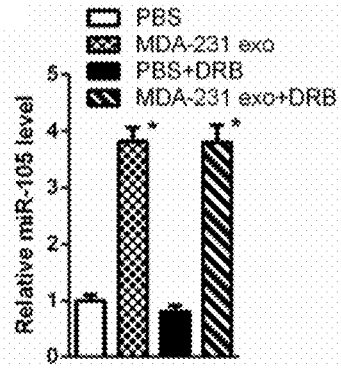
FIG. 2C
FIG. 2D
FIG. 2E
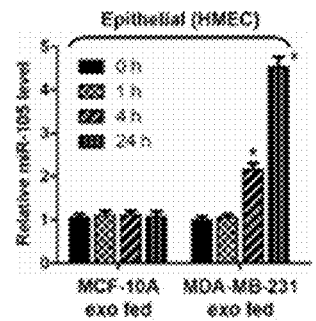
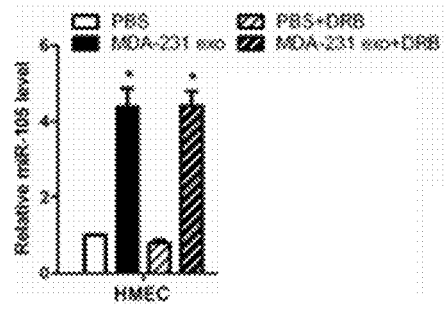
FIG. 2F
FIG. 2G

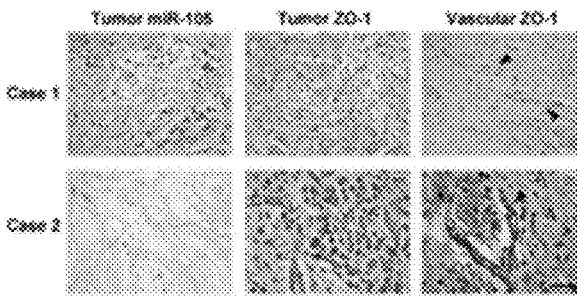
FIG. 8C  FIG. 8D
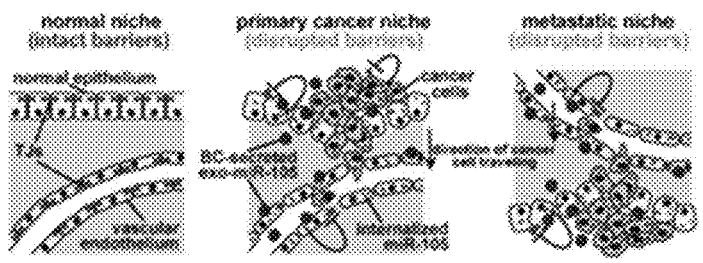
FIG. 8E
FIG. 8F
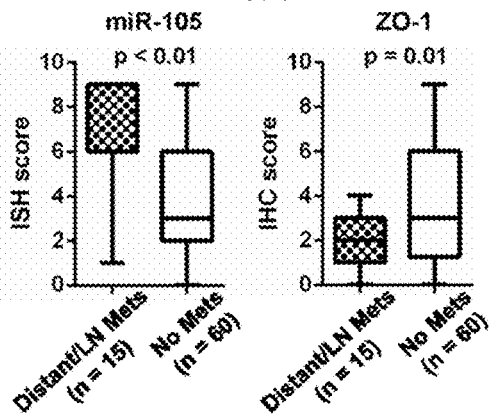
Fig. 8G

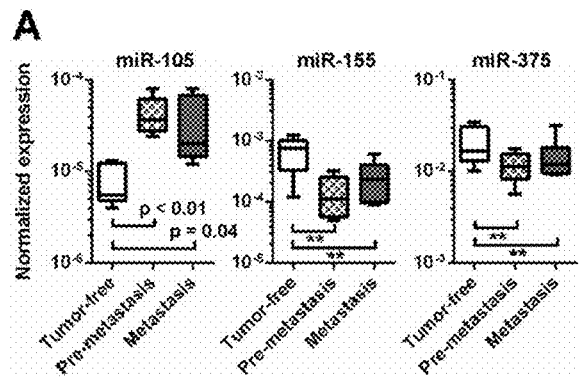
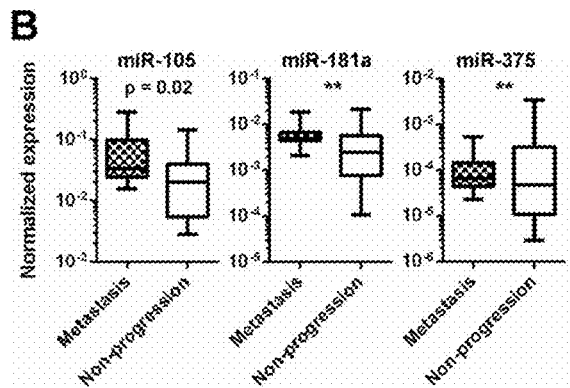
FIG. 8H
FIG. 8I
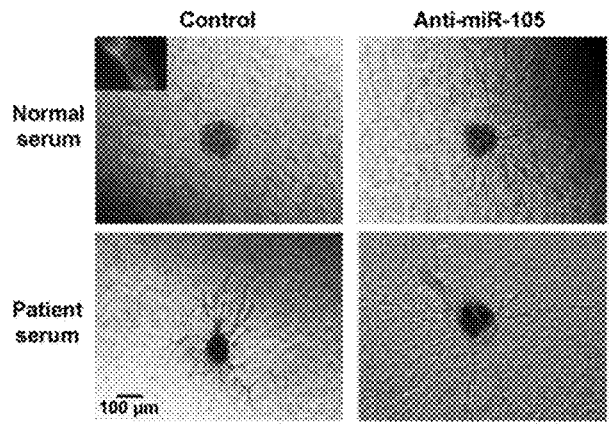
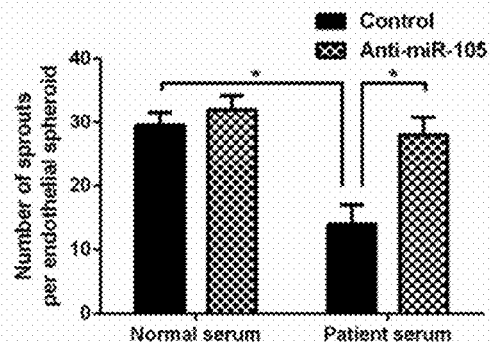
FIG. 8J
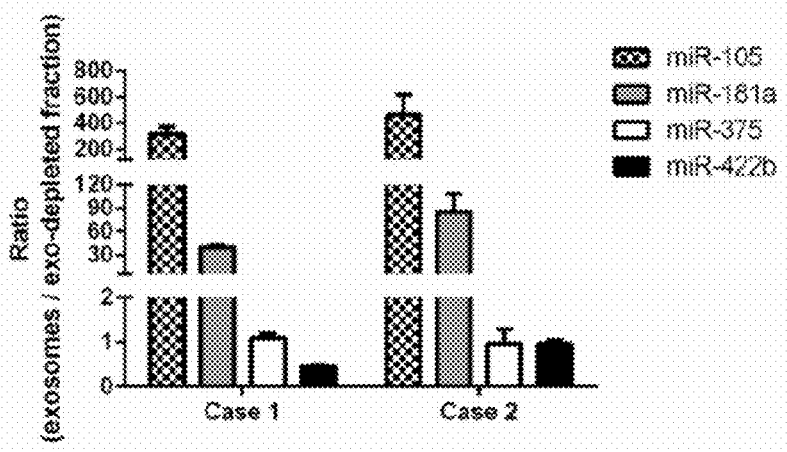
FIG. 8K

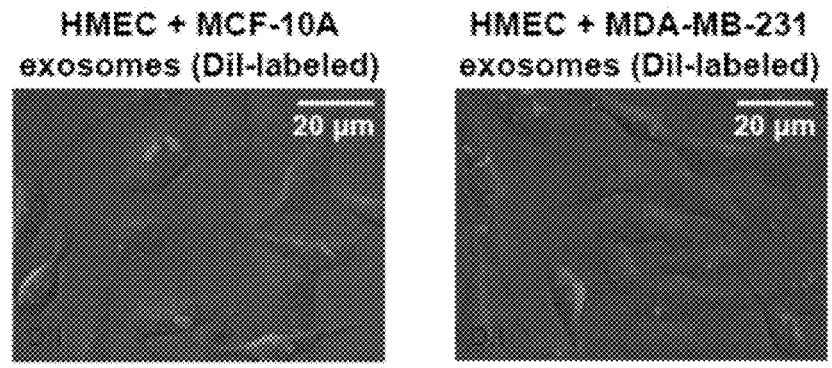
Fig. 9
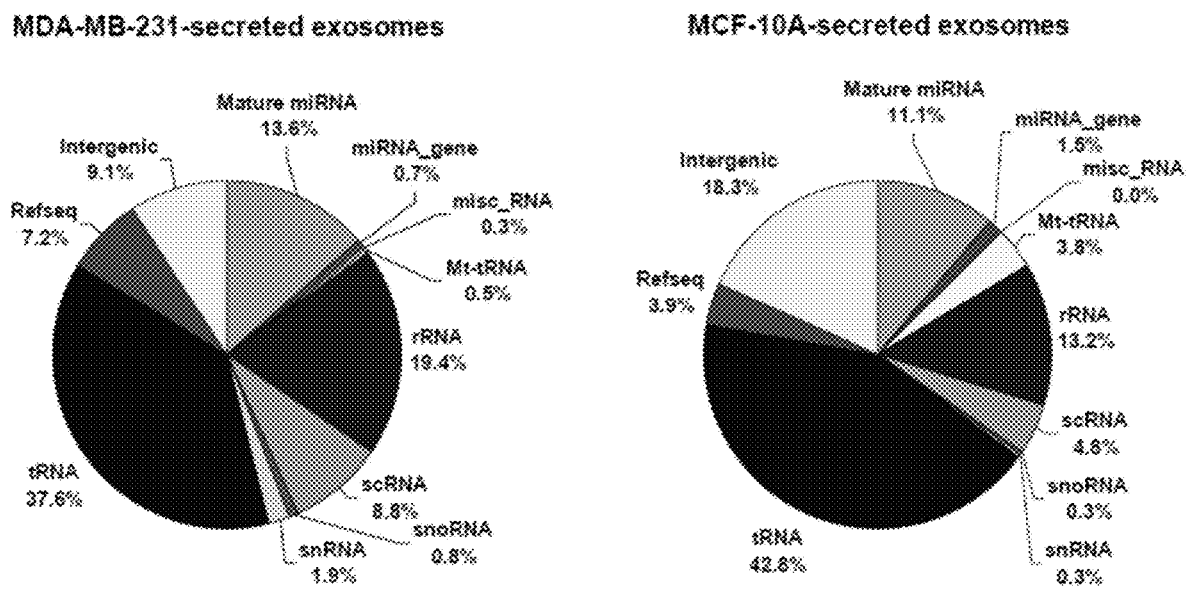
FIG. 10
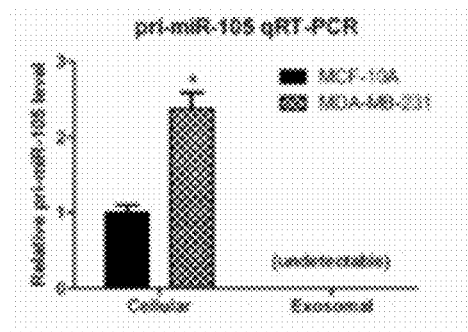 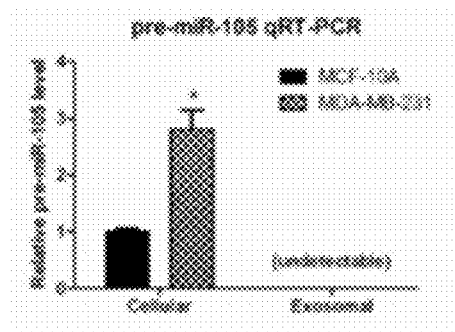
FIG. 11A　　　　　　　　　　　　　FIG. 11B

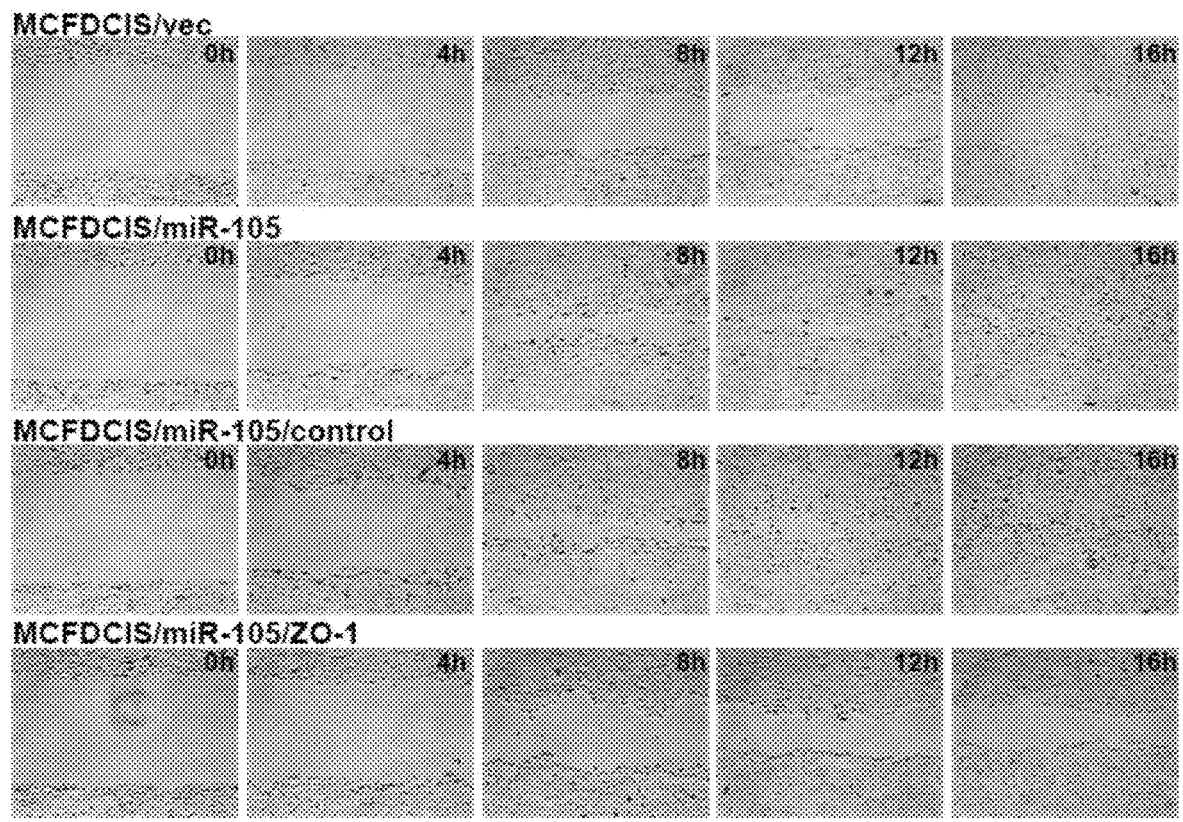
FIG. 13D
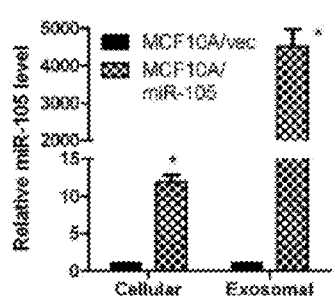 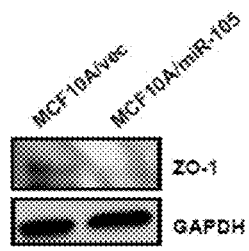 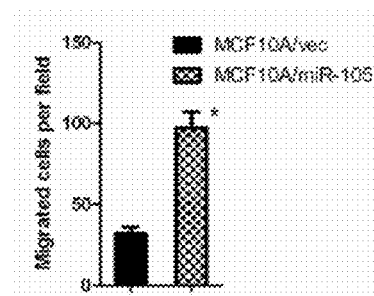
FIG. 14A      FIG. 14B      FIG. 14C

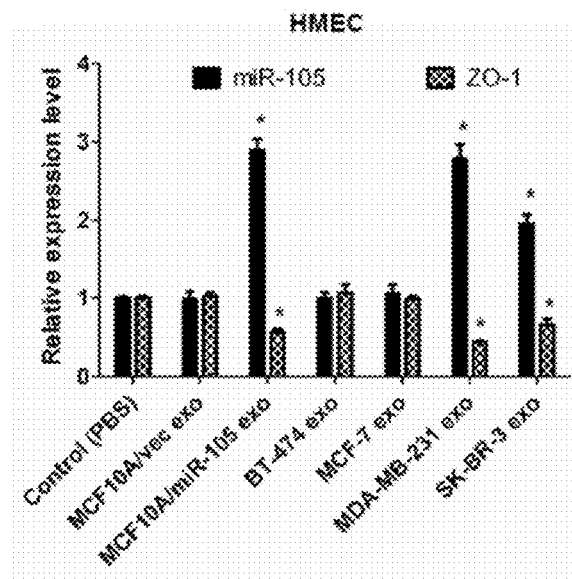
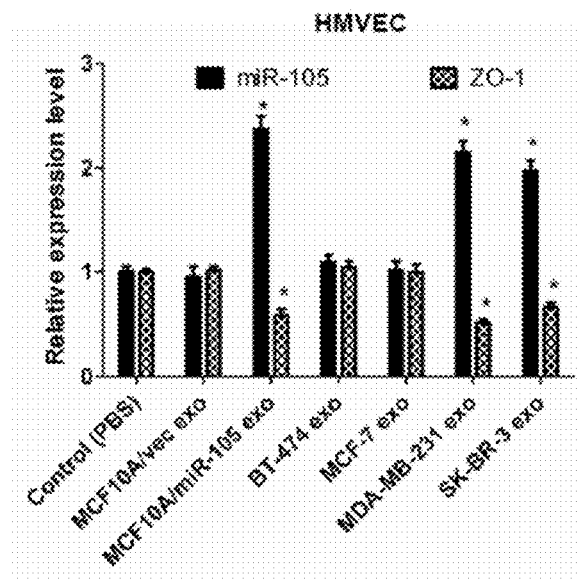
FIG. 15A  FIG. 15B
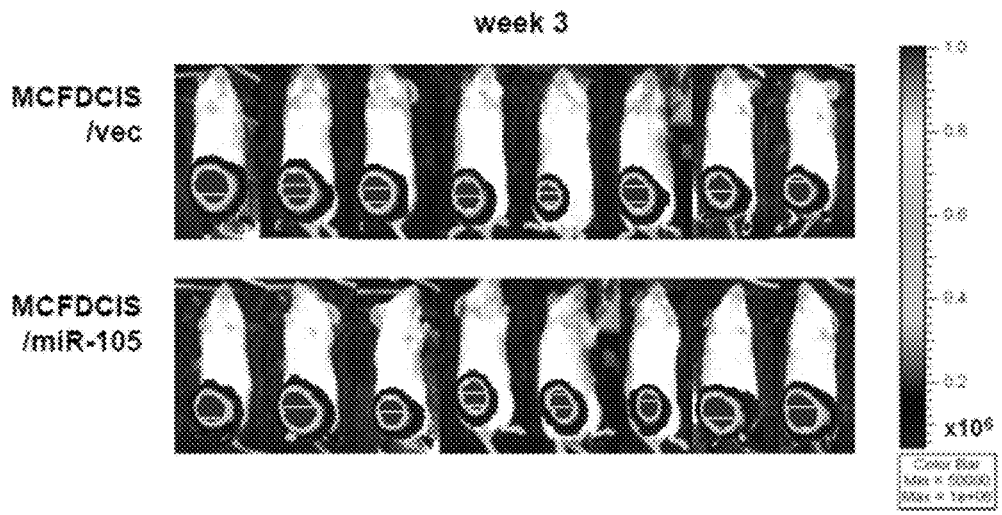
FIG. 16A

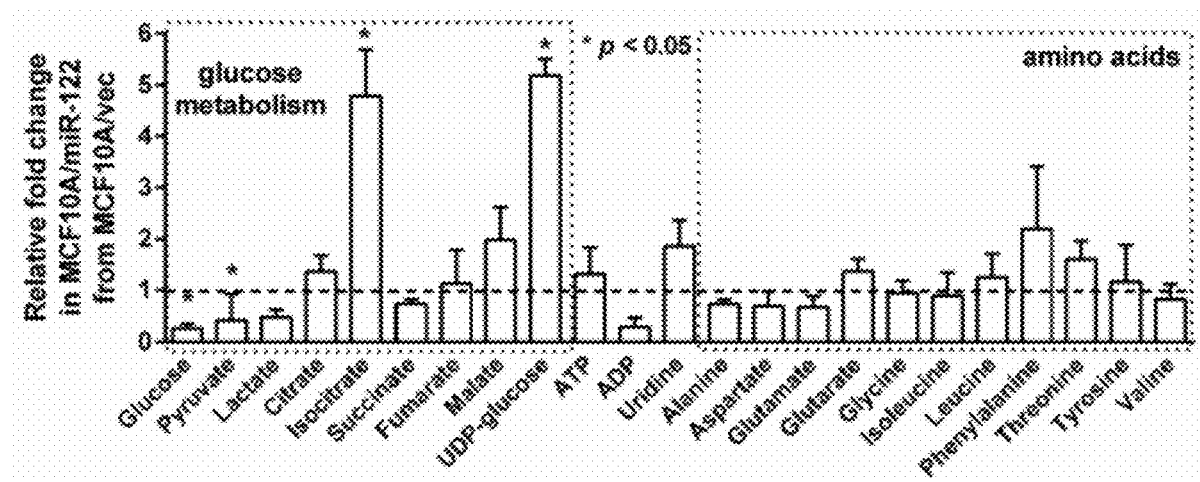
FIG. 24B
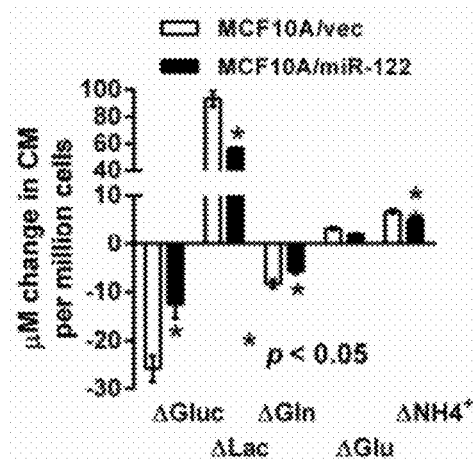
FIG. 24C
```
     miR-122: 3' GUUUGUGGUAACAGUGUGAGGU 5'
 PKM 3'UTR (wt): ...CUGUCCUGCAGCAAACACUCCA...
    mutated (mt): ...CUGUCCUGCAGCAACCUCACAC...
     miR-122: 3' GUUUGUGGUAACAGUGUGAGGU 5'
  CS 3'UTR (wt): ...GAAAGGAUUAAGAUACACUCCU...
    mutated (mt): ...GAAAGGAUUAAGAUCUACGACU...
```
FIG. 24D

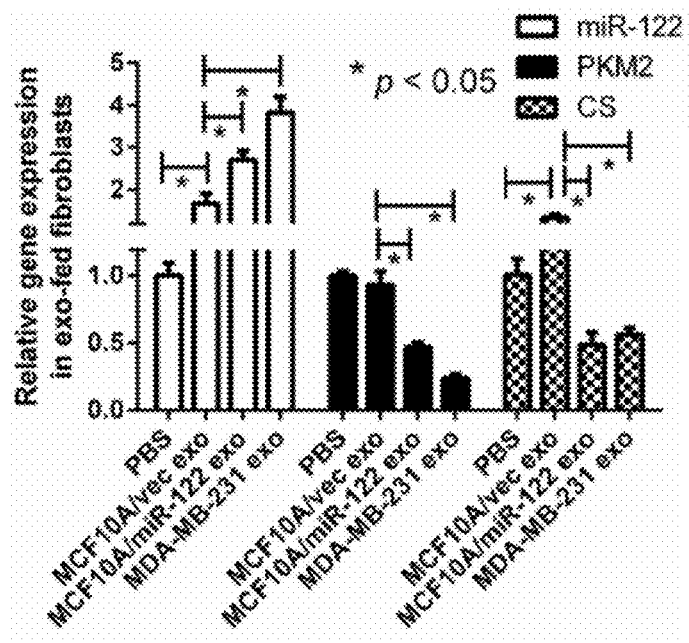
FIG. 25A
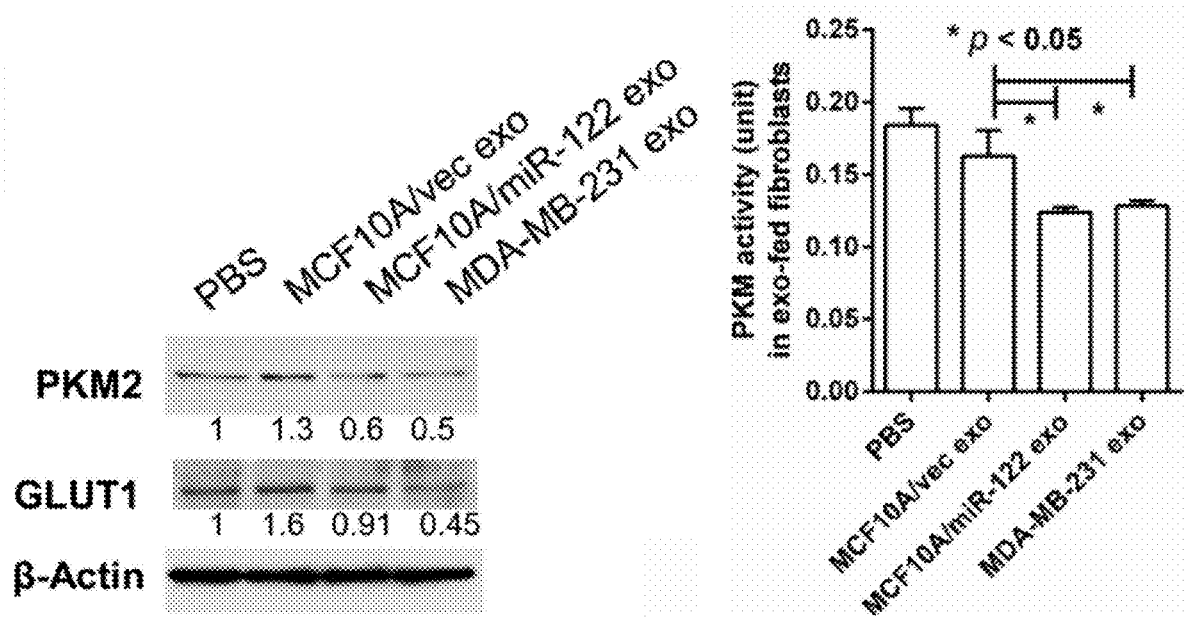
FIG. 25B
FIG. 25C

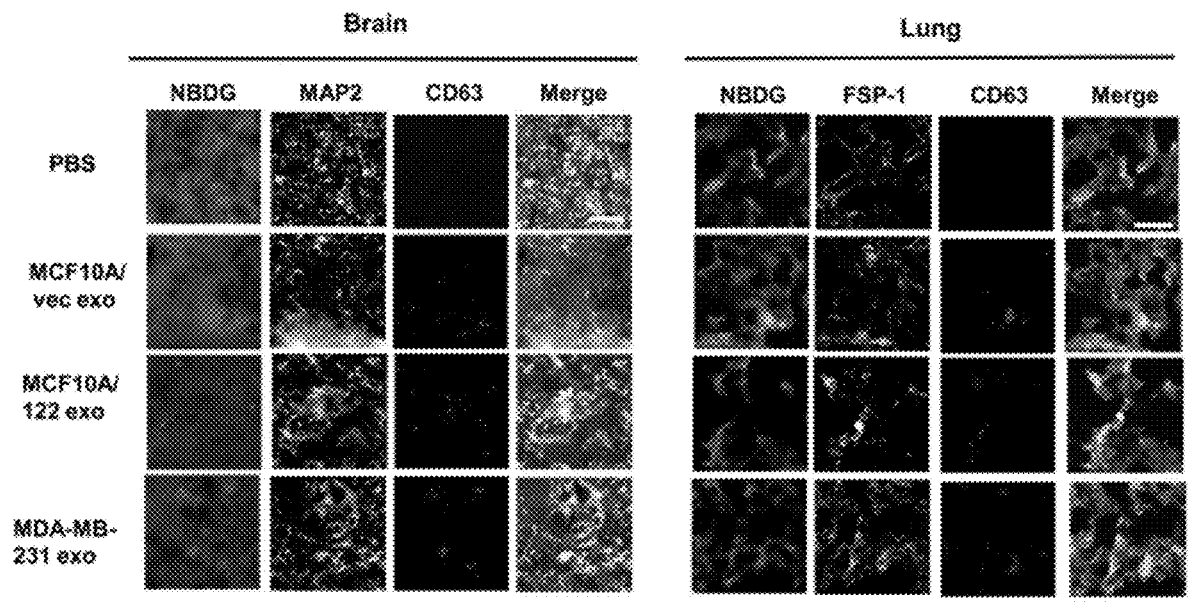
FIG. 26A
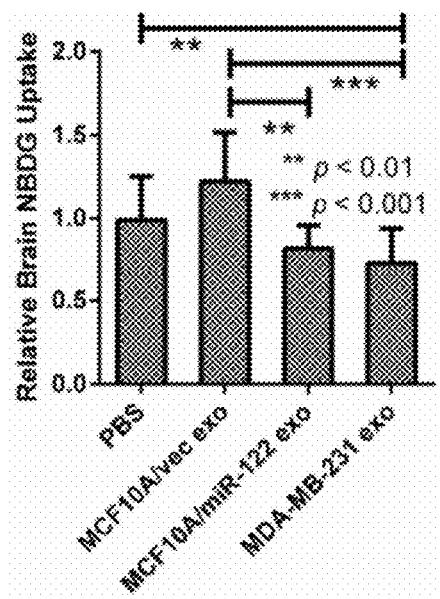 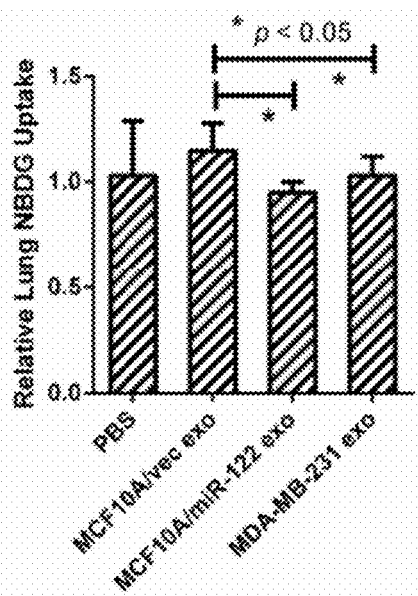
FIG. 26B					FIG. 26C

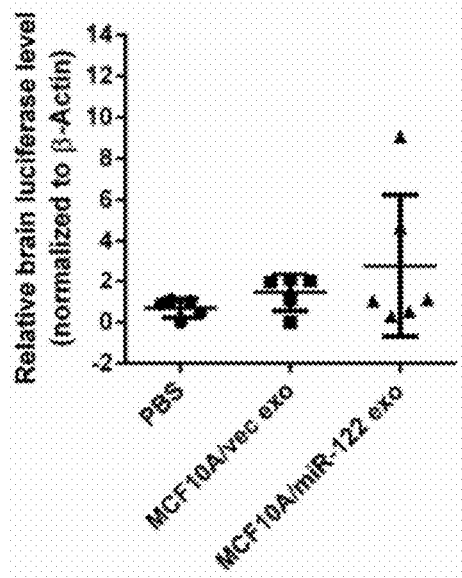 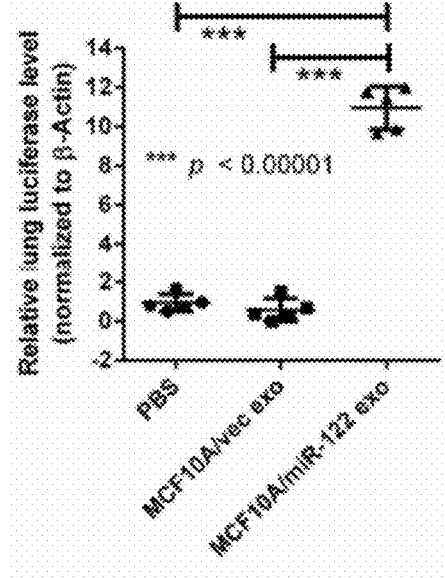
FIG. 26F    FIG. 26G
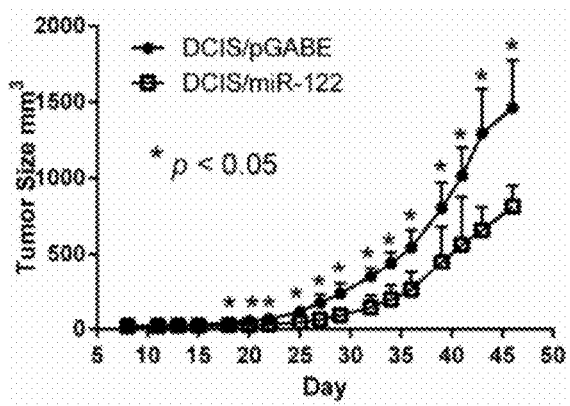
FIG. 27A

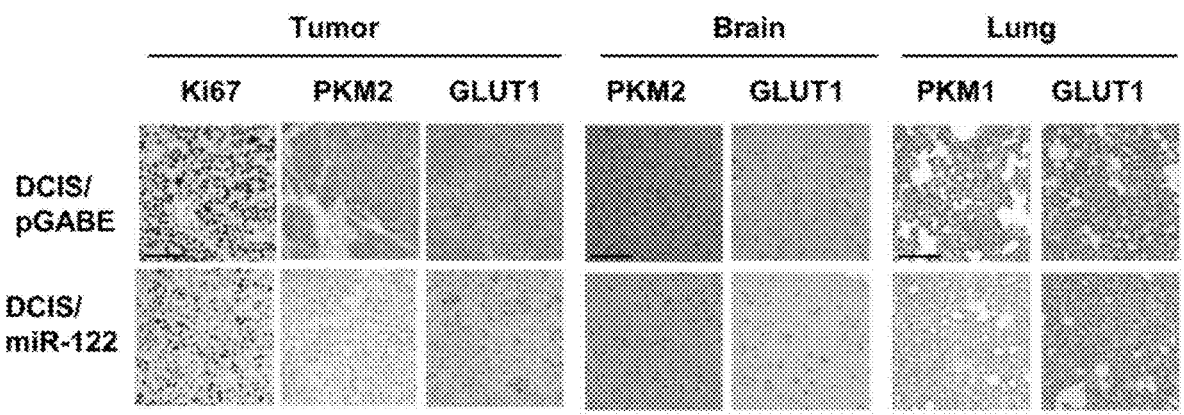
FIG. 27D
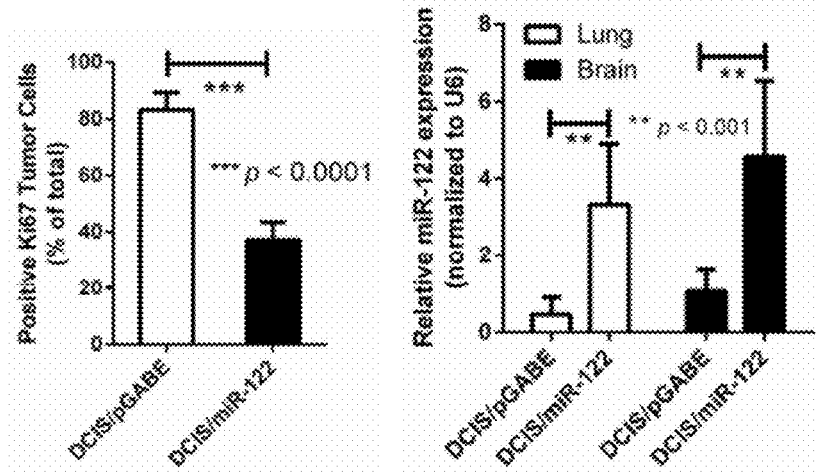
FIG. 27E  FIG. 27F
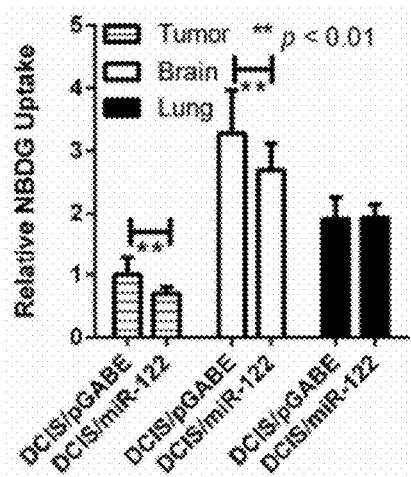 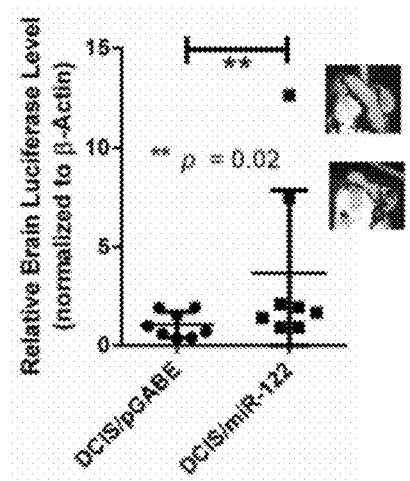
FIG. 27G  FIG. 27H

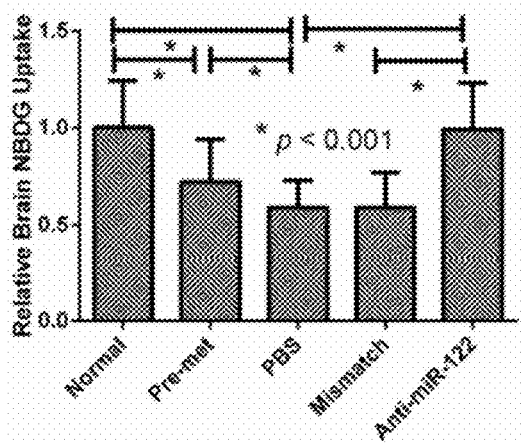
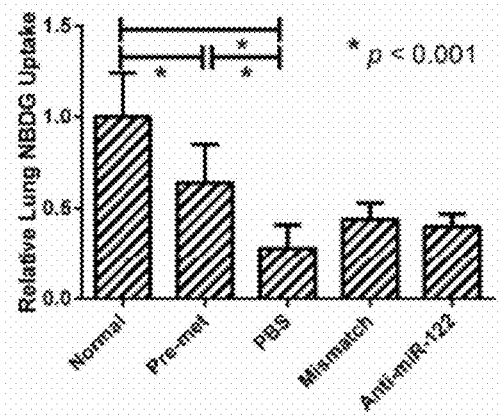
FIG. 28E    FIG. 28F
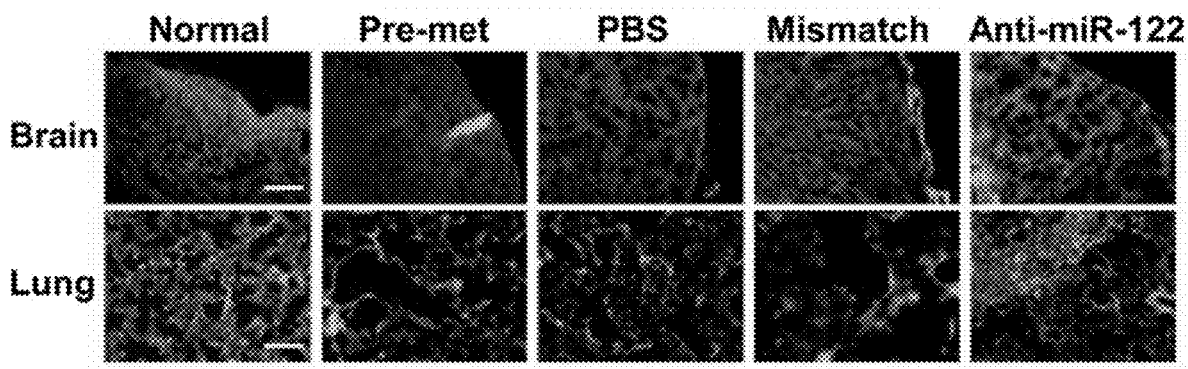
FIG. 28G
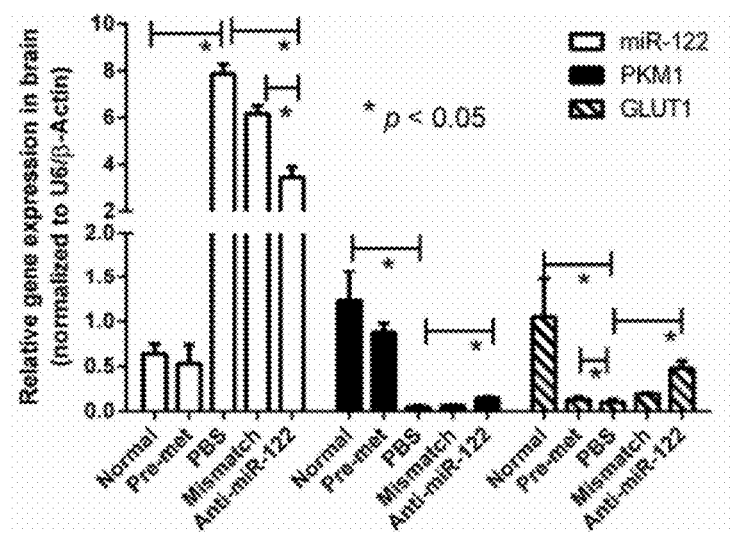
FIG. 28H

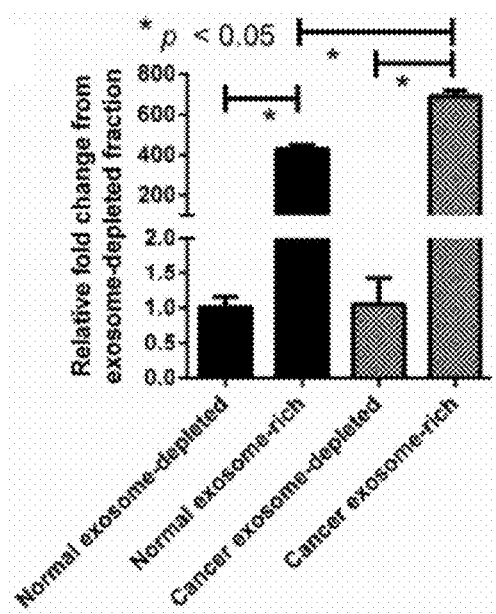
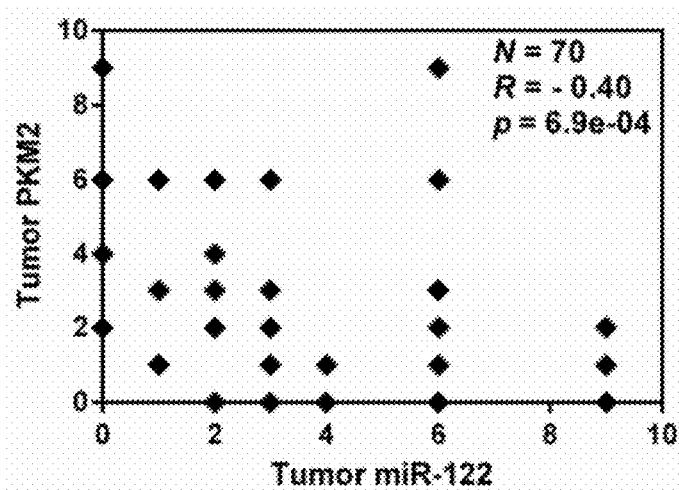
FIG. 29C          FIG. 29D
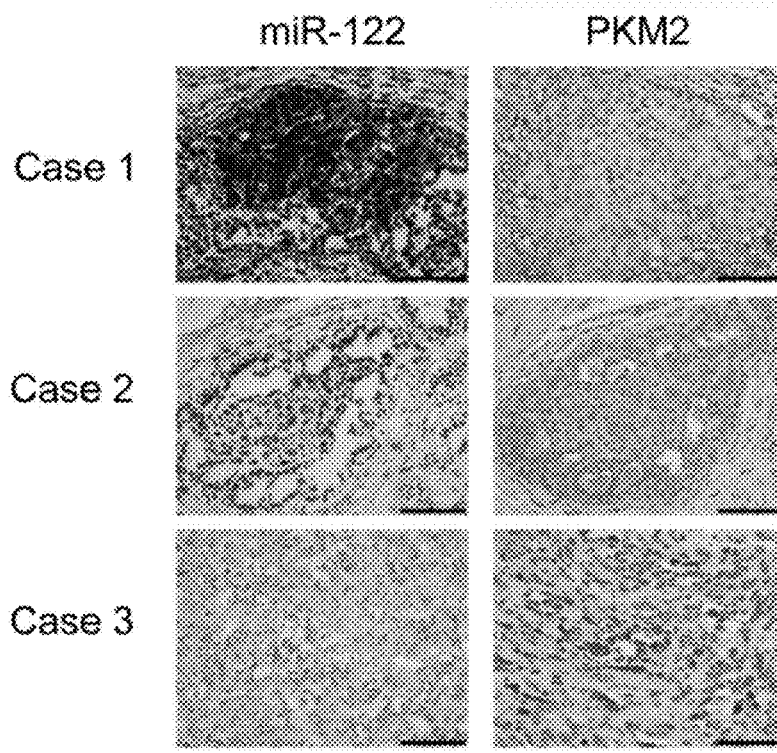
FIG. 29E

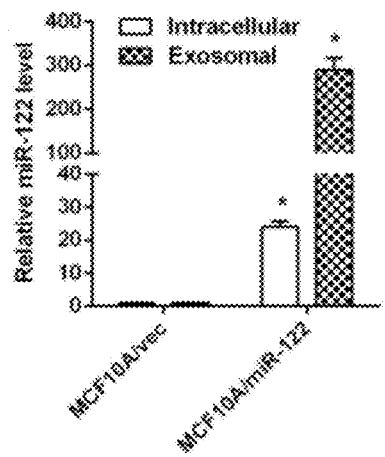
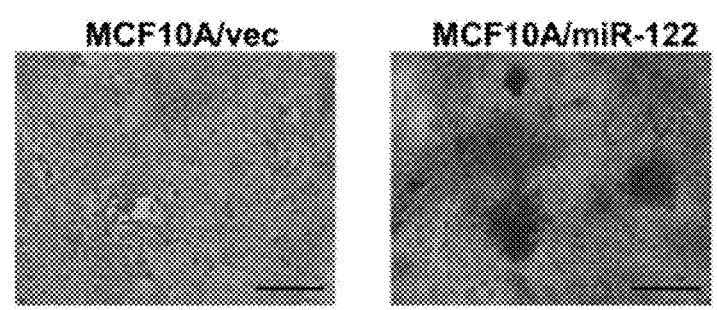
FIG. 30A
FIG. 30B
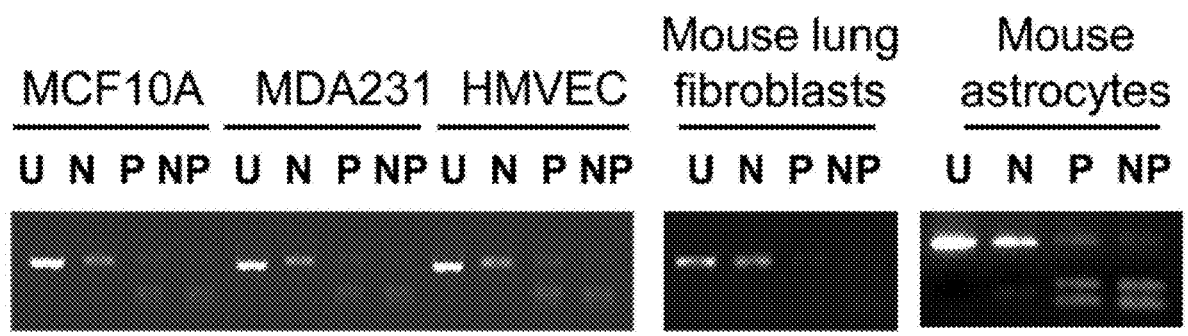
FIG. 31A
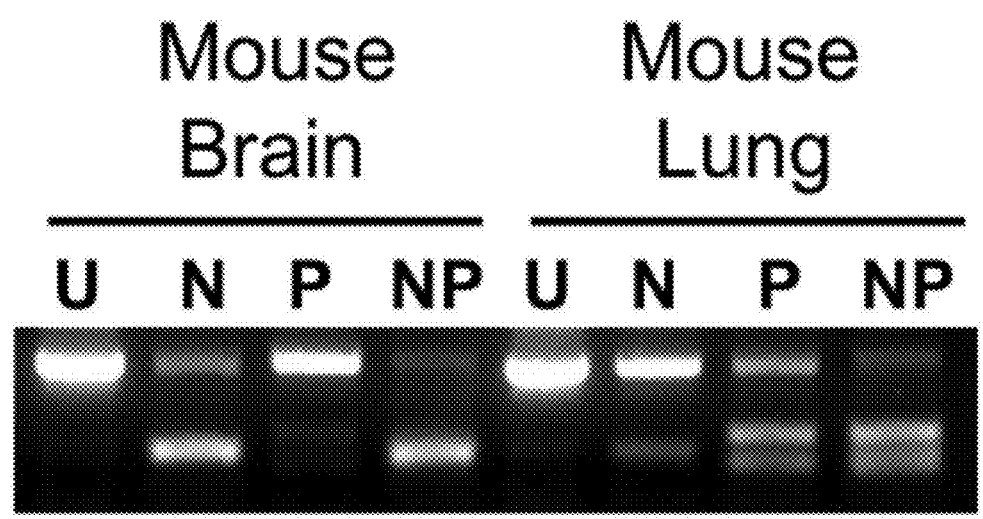
FIG. 31B

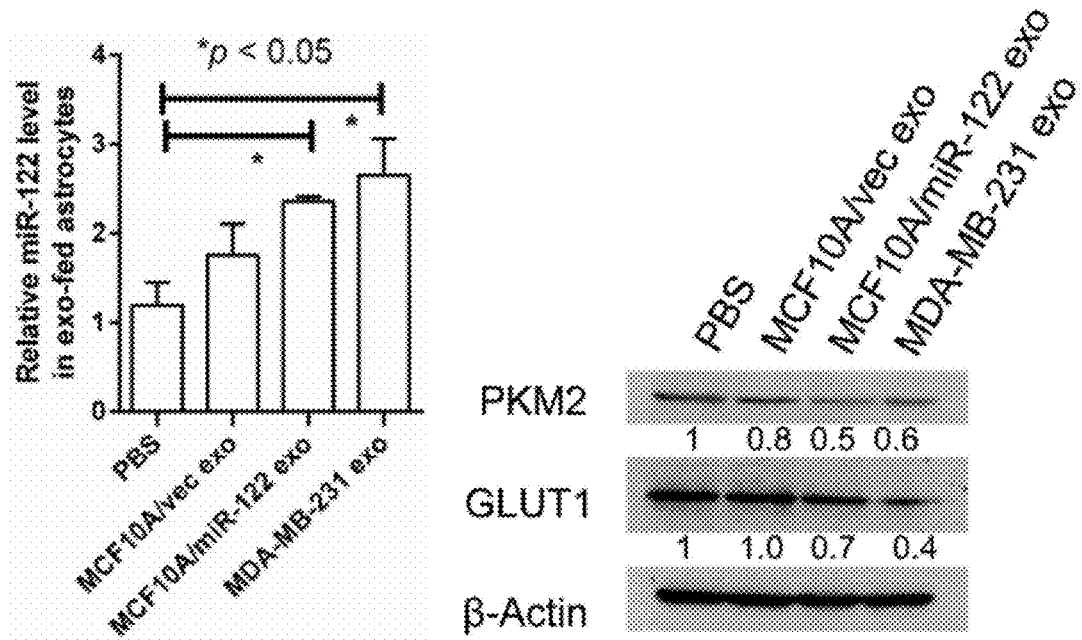
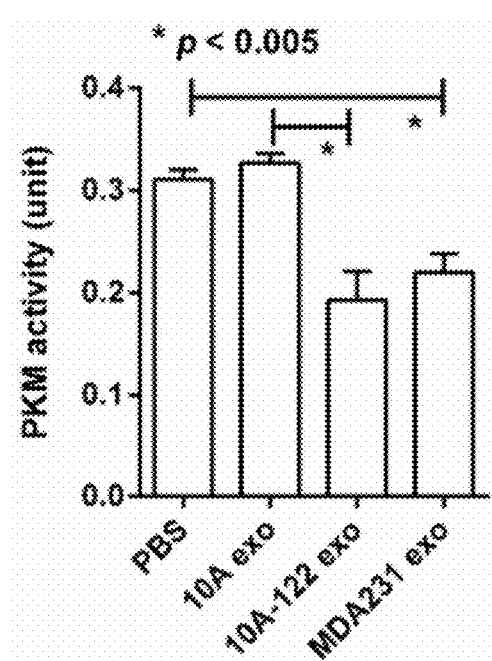
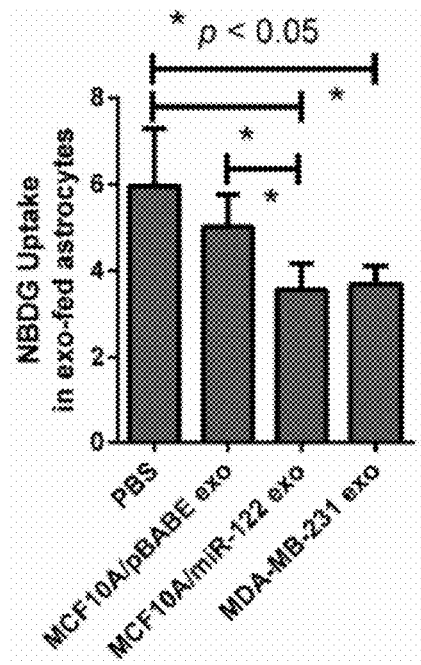
FIG. 32A
FIG. 32B
FIG. 32C
FIG. 32D

```
                           SEQUENCE LISTING

<160> NUMBER OF SEQ ID NOS: 46

<210> SEQ ID NO 1
<211> LENGTH: 81
<212> TYPE: RNA
<213> ORGANISM: homo sapiens

<400> SEQUENCE: 1
ugugcaucgu ggucaaaugc ucagacuccu gugguggcug cucaugcacc acggauguuu      60
gagcaugugc uacggugucu a                                                81

<210> SEQ ID NO 2
<211> LENGTH: 85
<212> TYPE: RNA
<213> ORGANISM: homo sapiens

<400> SEQUENCE: 2
ccuuagcaga gcuguggagu gugacaaugg uguuuguguc uaaacuauca aacgccauua      60
ucacacuaaa uagcuacugc uaggc                                            85

<210> SEQ ID NO 3
<211> LENGTH: 23
<212> TYPE: DNA
<213> ORGANISM: Artificial Sequence
<220> FEATURE:
<223> OTHER INFORMATION: Synthetic Construct

<400> SEQUENCE: 3
accacaggag tctgagcatt tga                                              23

<210> SEQ ID NO 4
<211> LENGTH: 15
<212> TYPE: DNA
<213> ORGANISM: Artificial Sequence
<220> FEATURE:
<223> OTHER INFORMATION: Synthetic Construct

<400> SEQUENCE: 4
ccattgtcac actcc                                                       15

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
tgtttgcctc cttcttcgtc                                                  20

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
acaggaacaa atggctttgg                                                  20
```

```
<210> SEQ ID NO 7
<211> LENGTH: 23
<212> TYPE: DNA
<213> ORGANISM: Artificial Sequence
<220> FEATURE:
<223> OTHER INFORMATION: Synthetic Construct

<400> SEQUENCE: 7
atggaggaaa cagctatatg gga                                              23

<210> SEQ ID NO 8
<211> LENGTH: 21
<212> TYPE: DNA
<213> ORGANISM: Artificial Sequence
<220> FEATURE:
<223> OTHER INFORMATION: Synthetic Construct

<400> SEQUENCE: 8
ccaaatccaa atccaggagc c                                                21

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
ctaccacatc caaggaagca                                                  20

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct

<400> SEQUENCE: 10
tttttcgtca ctacctcccc g                                                21

<210> SEQ ID NO 11
<211> LENGTH: 32
<212> TYPE: DNA
<213> ORGANISM: Artificial Sequence
<220> FEATURE:
<223> OTHER INFORMATION: Synthetic Construct

<400> SEQUENCE: 11
gcagctgaat tcgagctgac aaggttcccc ta                                    32

<210> SEQ ID NO 12
<211> LENGTH: 32
<212> TYPE: DNA
<213> ORGANISM: Artificial Sequence
<220> FEATURE:
<223> OTHER INFORMATION: Synthetic Construct

<400> SEQUENCE: 12
tagtacgtcg acaaagcaaa cgatgccaag ac                                    32

<210> SEQ ID NO 13
<211> LENGTH: 29
<212> TYPE: DNA
<213> ORGANISM: Artificial Sequence
<220> FEATURE:
<223> OTHER INFORMATION: Synthetic Construct
```

<400> SEQUENCE: 13
gaagttggat ccagatcagg acctcagca                                    29

<210> SEQ ID NO 14
<211> LENGTH: 30
<212> TYPE: DNA
<213> ORGANISM: Artificial Sequence
<220> FEATURE:
<223> OTHER INFORMATION: Synthetic Construct

<400> SEQUENCE: 14
gaagttgaat tcggctctgg ggtccatcac                                   30

<210> SEQ ID NO 15
<211> LENGTH: 31
<212> TYPE: DNA
<213> ORGANISM: Artificial Sequence
<220> FEATURE:
<223> OTHER INFORMATION: Synthetic Construct

<400> SEQUENCE: 15
gaagttggat ccttacctcc ccaccagatc c                                 31

<210> SEQ ID NO 16
<211> LENGTH: 30
<212> TYPE: DNA
<213> ORGANISM: Artificial Sequence
<220> FEATURE:
<223> OTHER INFORMATION: Synthetic Construct

<400> SEQUENCE: 16
gaagttgaat tcactttcac ccagtctcca                                   30

<210> SEQ ID NO 17
<211> LENGTH: 24
<212> TYPE: DNA
<213> ORGANISM: Artificial Sequence
<220> FEATURE:
<223> OTHER INFORMATION: Synthetic Construct

<400> SEQUENCE: 17
attatttgag gaactccgcc gcct                                         24

<210> SEQ ID NO 18
<211> LENGTH: 23
<212> TYPE: DNA
<213> ORGANISM: Artificial Sequence
<220> FEATURE:
<223> OTHER INFORMATION: Synthetic Construct

<400> SEQUENCE: 18
attccgggtc acagcaatga tgg                                          23

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19
ggtggcatga gaggcatgaa                                              20

<210> SEQ ID NO 20

<210> SEQ ID NO 20
<211> LENGTH: 21
<212> TYPE: DNA
<213> ORGANISM: Artificial Sequence
<220> FEATURE:
<223> OTHER INFORMATION: Synthetic Construct

<400> SEQUENCE: 20
tagccttggg tagcagtttc t                                              21

<210> SEQ ID NO 21
<211> LENGTH: 21
<212> TYPE: DNA
<213> ORGANISM: Artificial Sequence
<220> FEATURE:
<223> OTHER INFORMATION: Synthetic Construct

<400> SEQUENCE: 21
ggccaagagt gtgctaaaga a                                              21

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct

<400> SEQUENCE: 22
acagcgttga tgccagacag                                                20

<210> SEQ ID NO 23
<211> LENGTH: 19
<212> TYPE: DNA
<213> ORGANISM: Artificial Sequence
<220> FEATURE:
<223> OTHER INFORMATION: Synthetic Construct

<400> SEQUENCE: 23
gctgggcatc gttgttgga                                                 19

<210> SEQ ID NO 24
<211> LENGTH: 23
<212> TYPE: DNA
<213> ORGANISM: Artificial Sequence
<220> FEATURE:
<223> OTHER INFORMATION: Synthetic Construct

<400> SEQUENCE: 24
gcactttgta ggatagcagg aag                                            23

<210> SEQ ID NO 25
<211> LENGTH: 20
<212> TYPE: DNA
<213> ORGANISM: Artificial Sequence
<220> FEATURE:
<223> OTHER INFORMATION: Synthetic Construct

<400> SEQUENCE: 25
ctgtgccatc ctgatgactg                                                20

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct

<400> SEQUENCE: 26

```
cgtagctcat ggctggaact                                                 20

<210> SEQ ID NO 27
<211> LENGTH: 19
<212> TYPE: DNA
<213> ORGANISM: Artificial Sequence
<220> FEATURE:
<223> OTHER INFORMATION: Synthetic Construct

<400> SEQUENCE: 27
ccgcgtctgg tatgtctcc                                                  19

<210> SEQ ID NO 28
<211> LENGTH: 22
<212> TYPE: DNA
<213> ORGANISM: Artificial Sequence
<220> FEATURE:
<223> OTHER INFORMATION: Synthetic Construct

<400> SEQUENCE: 28
cctgggtagt aaaggtcttg ga                                              22

<210> SEQ ID NO 29
<211> LENGTH: 20
<212> TYPE: DNA
<213> ORGANISM: Artificial Sequence
<220> FEATURE:
<223> OTHER INFORMATION: Synthetic Construct

<400> SEQUENCE: 29
aaccatgacc aagtgcagaa                                                 20

<210> SEQ ID NO 30
<211> LENGTH: 20
<212> TYPE: DNA
<213> ORGANISM: Artificial Sequence
<220> FEATURE:
<223> OTHER INFORMATION: Synthetic Construct

<400> SEQUENCE: 30
agccctttct ccatctcctt                                                 20

<210> SEQ ID NO 31
<211> LENGTH: 21
<212> TYPE: DNA
<213> ORGANISM: Artificial Sequence
<220> FEATURE:
<223> OTHER INFORMATION: Synthetic Construct

<400> SEQUENCE: 31
ctaccacatc caaggaaggc a                                               21

<210> SEQ ID NO 32
<211> LENGTH: 21
<212> TYPE: DNA
<213> ORGANISM: Artificial Sequence
<220> FEATURE:
<223> OTHER INFORMATION: Synthetic Construct

<400> SEQUENCE: 32
tttttcgtca ctacctcccc g                                               21

<210> SEQ ID NO 33
<211> LENGTH: 18
<212> TYPE: DNA
```

```
<213> ORGANISM: Artificial Sequence
<220> FEATURE:
<223> OTHER INFORMATION: Synthetic Construct

<400> SEQUENCE: 33
gcaggaaccg aagtacgc                                                 18

<210> SEQ ID NO 34
<211> LENGTH: 20
<212> TYPE: DNA
<213> ORGANISM: Artificial Sequence
<220> FEATURE:
<223> OTHER INFORMATION: Synthetic Construct

<400> SEQUENCE: 34
tgtgttccag gaaggtgtca                                               20

<210> SEQ ID NO 35
<211> LENGTH: 21
<212> TYPE: DNA
<213> ORGANISM: Artificial Sequence
<220> FEATURE:
<223> OTHER INFORMATION: Synthetic Construct

<400> SEQUENCE: 35
aggctagact ggtcacacaa t                                             21

<210> SEQ ID NO 36
<211> LENGTH: 22
<212> TYPE: DNA
<213> ORGANISM: Artificial Sequence
<220> FEATURE:
<223> OTHER INFORMATION: Synthetic Construct

<400> SEQUENCE: 36
aggacaggta agggtctgaa ag                                            22

<210> SEQ ID NO 37
<211> LENGTH: 20
<212> TYPE: DNA
<213> ORGANISM: Artificial Sequence
<220> FEATURE:
<223> OTHER INFORMATION: Synthetic Construct

<400> SEQUENCE: 37
gggcctaagg tcacatgaag                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic Construct

<400> SEQUENCE: 38
ccagtgttat agccgaactg                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic Construct

<400> SEQUENCE: 39
cgcttcctta cctggttgat                                               20
```

```
<210> SEQ ID NO 40
<211> LENGTH: 20
<212> TYPE: DNA
<213> ORGANISM: Artificial Sequence
<220> FEATURE:
<223> OTHER INFORMATION: Synthetic Construct

<400> SEQUENCE: 40
gagcgaccaa aggaaccata                                              20

<210> SEQ ID NO 41
<211> LENGTH: 20
<212> TYPE: DNA
<213> ORGANISM: Artificial Sequence
<220> FEATURE:
<223> OTHER INFORMATION: Synthetic Construct

<400> SEQUENCE: 41
cgaggcccag agcaagagag                                              20

<210> SEQ ID NO 42
<211> LENGTH: 20
<212> TYPE: DNA
<213> ORGANISM: Artificial Sequence
<220> FEATURE:
<223> OTHER INFORMATION: Synthetic Construct

<400> SEQUENCE: 42
cggttggcct tagggttcag                                              20

<210> SEQ ID NO 43
<211> LENGTH: 15
<212> TYPE: DNA
<213> ORGANISM: Artificial Sequence
<220> FEATURE:
<223> OTHER INFORMATION: Synthetic Construct

<400> SEQUENCE: 43
ccattctcac actgc                                                   15

<210> SEQ ID NO 44
<211> LENGTH: 23
<212> TYPE: RNA
<213> ORGANISM: Artificial Sequence
<220> FEATURE:
<223> OTHER INFORMATION: Synthetic Construct

<400> SEQUENCE: 44
acaaacacca uugucacacu cca                                          23

<210> SEQ ID NO 45
<211> LENGTH: 15
<212> TYPE: DNA
<213> ORGANISM: Artificial Sequence
<220> FEATURE:
<223> OTHER INFORMATION: Synthetic Construct

<400> SEQUENCE: 45
caaacaccat tgtca                                                   15

<210> SEQ ID NO 46
<211> LENGTH: 15
<212> TYPE: DNA
<213> ORGANISM: Artificial Sequence
<220> FEATURE:
```

```
<223> OTHER INFORMATION: Synthetic Construct

<400> SEQUENCE: 46
ttagagtgat aatgg                                                    15
```

METHODS AND COMPOSITIONS FOR TREATMENT OF BREAST CANCER

CROSS-REFERENCE TO RELATED APPLICATION

This application claims priority to U.S. Provisional Application No. 61/775,243, filed Mar. 8, 2013, which is incorporated by reference herein in its entirety.

STATEMENT AS TO RIGHTS TO INVENTIONS MADE UNDER FEDERALLY SPONSORED RESEARCH AND DEVELOPMENT

The present was supported at least in part by government funding from the National Institutes of Health, Grant No. R01CA166020, R01CA163586 and P30CA33572. The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 95058-902010_ST25.TXT, created Mar. 10, 2014, 9,138 bytes, machine format IBM-PC, MS-Windows operating system, is hereby incorporated by reference.

BACKGROUND

MiRNAs are small non-coding RNA molecules of approximately 20 to 25 nucleotides in length that typically base-pair with the 3' untranslated regions (UTRs) of protein-encoding messenger RNAs (mRNAs). This binding negatively regulates gene expression of the mRNA by leading to degradation or translation blockade of the mRNA. Through regulation of greater than 60% of all protein-coding genes, miRNAs are involved in a variety of biological pathways including proliferation, differentiation, cell growth, cell death, stress resistance, and metabolism. Deregulation of miRNAs has been linked to diseases and disorders including metabolic disorders and cancer. MiRNAs are also detected in virtually all biofluids including serum and plasma as miRNAs can be secreted through microvesicles (such as exosomes, shedding vesicles, and apoptotic bodies) or in complexes with protein or lipid-based carriers. Accumulating evidence indicate that miRNAs can be transferred to neighboring or distant cells through these secretory forms to modulate cell function. Extracellular miRNAs are therefore emerging as a new group of messengers and effectors in intercellular communication.

Cancer continues to be a major cause of death in the worldwide population. Breast cancer, in particulate, is a common form of cancer that requires aggressive treatment and detection methods. Therefore, there is a need in the art for effective detection and treatments of cancer, including breast cancer. Provided herein, inter alia, are methods and compositions addressing these and other needs in the art.

SUMMARY

Methods of treating breast cancer in a subject in need thereof comprising administering to the subject an effective amount of an inhibitor of miR-105 or an inhibitor of miR-122 are provided.

Provided herein are also methods of determining a level of miR-105 or a level of miR-122 in a subject that has or is at risk for developing breast cancer. A higher level of miR-105 or miR-122 as compared to a control indicates that the subject has or is at risk of developing breast cancer. The method includes the steps of obtaining a biological sample from the subject, and determining a level of miR-105 or a level of miR-122 in the biological sample. Optionally, the method includes selecting a subject that has or is at risk for developing breast cancer.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 1A are electron microscope (EM) images of exosomes secreted by MCF-10A and MDA-MB-231 cells. FIG. 1B are phase contrast images of primary human microvascular endothelial cells (HMVECs) incubated with DiI-labeled exosomes for 24 hours before fluorescent and image capture. FIG. 1C are graphs of human mammary epithelial cells (HMECs) and HMVECs incubated with DiI-labeled exosomes for indicated time analyzed by flow cytometry for DiI uptake. FIG. 1D is a graph showing quantitation of cell migration. After 48 hours incubation with exosomes or PBS (as control), recipient cells were analyzed for transwell migration and cells that had migrated within 16 hours (for HMECs) or 8 hours (for HMVECs) were quantified from triplicate wells. FIG. 1E is a graph showing quantitation of cell migration. Cells transfected with an equal amount of total or small (<200 nt) RNA extracted from MCF-10A or MDA-MB-231 (abbreviated to 10A or 231, respectively) secreted exosomes, or control RNA (cel-miR-67), were subjected to transwell migration at 48 hours post transfection. $*p<0.005$ compared to control group. Results are presented as mean±standard deviation (SD).

FIGS. 2A, 2B, 2C, 2D, 2E, 2F, and 2G, show miR-105 is specifically expressed and secreted by MBC cells and can be transferred to endothelial cells via exosome secretion. FIGS. 2A and 2B are graphs showing cellular (FIG. 2A) and exosomal (FIG. 2B) RNA extracted from various breast cell lines and subjected to miR-105 RT-qPCR. Data was normalized to levels of U6 (cellular; FIG. 2A) or miR-16 (exosomal; FIG. 2B), and compared to the nontumor line MCF-10A. MBC lines originally isolated from pleural effusion are indicated. FIG. 2C is a graph showing miR-105 levels. RNA was extracted from HMVECs incubated with exosomes of different origins for indicated time and analyzed for miR-105 level using U6 as internal control. At each time point, data was compared to PBS-treated cells. FIG. 2D is a graph showing pri-/pre-miR-105 levels. RNA extracted from HMVECs incubated with exosomes of different origins for 24 hours (or PBS as control) was analyzed for the level of primiR-105 or pre-miR-105. FIG. 2E is a graph showing miR-105 levels. MDA-MB-231-secreted exosomes were fed to HMVECs in the presence or absence of DRB (20 μM). After 24 hours, RNA extracted from the recipient cells was analyzed for miR-105 level. $*p<0.005$ compared to PBS treatment. Results are presented as mean±SD. FIG. 2F is a graph showing miR-105 levels in HMECs. RNA was extracted from HMECs incubated with exosomes of different origins for indicated time and analyzed for miR-105 level using U6 as internal control. FIG. 2G is a graph showing miR-105 levels HMECs. MDA-MB-231-secreted exosomes were fed to recipient cells in the presence or absence of DRB (20 μM). After 24 hours, RNA extracted from the recipient cells was analyzed for miR-105 level. $*p<0.005$ compared to PBS treatment. Results are presented as mean±SD.

FIGS. 3A, 3B, 3C, 3D, 3E, 3F, 3G, and 3H, show miR-105 regulates migration through targeting the tight junction protein ZO-1. FIG. 3A shows the predicted miR-105 binding sites (I-IV) in the 3'UTR of human ZO-1 are indicated together with the corresponding sequences in mouse ZO-1. The indicated psiCHECK luciferase reporters containing each of the predicted sites or both site I and site II, or a control reporter containing a scrambled sequence, were used to transfect HMECs that were also infected with retrovirus expressing miR-105 or vector (as control). Luciferase activity was analyzed at 48 hours post transfection, and compared to the cells infected with the control virus. FIG. 3B is a graph showing MCFDCIS cells stably transduced with miR-105 or vector analyzed for miR-105 expression and secretion by RT-qPCR. FIG. 3C is a gel image showing transduced MCFDCIS cells with or without transfection with a ZO-1 expression plasmid or vector control analyzed by Western blot for the expression of ZO-1 and GAPDH (as loading control) at 48 hours post transfection. FIG. 3D is a graph showing the indicated cells subjected to transwell migration assay and cells that had migrated within 8 hours were quantified from triplicate wells. FIG. 3E is a gel image showing MDA-231-HM cells transfected with an anti-miR-105 compound or control compound, as well as MCF-7 cells stably transduced with miR-105 with or without transfection with a ZO-1 expression plasmid analyzed by Western blot for ZO-1 expression. FIGS. 3F and 3G are graphs showing the transfected MDA-231-HM (FIG. 3G) and MCF-7 cells (FIG. 3F) subjected to transwell migration assays. Cells that had migrated within 8 hours (for MDA-231-HM) or 96 hours (for MCF-7) were quantified from triplicate wells. $*p<0.005$. FIG. 3H is a graph showing the effect of exosomes of various origins on ZO-1 expression in HMVECs. At 48 hours after exosome treatment, RNA was extracted from the recipient HMVECs and subjected to miR-105 and ZO-1 RT-qPCR using U6 and 18S as the corresponding internal reference. Data was compared to the control (PBS) treatment. Results are presented as mean±SD. $*p<0.005$.

FIG. 4A is a graph showing HMECs infected with retrovirus expressing miR-105 or vector analyzed for ZO-1 expression by RT-qPCR using 18S rRNA as internal control. FIG. 4B is a graph showing HMECs with or without a prior transfection with miR-105 hairpin inhibitor treated with exosomes for 48 hours and analyzed for the RNA level of ZO-1. FIG. 4C is a gel image showing HMECs treated as indicated and analyzed by Western blot. FIG. 4D are images showing HMECs transduced with miR-105 or vector grown on 0.4-μm filters to reach confluence and analyzed by immunofluorescence (IF) for ZO-1 and E-cadherin. DAPI was used for cell nuclei. FIG. 4E are images showing HMECs treated as indicated grown to confluence on filters and analyzed by IF. FIG. 4F is a graph showing HMECs treated as indicated grown to confluence on 0.4-μm filters and analyzed for transepithelial electrical resistance (TEER) as described in Example 1 below. Calculated unit area resistance from triplicate wells was indicated. FIG. 4G is a graph showing HMECs transfected with control RNA or miR-105 mimic with or without a co-transfected ZO-1 expressing plasmid, as well as those treated with MDA-MB-231 exosomes with or without transfection of a miR-105 inhibitor or ZO-1 plasmid, subjected to transwell migration. Cells that had migrated within 16 hours were quantified from triplicate wells. FIG. 4H is a graph showing HMECs pretreated as indicated allowed to reach confluence for 3 days on 3-μm filters before GFP-labeled MDA-231-HM cells were seeded in the transwell inserts. After 10 hours, the GFP+ cells on the bottom side of filters were quantified under a fluorescent microscope. $*p<0.005$.

FIG. 5A is a graph showing HMVECs transduced with miR-105 or vector analyzed for the RNA level of ZO-1 by RT-qPCR. FIG. 5B is a graph showing HMVECs treated as indicated analyzed for the RNA level of ZO-1. FIG. 5C is a gel image showing HMVECs treated as indicated analyzed by Western blot for the protein level of ZO-1. FIG. 5D are images showing HMVECs treated with exosomes or transfected as indicated analyzed for tube formation on Matrigel. Images were taken 4 hours after seeding. FIG. 5E is a graph showing the permeability of treated HMVEC monolayers grown on 0.4-μm filters measured by the appearance of rhodamine-dextran, which was added to the top well at the beginning of the experiment, in the bottom well during a 1 hour time course. The absorbance at 590 nm at each time point was indicated. Treatment of the HMVEC monolayer with VEGF (50 ng/ml) for 8 hours was included as a positive control to show cytokine-induced permeability. FIG. 5F is a graph showing HMVECs treated as indicated subjected to transwell migration and cells that had migrated within 8 hours were quantified. FIG. 5G is a graph showing quantification of invasion of GFP-labeled MDA-231-HM cells through the HMVEC monolayers that were treated as indicated. $*p<0.005$. FIG. 5H is a graph showing TEER analysis of HMVEC monolayers grown on filters and treated as indicated. Calculated unit area resistance from triplicate wells was normalized to the control (PBS) treatment. FIG. 5I are images and a graph showing treatment with miR-105-containing exosomes resulted in a vascular destruction. Vascular sprouting assay was established for 5 days, at which time 1 μg of purified exosomes from MCF10A/vec (control) or MCF10A/miR-105 cells were added into the culture media. Vascular structures were imaged 5 days after the treatment, and representative images were shown (left panel). Vascular sprouts per spheroid were counted and graphed (right panel). At least 50 spheroids were counted in each experiment and the experiment was repeated three times. $*p<0.05$.

FIG. 6A are images of mice showing luciferase-labeled MCFDCIS/vec or MCFDCIS/miR-105 cells injected into the No. 4 mammary fat pad of NSG mice (N=8). Bioluminescence (BLI) at week 6 was shown. Organs carrying metastases that were confirmed by histology were indicated. *Due to the extensive tumor burden these 3 mice were sacrificed at week 5.5 and no metastases were detected; their images at week 5 were shown. FIG. 6B is a graph showing tumor volume determined in the two groups did not show significant difference. FIG. 6C are representative H&E images of the tumor edges showing local invasiveness. Bar=50 μm. FIG. 6D are images showing in vivo vascular permeability determined by the appearance of intravenously injected rhodamine-dextran in various organs. Tissues were collected from mice bearing MCFDCIS/vec or MCFDCIS/miR-105 xenografts (N=3) that were sacrificed at week 6. Representative images are shown. DAPI was used for cell nuclei. Bar=100 μm. FIG. 6E are representative images of miR-105 ISH in tissues collected from the two groups. Bar=50 μm. FIG. 6F are images showing collected tissues subjected to double-label IF for ZO-1 and CD31 or EpCAM. Structures positive for CD31 or EpCAM are indicated by arrowheads. Bar=100 μm. FIG. 6G is a graph showing quantification of metastases in lung and brain. Mice shown in A were sacrificed at week 6 and tissues were subjected to RT-qPCR of luciferase gene using mouse 18S as internal control (n=8). Results are presented as mean±SD.

FIG. 7A are images showing luciferase-labeled MDA-231-HM cells injected into the No. 4 mammary fat pad of NSG mice. Mice were divided into 3 groups (N=6) for treatment with PBS, anti-miR-105 compound, or control compound. BLI at week 3 and week 6 were shown. Organs carrying metastases that were confirmed by histology were indicated in the week 6 images. FIG. 7B is a graph showing tumor volume determined in the 3 groups. $*p<0.005$ comparing to the other 2 groups. FIG. 7C are representative H&E images of the tumor edges showing local invasiveness. Bar=50 μm. FIG. 7D are images of immunohistochemistry performed in xenograft tumors using antibodies of Ki-67, cleaved caspase-3 and ZO-1. Representative images are shown. Bar=50 μm. FIG. 7E are images showing in vivo vascular permeability indicated by the penetration of rhodamine-dextran into various organs. Tissues were collected from tumor-free NSG mice as well as mice bearing MDA-231-HM tumors that were untreated when sacrificed at week 3 after tumor cell implantation (the pre-metastatic group) or treated as indicated and sacrificed at week 6 (N=4). Representative images are shown. DAPI was used for cell nuclei. Bar=100 μm. FIG. 7F are images showing tissues subjected to double-label IF for ZO-1 and CD31. Structures positive for CD31 are indicated by arrowheads. Bar=100 μm. FIG. 7G is a graph showing quantification of metastases in lung and brain. Mice shown in A were sacrificed at week 6 and tissues were subjected to RT-qPCR of luciferase gene using mouse 18S as internal control (n=6). $*p<0.01$. FIG. 7H is a gel image showing MDA-231-HM cells transfected with an anti-miR-105 compound or control compound analyzed by Western blot. FIG. 7I is a graph showing transfected MDA-231-HM cells subjected to transwell migration assays. Cells that had migrated within 8 hours were quantified from triplicate wells. FIG. 7J is a graph showing quantified data of in vivo vascular permeability assays in FIG. 7E (n=4). Levels of rhodamine-dextran fluorescence in tissues were quantified using ImagePro 6.3 software and normalized to levels of DAPI. Results are presented as mean±SD. $*p<0.005$.

FIGS. 8A, 8B, 8C, 8D, 8E, 8F, 8G, and 8H show miR-105 is associated with ZO-1 expression and metastatic progression in breast cancer. FIG. 8A is a graph showing the miR-105 level in the sera of tumor-free or MDA-231-HM tumor-bearing mice (Pre-metastasis: serum collected at week 3; Metastasis: serum collected at week 6; N=5-6) measured by RT-qPCR and normalized to miR-16. FIG. 8B is a graph showing serum miR-105 measured by RT-qPCR, normalized to miR-16, and compared among stage II-III BC patients who developed distant metastases during the follow up (N=17) and those who did not (N=27). FIG. 8C is a table showing correlation analyses of ISH-determined tumor miR-105 level, PCR-determined serum miR-105 level, and IHC-determined ZO-1 level in the tumor or tumor-adjacent vascular structures in breast cancer (BC) patients. FIG. 8D is a table showing mean and SD of miR-105 and ZO-1 staining in patients who developed distant metastases (N=10) and those who did not (N=10). p values are calculated by Student t tests. FIG. 8E are representative images of miR-105 and ZO-1 staining in the tumor. Vascular structures are indicated by arrowheads. Bar=100 μm. FIG. 8F is a schematic showing the proposed dual role of miR-105 in regulating cancer cell invasion and adapting the cancer niche (through regulating the barrier function of epithelial and endothelial cells) to promote metastasis. FIG. 8G is a graph showing levels of tumor miR-105 and ZO-1 determined in a BC tissue array. The in situ hybridization (ISH) or immunohistochemistry (IHC) scores were compared between primary tumors with distant or lymph node metastases (n=15) and those without (n=60). The correlation between miR-105 and ZO-1 was analyzed among all cases (n=75). Results are presented as mean±SD. FIG. 8H is a graph showing miRNA levels in the sera of tumor-free or MDA-231-HM tumor-bearing mice (Pre-metastasis:serum collected at week 3; Metastasis: serum collected at week 6; n=5-6) were measured by RT-qPCR and normalized to miR-16. $p>0.05$. FIG. 8I is a graph showing circulating exosomes isolated from serum samples of stage II-III BC patients. MiRNAs were measured by RT-qPCR, normalized to miR-16, and compared among patients who developed distant metastases during the follow up (n=16) and those who did not (n=22). $p>0.05$. FIG. 8J are images and a graph showing circulating miR-105 in patient serum resulted in a vascular destruction. Vascular structures established from HMVECs that were transfected with anti-miR-105 compound or control compound were treated with human serum from a healthy donor or a BC patient with a high level of circulating miR-105. Representative images of the treated vascular structures were shown (left panel). Inset: structures were stained with CD31 antibody and DAPI. Vascular sprouts per spheroid were counted and graphed (right panel). At least 50 spheroids were counted in each experiment and the experiment was repeated three times. $*p<0.05$. FIG. 8K is a graph showing circulating miR-105 predominantly exists in exosomes. Exosomes isolated from two cases of BC patient sera as well as the corresponding exosome-depleted serum fractions were subjected to RNA extraction and RT-qPCR of selected miRNAs. The ratio of miRNA level in the exosomes to that in exosome-free fraction was shown. Results are presented as mean±SD.

FIG. 9 are phase contrast images showing exosome uptake by HMECs. Primary HMECs were incubated with DiI-labeled exosomes for 24 hours before fluorescent and phase contrast image capture.

FIG. 10 are graphs showing the composition of small RNA sequences in MDA-MB-231 and MCF-10A derived exosomes. Total sequence reads obtained from deep sequencing were aligned to human genome database NCBI36/hg18. The percentage of each class of small RNAs was indicated in the pie chart. scRNA: small cytoplasmic RNA; snRNA: small nuclear RNA; snoRNA: small nucleolar RNA; mt-tRNA: mitochondrial tRNA.

FIGS. 11A, 11B, 11C, and 11D are graphs showing pri- and pre-miR-105 are undetectable in exosomes. Cellular and exosomal RNA of MCF-10A and MDA-MB-231 were subjected to RT-qPCR for pri-miR-105 (FIG. 11A) or pre-miR-105 (FIG. 11B). $*p<0.005$. RNA extracted from HMVECs or HMECs incubated with exosomes of different origins for 24 hours was analyzed for the level of pri-miR-105 (FIG. 11C) or pre-miR-105 (FIG. 11D).

FIGS. 13A, 13B, 13C, and 13D show miR-105 overexpression in metastatic BC cells promotes metastasis. FIG. 13A is a graph showing MCFDCIS cells stably transduced with miR-105 or vector analyzed for miR-105 expression and secretion by RT-qPCR. Data was normalized to levels of U6 (for cellular miR-105) or miR-16 (for exosomal miR-105). FIG. 13B is a gel image showing transduced MCFD-CIS cells with or without transfection with a ZO-1 expression plasmid or vector control analyzed by Western blot at 48 hours post transfection. FIG. 13C is a graph showing the indicated cells subjected to transwell migration assay and cells that had migrated within 8 hours were quantified from triplicate wells. FIG. 13D are images showing miR-105 induces MCFDCIS cell migration during wound closure. Confluent monolayers of MCFDCIS cells transduced and transfected as in FIGS. 3C and 3D were wounded with a pipette tip. Wound closure was monitored at the indicated time points.

FIGS. 14A, 14B, and 14 C show miR-105-transduced MCF-10A cells express and secrete high level of miR-105. FIG. 14A is a graph showing MCF-10A cells stably transduced with miR-105 or vector analyzed for miR-105 expression and secretion by RT-qPCR as in FIGS. 2A and 2B. FIG. 14B is a gel image showing transduced cells analyzed by Western blot for ZO-1 expression. FIG. 14C is a graph showing cells subjected to transwell migration assay and those migrated within 24 h were quantified from triplicate wells. *p<0.005.

FIGS. 15A and 15B are graphs showing the effect of exosomes of various origins on ZO-1 expression in HMECs and HMVECs. Exosomes derived from indicated cell lines were added to (FIG. 15A) HMECs or (FIG. 15B) HMVECs. At 48 hours after exosome treatment, RNA was extracted from the recipient cells and subjected to miR-105 and ZO-1 RT-qPCR using U6 and 18S as the corresponding internal reference. Data was compared to the control (PBS) treatment. *p<0.005.

FIGS. 16A and 16B show growth of MCFDCIS xenograft tumors. FIG. 16A are images showing week 3 BLI of mice bearing MCFDCIS xenograft tumors. The week 6 (premetastatic stage) BLI of mice shown in FIG. 6 (N=8). FIG. 16B is a graph showing tumor volume determined in the two groups of mice did not show significant difference (n=8).

FIG. 17A are representative images of in vivo vascular permeability was determined in MCFDCIS xenograft tumors (N=3). No significant difference is observed between the two groups. Bar=100 μm. FIG. 17B is a graph showing quantified data of the in vivo vascular permeability assays. Levels of rhodamine-dextrans fluorescence in tissues were quantified using ImagePro 6.3 software and normalized to the levels of DAPI. *p<0.005 compared to white columns (controls). Results are presented as mean±SD.

FIG. 19A is an image of unsupervised hierarchical clustering over all detected miRNAs. The heatmap represent a sample's higher or lower level in relation to the mean of all samples. FIG. 19B is a graph os the top 100 miRNAs with the highest quantities in circulation. For each miRNA shown, the range of normalized counts was indicated by a column, and the mean value was indicated by a line.

FIG. 20A is a graph showing miR-105 levels. Exosomes secreted by MCF10A/vec, MCF10A/miR-105, or MDA-MB-231 cells, or PBS (as control), were intravenously injected into the tail vein of NSG mice (n=3) twice a week. After 5 injections, tissues were collected for RT-qPCR of miR-105 using U6 as internal control. *p<0.05. FIG. 20B is a graph showing relative luciferase levels. Exosomes secreted by MCF-10A or MDA-MB-231 cells, or PBS (as control), were intravenously injected into the tail vein of NSG mice (n=6) twice a week. After 5 injections, all mice received intracardiac injection of luciferase-labeled MDA-MB-231 cells. Three weeks later, tissues were collected for RT-qPCR of luciferase gene using mouse 18S as internal control to quantify metastases. *p<0.05. Results are presented as mean±SD. FIG. 20C is a graph showing quantified data of the in vivo vascular permeability assay (n=3). Levels of rhodamine-dextran fluorescence in tissues were quantified using ImagePro 6.3 software and normalized to the levels of DAPI. Results are presented as mean±SD. *p<0.005 compared to the white columns (controls).

FIG. 23A) or U6 (cellular; FIG. 23B), and compared to the nontumour line MCF10A. *p<0.05.

FIGS. 24A, 24B, 24C, 24D, 24E, 24F, 24G, 24H, 24I, 24J, 24K and 24L show miR-122 suppresses glucose metabolism by down-regulating PKM. FIG. 24A is a graph showing BrdU uptake in MCF10A/miR-122 cells after 1 hour of incubation were analysed by flow cytometry. FIG. 24B is a graph showing quantification of intracellular metabolites by NMR spectroscopy from triplicate samples. Normalized levels were compared in 5×106 cells per sample. FIG. 24C is a graph showing change of metabolites in the media after 72 hours of culture. FIG. 24D shows the predicted miR-122 binding sites in the 3'UTR of human PKM and CS genes. The corresponding sequences in the mutated (mt) versions are also shown. FIG. 24E is a graph showing the psiCHECK reporters containing indicated wild-type (wt) or mutated (mt) miR-122 binding site in the 3'UTR of human PKM2 or CS cDNA were used to transfect MCF10A cells stably expressing miR-122 or the retroviral vector (as control). Luciferase activity was analyzed at 48 hours post-transfection. *p<0.05. FIG. 24F is a graphs showing RT-qPCR analysis showing the relative expression of indicated genes in MCF10A/miR-122 and MCF10A/vec cells. *p<0.05. FIG. 24G is a gel image of a Western blot analysis in MCF10A/miR-122 and MCF10A/vec cells. FIG. 24H is a graph showing PKM activity (unit) in 5 µg proteins. FIG. 24I is a graph showing PKM activity (unit) in 5 µg proteins in selected colonies. FIG. 24J is a gel image showing change of glucose in the media after 72 hours of culture in selected colonies. FIG. 24K is a graph showing PKM activity (unit) in 5 µg proteins. FIG. 24L is a graph showing the change of glucose in the media after 72 hours of culture. Data are represented as mean±SD in all panels except FIGS. 24D and 24G.

FIGS. 25A, 25B, 25C, 25D, 25E, 25F, and 25G show exosomal miR-122 down-regulates glucose uptake in lung fibroblasts. Primary mouse lung fibroblasts were treated with two doses of exosomes from indicated producer cells given 48 hours apart, before subjected to RT-qPCR at 96 hours for miR-122, PKM2, and CS (FIG. 25A), Western blot analysis (FIG. 25B), and PKM activity assay using 5 µg of proteins (FIG. 25C). FIG. 25D is a graph showing quantitation of 2-NBDG uptake. After receiving two feedings of exosomes, the fibroblasts were treated with 2-NBDG for 40 minutes and fluorescence intensity quantified by a fluorometer. FIG. 25E is a gel image of Western blot analysis to determine the efficiency of siRNA transfection against PKM2 or GLUT1. FIG. 25F is a graph showing 2-NBDG uptake in siRNA transfected fibroblasts. FIG. 25G is a graph showing media glucose analysis of MDA-MB-231-HM cells co-cultured with siRNA transfected fibroblasts for 72 hours. Data are represented as mean±SD in all panels except FIG. 25B.

FIGS. 26A, 26B, 26C, 26D, 26E, 26F, and 26G show exosomal transfer of miR-122 alters niche tissue glucose uptake. Indicated exosomes were intravenously injected into the tail vein of NSG mice biweekly for 3.5 weeks. FIG. 26A are images of coimmunofluorescence of neuron marker MAP2, exosome marker CD63 (detected by a human-specific antibody), and fibroblast marker FSP-1 in brain and lung tissues of mice injected with 2-NBDG. Nuclei were counterstained with DAPI. White bar represents 20 µm. FIG. 26B is a graph showing quantification of 2-NBDG uptake in brain from 5 fields per mouse (N=3). FIG. 26C is a graph showing quantification of 2-NBDG uptake in lung from 5 fields per mouse (N=3). FIGS. 26D and 26E are graphs showing RTqPCR in brain (FIG. 26D) and lung (FIG. 26E). FIGS. 26F and 26G are graphs showing luciferase DNA qPCR for the detection of metastases in the brain (FIG. 26F) and lung (FIG. 26G) of mice pre-treated with exosomes then injected intracardiac with luciferase-labelled MDA-MB-231-HM tumour cells. Data are represented as mean±SD for FIGS. 26B, 26C, 26D, 26E, 26F, and 26G.

FIGS. 27A, 27B, 27C, 27D, 27E, 27F, 27G, 27H, and 27I show miR-122 over expression reduces tumour growth and enhances metastasis. FIG. 27A is a graph showing tumor growth curve in DCIS/pGABE and DCIS/miR-122 tumour bearing mice. FIG. 27B are images showing bioluminescence (BLI) imaging at week 3. FIG. 27C is a graph showing luciferase quantification of (FIG. 27B) using Living Imaging Software. FIG. 27D are images showing IHC for Ki67, PKM2, and GLUT1 in tumour, brain, and lung sections. Scale bar is 100 µm. FIG. 27E is a graph showing quantification of Ki67 positive tumour cells from 3 fields (N=3 per group). FIG. 27F is a graph showing miR-122 expression in the lung and brain determined by RT-qPCR. FIG. 27G is a graphs showing 2-NBDG uptake quantification in the tumour, brain, and lung from 3 fields (N=4 per group). FIGS. 27H and 27I are graphs showing luciferase DNA qPCR in the brain (FIG. 27H, N=8 per group) and lung (FIG. 27I, N=5-6 per group) of DCIS tumour bearing mice with corresponding BLI image next to symbol. Data are represented as mean±SD in all panels except FIGS. 27B and 27D.

FIGS. 28A, 28B, 28C, 28D, 28E, 28F, 28G, 28H, 28I, and 28J show miR-122 intervention alleviates cancer-induced glucose reallocation in vivo and reduces metastasis. Luciferase-labelled MDA-MB-231-HM cells were injected into the No. 4 mammary fat pad of NSG mice. Mice were divided into 3 groups (N=8) for treatment with PBS, anti-miR-122, or mismatch control oligos. FIG. 28A is a graph showing tumor growth curve. FIG. 28B is a graph showing 2-NBDG uptake in the tumour and tumour-adjacent stroma. FIG. 28C is a graph showing quantification of BLI at week 5 (FIG. 28D). FIG. 28D are images of BLI at week 5 indicating extensive brain and lung metastases in PBS and mismatch groups and reduced incidence of metastasis in anti-miR-122 group. FIGS. 28E, and 28F are graphs showing quantification of 2-NBDG uptake in the brain (FIG. 28E) and lung (FIG. 28F) of tumour-free (normal) NSG mice and tumour bearing mice that were untreated when sacrificed at week 3 after tumour cell implantation (the pre-metastatic group) or treated as indicated and sacrificed at week 6 (N=4). FIG. 28G are representative images of 2-NBDG uptake fluorescence. White bar represents 100 µm. FIGS. 28H and 28I are graphs showing RT-qPCR in brain (FIG. 28H) and in lung (FIG. 28I) of tumour-free NSG mice and tumour bearing mice (N=4). FIG. 28J are images of GLUT1 IHC in brain and lung of NSG mice. Data are represented as mean±SD in all panels except FIGS. 28D, 28G and 28J.

FIGS. 29A, 29B, 29C, 29D and 29E show clinical correlation of miR-122 and PKM2. FIG. 29A is a graph showing the miR-122 levels in the serum of tumour-free mice and mice bearing MDA-MB-231-HM or MCFDCIS tumour for 3 weeks (N=5-6) measured by RT-qPCR and normalized to miR-16. Data are represented as mean±SD. FIG. 29B is a graph showing correlation analysis between ISH-determined tumour miR-122 level and PCR determined serum miR-122 level in stage II-III BC patients (N=11). FIG. 29C is a graph of RT-qPCR analysis for miR-122. Pooled normal or BC patient serum were fractioned into an exosome-rich fraction and exosome-free fraction using Total Exosome Isolation kit (Life Technologies, Carlsbad, Calif.). RNA was extracted from the two fractions and subjected to RT-qPCR for miR-122. Data are compared to the first column (exosome-depleted normal serum) and represented as mean±SD. FIG. 29D is a graph showing correlation analysis between ISH-determined miR-122 level and IHC-determined PKM2 level in human breast tumours (N=70). FIG. 29E are representative images from 3 cases are shown for inversely correlated levels of miR-122 and PKM2 in the tumour. Bar represents 100 µm.

FIGS. 30A and 30B show increased miR-122 secretion by MCF10A cells over expressing miR-122. FIG. 30A is a graph showing MCF10A/miR-122 and MCF10A/vec cells analyzed for intracellular and exosomal miR-122 levels by RT-qPCR. FIG. 30B are images of glycogen staining in MCF10A/vec and MCF10A/miR-122 cells. Staining was performed using a PAS kit. Bar equals 100 µm.

FIGS. 31A and 31B are gel images showing determination of PKM isoforms expressed in cells used in this study.

For FIG. 31A, RNA extracted from indicated human cells, mouse lung fibroblasts, and astrocytes was subjected to RT-PCR as in (Clower et al., PNAS, 107:1894-9 (2010)) followed by digestion with NcoI (N), PstI (P), or both enzymes (NP), plus an uncut control (U). Products were separated on an agarose gel with Sybr safe. The presence of a PstI digestion site indicates the splicing isoform M2 whereas the NcoI site indicates isoform M1. All cells tested are found to express the isoform M2. For FIG. 31B, RNA extracted from non-tumour bearing mouse brain and lung and subjected to RT-PCR and enzymatic digestion as in FIG. 31A, indicating that M1 is the major isoform in brain whereas isoform M2 is expressed in lung.

FIGS. 32A, 32B, 32C, and 32D show exosomal miR-122 down-regulates glucose uptake in astrocytes. Primary mouse astrocytes were treated with two doses of exosomes from indicated producer cells given 48 hours apart, before subjected to RT-qPCR at 72 hours for miR-122 (FIG. 32A), Western blot analysis for PKM2 and GLUT1 at 96 hours (FIG. 32B), and PKM activity assay using 10 μg of proteins (FIG. 32C). FIG. 32D is a graph of 2-NBDG uptake in astrocytes after received two feedings of exosomes given 48 hours apart and fluorescence intensity quantified by a fluorometer. Data are represented as mean±SD in all panels except FIG. 32B.

Figure 33A:
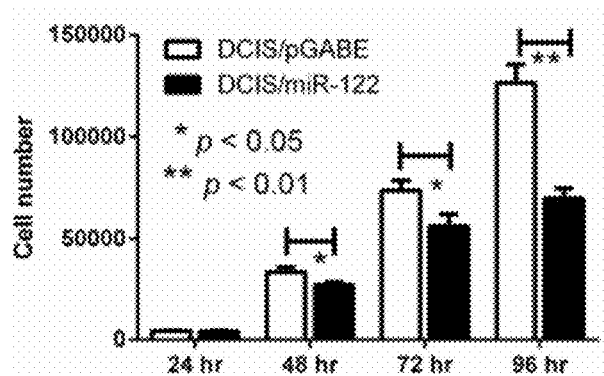
Figure 33B:
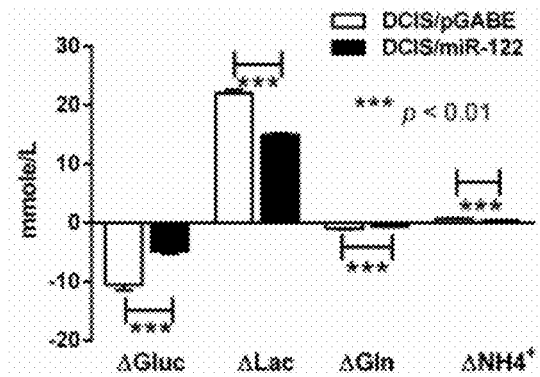
Figure 33C:
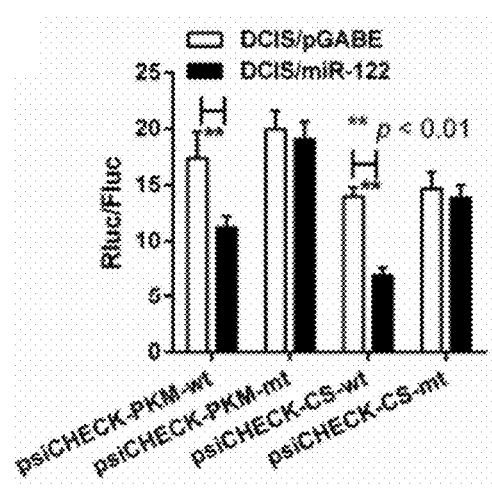
Figure 33D:
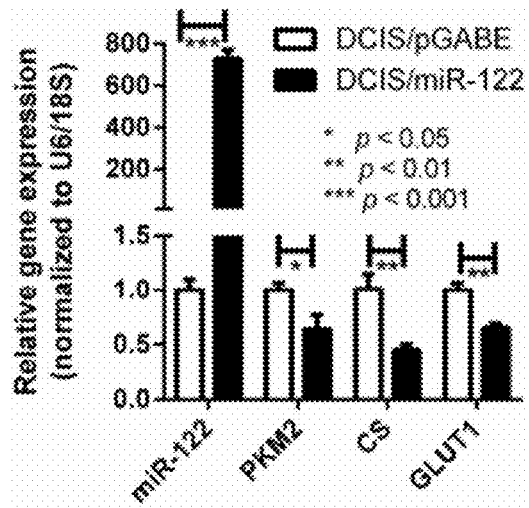
Figure 33E:
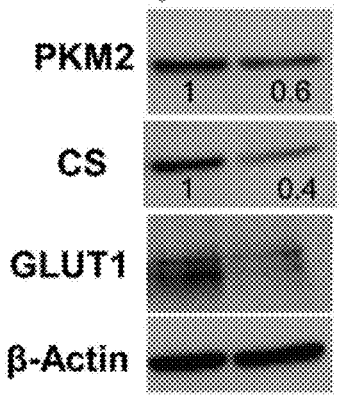

FIGS. 33A, 33B, 33C, 33D and 33E, show the effect of miR-122 in DCIS cells. FIG. 33A is a graph of the cell number count of DCIS/miR-122 and DCIS/pGABE cells at indicated time points. FIG. 33B is a graph of the media metabolite analysis after 48 hours of culture. FIG. 33C is a graph of luciferase activity. The psiCHECK reporters containing indicated wild-type (wt) or mutated (mt) miR-122 binding site in the 3'UTR of human PKM2 or CS cDNA were used to transfect DCIS cells stably expressing miR-122 or the retroviral vector (as control). Luciferase activity was analyzed at 48 hours post-transfection. FIG. 33D is a graph of RT-qPCR analysis showing the relative expression of indicated genes in DCIS/miR-122 and DCIS/pGABE cells. FIG. 33E is an image of Western blot analysis in DCIS/miR-122 and DCIS/pGABE cells.

Figure 34A:
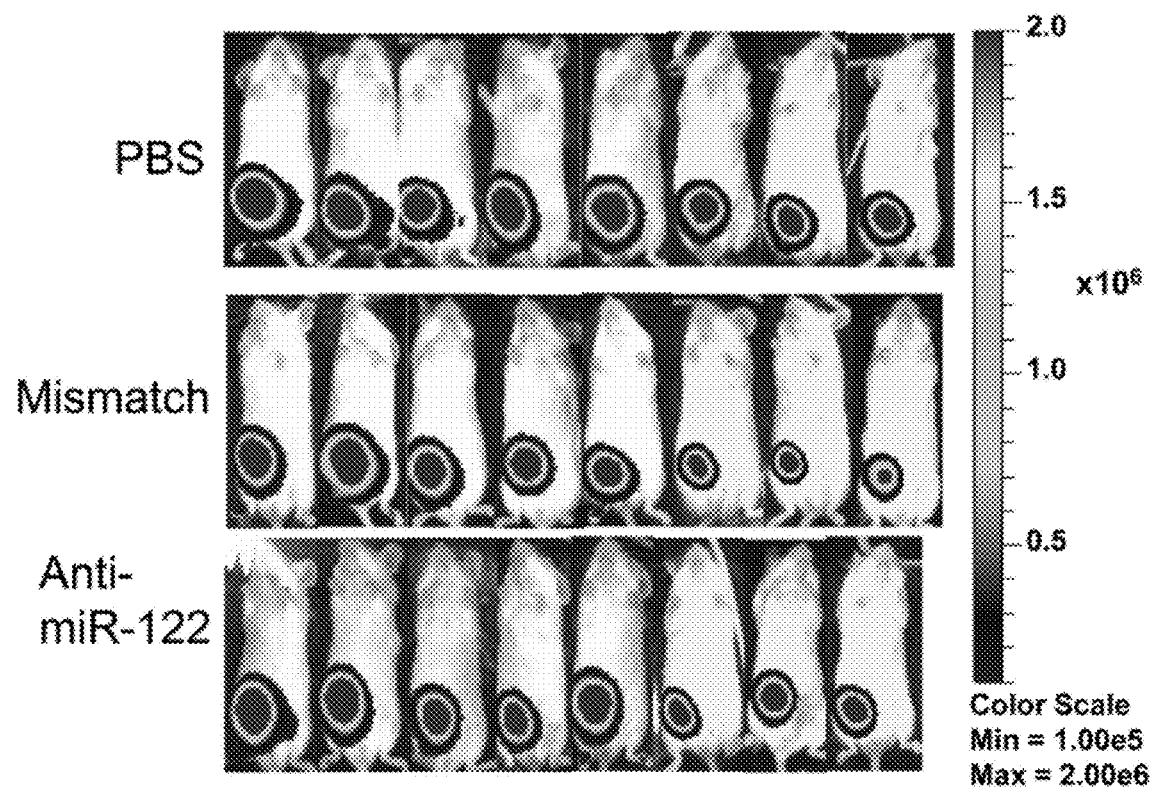
Figure 34B:
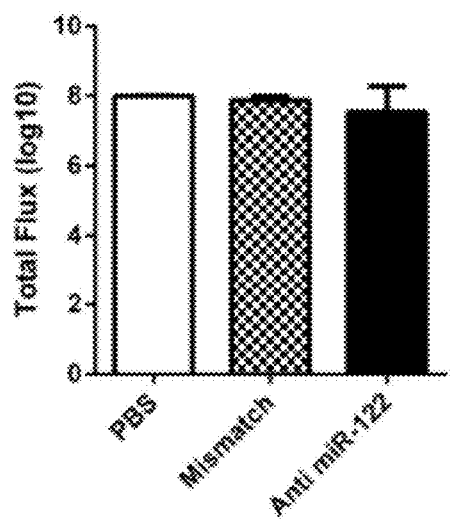
Figure 34C:
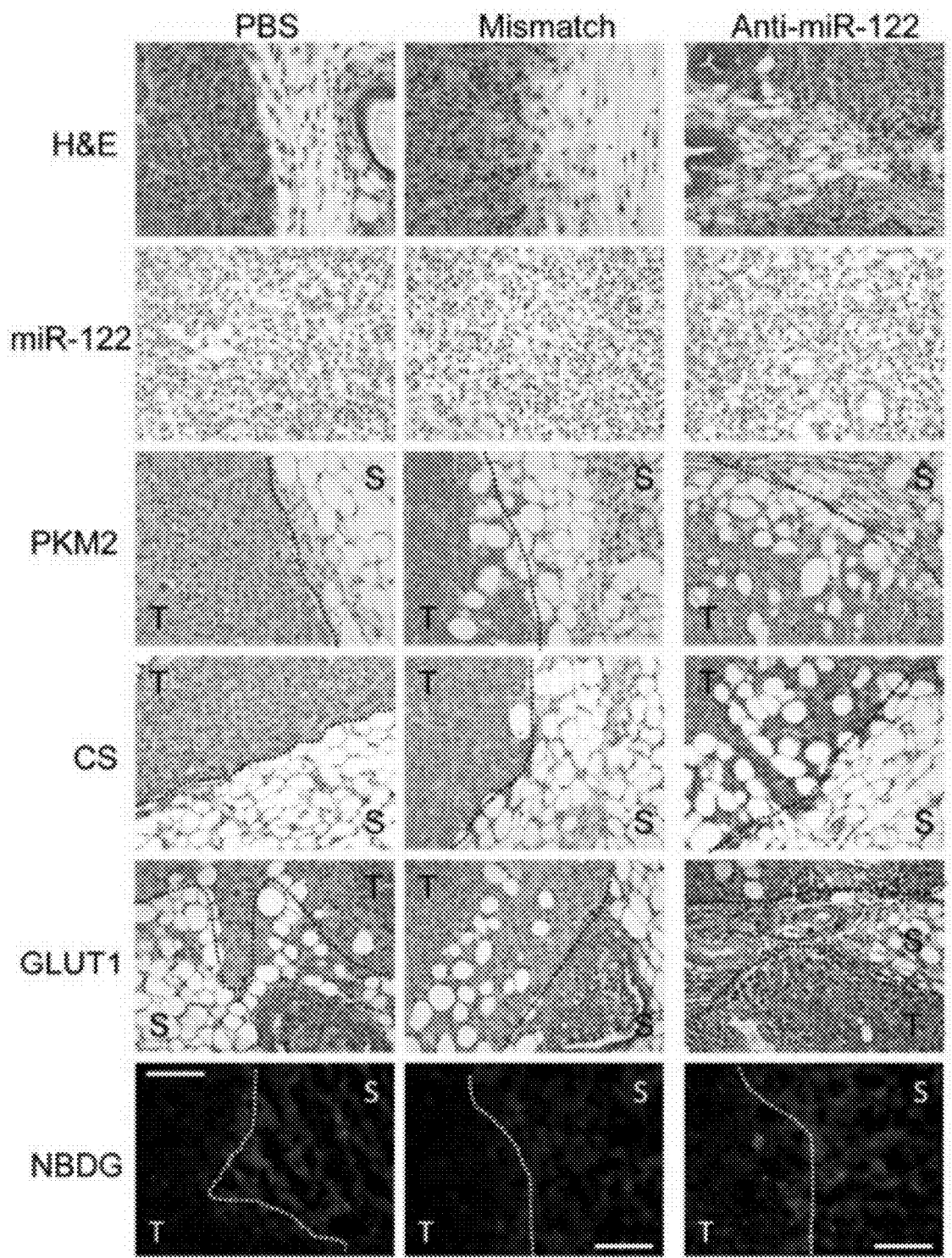

FIGS. 34A, 34B and 34C show primary tumours established with MDA-MB-231-HM and treated with anti-miR-122 oligos. FIG. 34A are images of BLI imaging at week 3. FIG. 34B is a graph of the quantification of FIG. 34A using Living Image Software. FIG. 34C are images of primary tumor sections analyzed by IHC (for PKM2, CS, and GLUT1) and ISH (for miR-122). For 2-NBDG uptake, sections were counterstained with DAPI to show nuclei. Dotted line delineates tumor (T) from stroma (S). White bar equals 500 μm.

DETAILED DESCRIPTION

Definitions

The terms "subject," "patient," "individual," etc. are not intended to be limiting and can be generally interchanged. That is, an individual described as a "patient" does not necessarily have a given disease, but may be merely seeking medical advice.

A "control" or "standard control" refers to a sample, measurement, or value that serves as a reference, usually a known reference, for comparison to a test sample, measurement, or value. For example, a test sample can be taken from a patient suspected of having a given disease (e.g. an autoimmune disease, inflammatory autoimmune disease, cancer, infectious disease, immune disease, or other disease) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. One of skill will recognize that standard controls can be designed for assessment of any number of parameters (e.g. RNA levels, protein levels, specific cell types, specific bodily fluids, specific tissues, synoviocytes, synovial fluid, synovial tissue, fibroblast-like synoviocytes, macrophage-like synoviocytes, etc).

One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

The terms "dose" and "dosage" are used interchangeably herein. A dose refers to the amount of active ingredient given to an individual at each administration. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical or pharmaceutical composition, and depends on the route of administration. For example, a dosage form can be in a liquid form for nebulization, e.g., for inhalants, in a tablet or liquid, e.g., for oral delivery, or a saline solution, e.g., for injection.

As used herein, the terms "treat" and "prevent" may refer to any delay in onset, reduction in the frequency or severity of symptoms, amelioration of symptoms, improvement in patient comfort or function (e.g. joint function), decrease in severity of the disease state, etc. The effect of treatment can be compared to an individual or pool of individuals not receiving a given treatment, or to the same patient prior to, or after cessation of, treatment. The term "prevent" generally refers to a decrease in the occurrence of a given disease (e.g. an autoimmune, inflammatory, cancer, infectious, metabolic, developmental, cardiovascular, liver, intestinal, endocrine, neurological, or other disease) or disease symptoms in a patient. As indicated above, the prevention may be complete (no detectable symptoms) or partial, such that fewer symptoms are observed than would likely occur absent treatment.

By "therapeutically effective dose or amount" as used herein is meant a dose that produces effects for which it is administered (e.g. treating or preventing a disease). The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)). For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a standard control. A therapeutically effective dose or amount may ameliorate one or more symptoms of a disease. A therapeutically effective dose or amount may prevent or delay the onset of a disease or one or more symptoms of a disease when the effect for which it is being administered is to treat a person who is at risk of developing the disease.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. In certain embodiments. the nucleic acids herein contain phosphodiester bonds. In other embodiments, nucleic acid analogs are included that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and nonribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

Nucleic acids are linear polymers (chains) of nucleotides, which consist of a purine or pyrimidine nucleobase or base, a pentose sugar, and a phosphate group. As used herein, a "polymer backbone" refers to the chain of pentose sugars and phosphate groups lacking the bases normally present in a nucleic acid.

Nucleic acids can include nonspecific sequences. As used herein, the term "nonspecific sequence" refers to a nucleic acid sequence that contains a series of residues that are not complementary to or are only partially complementary to any other nucleic acid sequence. By way of example, a nonspecific nucleic acid sequence is incapable of hybridizing to any other nucleic acid sequence under hybridizable conditions. Optionally, a nonspecific nucleic acid sequences is a sequence that is not substantially identical to any other nucleic acid sequence. By way of another example, a nonspecific nucleic acid sequence is a sequence of nucleic acid residues that does not function as an inhibitory nucleic acid. An "inhibitory nucleic acid" is a nucleic acid (e.g. DNA, RNA, polymer of nucleotide analogs) that is capable of binding to a target nucleic acid (e.g. an mRNA translatable into a protein) and reducing transcription of the target nucleic acid (e.g. mRNA from DNA) or reducing the translation of the target nucleic acid (e.g. mRNA) or altering transcript splicing (e.g. single stranded morpholino oligo).

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., J. Biol. Chem. 273(52):35095-35101 (1998).

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "probe" or "primer", as used herein, is defined to be one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767-773; Johnston (1998) Curr. Biol. 8: R171-R174; Schummer (1997) Biotechniques 23: 1087-1092; Kern (1997) Biotechniques 23: 120-124; U.S. Pat. No. 5,143,854).

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe. Alternatively, a method using high affinity interactions may achieve the same results where one of a pair of binding partners binds to the other, e.g., biotin, streptavidin.

The terms "identical" or percent sequence "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site at ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. Employed algorithms can account for gaps and the like.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are wellknown in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively.

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA).

The phrase "stringent hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent hybridization conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent hybridization conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al., John Wiley & Sons.

Nucleic acids may be substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions.

An "inhibitory nucleic acid" is a nucleic acid (e.g. DNA, RNA, polymer of nucleotide analogs) that is capable of binding to a target nucleic acid (e.g. an mRNA translatable into PTPRS) and reducing transcription of the target nucleic acid (e.g. mRNA from DNA) or reducing the translation of the target nucleic acid (e.g. mRNA) or altering transcript splicing (e.g. single stranded morpholino oligo). A "morpholino oligo" may be alternatively referred to as a "morphlino nucleic acid" and refers to morpholine-containing nucleic acid nucleic acids commonly known in the art (e.g. phosphoramidate morpholinio oligo or a "PMO"). See Marcos, P., Biochemical and Biophysical Research Communications 358 (2007) 521-527. In some embodiments, the "inhibitory nucleic acid" is a nucleic acid that is capable of binding (e.g. hybridizing) to a target nucleic acid (e.g. an mRNA translatable into an RPTPS) and reducing translation of the target nucleic acid. The target nucleic acid is or includes one or more target nucleic acid sequences to which the inhibitory nucleic acid binds (e.g. hybridizes). Thus, an inhibitory nucleic acid typically is or includes a sequence (also referred to herein as an "antisense nucleic acid sequence") that is capable of hybridizing to at least a portion of a target nucleic acid at a target nucleic acid sequence, An example of an inhibitory nucleic acid is an antisense nucleic acid. Another example of an inhibitory nucleic acid is siRNA or RNAi (including their derivatives or pre-cursors, such as nucleotide analogs). Further examples include shRNA, miRNA, shmiRNA, or certain of their derivatives or pre-cursors. In some embodiments, the inhibitory nucleic acid is single stranded. In other embodiments, the inhibitory nucleic acid is double stranded.

An "antisense nucleic acid" is a nucleic acid (e.g. DNA, RNA or analogs thereof) that is at least partially complementary to at least a portion of a specific target nucleic acid (e.g. a target nucleic acid sequence), such as an mRNA molecule (e.g. a target mRNA molecule) (see, e.g., Weintraub, Scientific American, 262:40 (1990)), for example antisense, siRNA, shRNA, shmiRNA, miRNA (microRNA). Thus, antisense nucleic acids are capable of hybridizing to (e.g. selectively hybridizing to) a target nucleic acid (e.g. target mRNA). In some embodiments, the antisense nucleic acid hybridizes to the target nucleic acid sequence (e.g. mRNA) under stringent hybridization conditions. In some embodiments, the antisense nucleic acid hybridizes to the target nucleic acid (e.g. mRNA) under moderately stringent hybridization conditions. Antisense nucleic acids may comprise naturally occurring nucleotides or modified nucleotides such as, e.g., phosphorothioate, methylphosphonate, and -anomeric sugar-phosphate, backbonemodified nucleotides. An "anti-PTPRS antisense nucleic acid" is an antisense nucleic acid that is at least partially complementary to at least a portion of a target nucleic acid sequence, such as an mRNA molecule, that codes at least a portion of the PTPRS. In some embodiments, an antisense nucleic acid is a morpholino oligo. In some embodiments, a morpholino oligo is a single stranded antisense nucleic acid, as is know in the art. In some embodiments, a morpholino oligo decreases protein expression of a target, reduces translation of the target mRNA, reduces translation initiation of the target mRNA, or modifies transcript splicing. In some embodiments, the morpholino oligo is conjugated to a cell permeable moiety (e.g. peptide). Antisense nucleic acids may be single or double stranded nucleic acids.

In the cell, the antisense nucleic acids may hybridize to the target mRNA, forming a double-stranded molecule. The antisense nucleic acids, interfere with the translation of the mRNA, since the cell will not translate a mRNA that is double-stranded. The use of antisense methods to inhibit the in vitro translation of genes is well known in the art (Marcus-Sakura, Anal. Biochem., 172:289, (1988)). Antisense molecules which bind directly to the DNA may be used.

Inhibitory nucleic acids can be delivered to the subject using any appropriate means known in the art, including by injection, inhalation, or oral ingestion. Another suitable delivery system is a colloidal dispersion system such as, for example, macromolecule complexes, nanocapsules, microspheres, beads, and lipid-based systems including oil-in-water emulsions, micelles, mixed micelles, and liposomes. An example of a colloidal system of this invention is a liposome. Liposomes are artificial membrane vesicles which are useful as delivery vehicles in vitro and in vivo. Nucleic acids, including RNA and DNA within liposomes and be delivered to cells in a biologically active form (Fraley et al., Trends Biochem. Sci., 6:77, 1981). Liposomes can be targeted to specific cell types or tissues using any means known in the art. Inhibitory nucleic acids (e.g. antisense nucleic acids, morpholino oligos) may be delivered to a cell using cell permeable delivery systems (e.g. cell permeable peptides). In some embodiments, inhibitory nucleic acids are delivered to specific cells or tissues using viral vectors or viruses.

An "siRNA" refers to a nucleic acid that forms a double stranded RNA, which double stranded RNA has the ability to reduce or inhibit expression of a gene or target gene when the siRNA is present (e.g. expressed) in the same cell as the gene or target gene. The siRNA is typically about 5 to about 100 nucleotides in length, more typically about 10 to about 50 nucleotides in length, more typically about 15 to about 30 nucleotides in length, most typically about 20-30 base nucleotides, or about 20-25 or about 24-29 nucleotides in length, e.g., 20, 21, 22, 23, 24, 25, 26, 27, 28, 29, or 30 nucleotides in length. siRNA molecules and methods of generating them are described in, e.g., Bass, 2001, Nature, 411, 428-429; Elbashir et al., 2001, Nature, 411, 494-498; WO 00/44895; WO 01/36646; WO 99/32619; WO 00/01846; WO 01/29058; WO 99/07409; and WO 00/44914. A DNA molecule that transcribes dsRNA or siRNA (for instance, as a hairpin duplex) also provides RNAi. DNA molecules for transcribing dsRNA are disclosed in U.S. Pat. No. 6,573,099, and in U.S. Patent Application Publication Nos. 2002/0160393 and 2003/0027783, and Tuschl and Borkhardt, Molecular Interventions, 2:158 (2002).

The siRNA can be administered directly or siRNA expression vectors can be used to induce RNAi that have different design criteria. A vector can have inserted two inverted repeats separated by a short spacer sequence and ending with a string of T's which serve to terminate transcription.

The term "miRNA" refers to a microRNA molecule found in eukaryotes that is involved in gene regulation. See, e.g., Carrington et al., Science 301(5631):336-8 (2003), which is hereby incorporated by reference. Names of miRNAs and their sequences are provided herein.

Construction of suitable vectors containing the nucleic acid sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and re-ligated in the form desired.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, Bioconjugate Techniques 1996, Academic Press, Inc., San Diego.

The term "recombinant" when used with reference, e.g., to a cell, or nucleic acid, protein, or vector, indicates that the cell, nucleic acid, protein or vector has been modified by or is the result of laboratory methods. Thus, for example, recombinant proteins include proteins produced by laboratory methods. Recombinant proteins can include amino acid residues not found within the native (non-recombinant) form of the protein or can be include amino acid residues that have been modified, e.g., labeled.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. In some embodiments, antibodies or fragments of antibodies may be derived from different organisms, including humans, mice, rats, hamsters, camels, etc. Antibodies of the invention may include antibodies that have been modified or mutated at one or more amino acid positions to improve or modulate a desired function of the antibody (e.g. glycosylation, expression, antigen recognition, effector functions, antigen binding, specificity, etc.).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676, 980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816, 567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

Techniques for conjugating therapeutic agents to antibodies are well known (see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)).

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

As used herein, the term "pharmaceutically acceptable" is used synonymously with "physiologically acceptable" and "pharmacologically acceptable". A pharmaceutical composition will generally comprise agents for buffering and preservation in storage, and can include buffers and carriers for appropriate delivery, depending on the route of administration.

As used herein, the term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and Medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

As used herein, "treating" or "treatment of" a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently. As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

As used herein, the term "vascular permeability" refers to the characterization of a blood vessel wall and the blood vessel wall's capacity to allow for the transport of molecules into and out of the blood vessel. The term "increasing vascular permeability" refers to an increase in the capacity of a blood vessel wall to transport one or more molecules into and/or out of a blood vessel. The increase in capacity includes an increase in the number of molecules that are transported into and/or out of a blood vessel through the blood vessel wall. The terms higher, increases, elevates, or elevation refer to increases above a control. For example, control levels are in vitro, ex vivo, or in vivo levels prior to, or in the absence of, addition of an agent. Thus, the increase can be a 10, 20, 30, 40, 50, 60, 70, 80, 90, 100%, or any amount of increase in between as compared to native or control levels.

As used herein, the term "glucose uptake" refers to the ability of a cell to take up or absorb glucose. Cells can take up glucose in an active or passive manner. Passive transport of glucose involves facilitated diffusion of glucose into the cell. Active transport of the molecule involves the active transport of the molecule using a process that indirectly requires the hydrolysis of ATP. A reduction of glucose uptake by a cell refers to the reduction in the amount, whether active or passive, of glucose that is taken up by the cell. Thus, reducing glucose uptake of a cell includes the reduction of uptake of glucose by the cell from the extracellular environment, e.g., from blood vessels or surrounding environment. The term "reducing glucose uptake in a subject" includes a reduction or decrease in the uptake of glucose by the cells of a subject. The terms low, lower, decrease, reduces, or reduction refer to any decrease below control levels. For example, control levels are in vitro, ex vivo, or in vivo levels prior to, or in the absence of, addition of an agent. Thus, the reduction can be a 10, 20, 30, 40, 50, 60, 70, 80, 90, 100%, or any amount of reduction in between as compared to native or control levels.

As used herein, the term "miR-105" includes all forms of miR-105 including the pri-, pre- and mature forms of miR-105 as well as variants, modifications and derivatives thereof. MiR-105 is an miRNA molecule, which are small non-coding RNA molecules functioning in regulation of gene expression. MiRNAs are typically generated from large RNA precursors (termed pri-miRNAs), which are then processed in the nucleus into smaller length RNA molecules, referred to as pre-miRNAs (usually ~70 nucleotides). Pre-miRNA molecules fold into stem-loop or hairpin structures and undergo an additional processing step within the cytoplasm where mature miRNAs of approximately 18 to 25 nucleotides in length are excised from the pre-miRNA hairpin. As used herein, the term miR-105 includes all forms of these miRNA molecules. Exemplary nucleic acid sequences of miR-105 can be found, for example, at GenBank Accession Nos. AF480503, and AF480547 and include UGUGCAUCGUGGUCAAAUGCUCAGACUCCUGUG-GUGGCUGCUCAUGCACCACGGAUGUUUGAGCAU-GUGCUACGGUGUCUA (SEQ ID NO:1). The mature form of miR-105 is residues 13 to 35 of SEQ ID NO:1, which when excised from the pre-miRNA can be excised with residues 51 to 72 of SEQ ID NO:1 when the pre-miRNA is in a stem-loop or hairpin conformation. Thus, the term miR-105 can include these sequences as well as variants, modifications, and derivatives thereof.

As used herein, the term "miR-122" includes all forms of miR-122 including the pri-, pre- and mature forms of miR-122, as well as variants, modifications and derivatives thereof. As discussed above, miRNAs are typically generated from large RNA precursors (termed pri-miRNAs), which are then processed in the nucleus into smaller length RNA molecules, referred to as pre-miRNAs (usually ~70 nucleotides). Pre-miRNA molecules fold into stem-loop or hairpin structures and undergo an additional processing step within the cytoplasm where mature miRNAs of approximately 18 to 25 nucleotides in length are excised from the pre-miRNA hairpin. As used herein, the term miR-122 includes all forms of these miRNA molecules including, but not limited to, the pri-, pre-, and mature forms of miR-122. Exemplary nucleic acid sequences of miR-122 can be found, for example, at GenBank Accession No. NR_029667.1 and include CCUUAGCAGAGCUGUGGAGUGUGACAAU-GGUGUUUGUGUCUAAACUAUCAAACGCCAUUAU-CACACUAAAUAGCUACUGCUAGGC (SEQ ID NO:2). The mature form of miR-122 is residues 15 to 36 of SEQ ID NO:2, which when excised from the pre-miRNA can be excised with residues 51 to 72 of SEQ ID NO:2 when the pre-miRNA is in a stem-loop or hairpin conformation. Thus, the term miR-122 includes these sequences as well as variants, modifications, and derivatives thereof.

As used herein, the term "mature miRNA" refers to the miRNA molecule or molecules that is/are excised from a pre-miRNA molecule, e.g., a pre-miRNA hairpin or stem-loop structure. Since pre-miRNA molecules can be in hairpin or stem-loop conformation, two miRNA molecules originating from opposite ends of the pre-miRNA molecules and optionally located on opposite strands in a hairpin or stem-loop structure can be excised from the pre-miRNA. The term "mature miRNA" includes miRNA molecules comprising one or both molecules excised from the pre-miRNA molecule. Thus, the terms "mature miR-105" and "mature form of miR-105" refer to the miRNA molecule or molecules excised from the pre-miR-105 molecule. Likewise, the terms "mature miR-122," and "mature form of miR-122" refer to the miRNA molecule or molecules excised from the pre-miR-122 molecule. The terms "mature miR-105" and "mature form of miR-105" can refer to a miR-105 comprising residues 13 to 35 of SEQ ID NO:1 and/or comprising residues 51 to 72 of SEQ ID NO:1. Optionally, the terms "mature miR-105" or "mature form of miR-105" refer to miR-105 comprising residues 13 to 35 of SEQ ID NO:1. Further, the terms "mature miR-122" and "mature form of miR-122" can refer to miR-122 comprising residues 15 to 36 of SEQ ID NO:2 and/or comprising residues 51 to 72 of SEQ ID NO:2. Optionally, the terms "mature miR-122" and "mature form of miR-122" refer to miR-122 comprising residues 15 to 36 of SEQ ID NO:2.

Described herein, inter alia, are markers for treatment of breast cancer. As described in more detail in the examples below, miR-105 induces the migratory potential of cancer cells as well as destroys the epithelial and endothelial barriers in the cancer niche by targeting the cellular tight junctions. In breast cancer patients, increased levels of miR-105 in the circulation can be detected at the pre-metastatic stage and predict the occurrence of metastasis. Anti-miR-105 treatment suppresses metastasis and abolishes the systemic effect of tumor-derived miR-105 on niche adaptation. Further, it is demonstrated herein that miR-122 is secreted by cancer cells and the prevalence of circulating miR-122 in breast cancer patients can be detected and used to predict breast cancer metastasis in early-stage patients or subjects. It is also demonstrated herein that miR-122 down-regulates glucose metabolic enzymes in niche cells leading to reduced glucose utilization. Specifically, cancer cell can suppress glucose uptake in fibroblasts and astrocytes in the metastatic niche by secretion of miR-122. This allows for cancer cells to have glucose more readily available to sustain their rapid proliferation when competing among other cell types in the niche. MiR-122 suppresses glucose uptake in vitro and in vivo through down-regulating the glycolytic enzyme pyruvate kinase, isoform M2 (PKM2). The in vivo data indicate that reduced glucose uptake can be detected in a distant organ at pre-metastatic stage, and miR-122 intervention can relieve this effect of cancer. Further, in vivo treatment with anti-miR-122 compound decreases the incidence of metastasis.

Thus, provided herein, inter alia, are detection methods that can be used for determining a level of mir-105, mir-122 and combinations thereof. One of skill will appreciate that each of the detection methods can be used alone or in combination. Thus, provided are methods of determining whether a subject has or is at risk for developing breast cancer including determining a level of miR-105 and/or a level of miR-122 or a combination thereof in the subject. A higher level of miR-105 or miR-122 as compared to a control indicates that the subject has or is at risk of developing breast cancer. Also provided are methods of determining a level of miR-105 and/or a level of miR-122 in a subject that has or is at risk for developing breast cancer. The method includes determining a level of miR-105 or a level of miR-122 in a biological sample from the subject. Optionally, the method further includes obtaining a biological sample from a subject. Optionally, levels of the mature form of miR-105, levels of pri-miR-105, levels of pre-miR-105, levels of the mature form of miR-122, levels of pri-miR-122, levels of pre-miR-122, or any combination thereof are determined. Optionally, the determining step comprises contacting the biological sample with one or more probes capable of binding to miR-105 or miR-122 and detecting binding of the one or more probes to the miR-105 or miR-122. Optionally, the probes are labeled probes. Optionally, the miR-105 comprises SEQ ID NO:1 or residues 13 to 35 of SEQ ID NO:1. Optionally, the miR-122 comprises SEQ ID NO:2 or residues 15 to 36 of SEQ ID NO:2.

Also provided are methods of determining progression of breast cancer in a subject. The method includes determining a first level of miR-105 and/or a first level of miR-122 in a first biological sample from the subject at a first time point, determining a second level of miR-105 and/or second level of miR-122 in a second biological sample from the subject at a second time point, and comparing the first level of miR-105 to the second level of miR-105 and/or comparing the first level of miR-122 to a second level of mi-122, thereby determining progression of breast cancer in said subject. Optionally, the first biological sample is a first blood-derived biological sample and the second biological sample is a second blood-derived biological sample. Optionally, the determining step comprises contacting the biological sample with one or more probes capable of binding to miR-105 or miR-122 and detecting binding of the one or more probes to the miR-105 or miR-122. Optionally, the probes are labeled probes. Optionally, the miR-105 comprises SEQ ID NO:1 or residues 13 to 35 of SEQ ID NO:1. Optionally, the miR-122 comprises SEQ ID NO:2 or residues 15 to 36 of SEQ ID NO:2.

Provided are methods of increasing vascular permeability in a subject. The method includes administering to the subject an effective amount of miR-105 to increase vascular permeability in the subject, (e.g., relative to the absence of miR-105). Optionally, the method includes selecting a subject in need of increased vascular permeability. For example, the subject can be a subject with cancer.

Also provided are methods of reducing glucose uptake in a cell. The method includes contacting the cell with an effective amount of miR-122 to reduce glucose uptake in the cell. In embodiments, the cell forms part of an organism or subject, such as a human subject. Also provided herein is a method of reducing glucose uptake is a subject. The method includes administering to the subject an effective around of miR-122 to reduce glucose uptake in the subject. Reducing glucose uptake in a subject includes a reduction or decrease in the uptake of glucose by the cells of a subject. Optionally, the methods include selecting a subject or cell in need of reduced glucose uptake.

Optionally, the provided methods further include selecting a subject that has or is at risk for developing breast cancer. Subjects with breast cancer includes subject with one or more signs or symptoms of breast cancer. Signs and symptoms of breast cancer include lumps found in breast tissue, lumps found in the lymph nodes, thickening of breast tissue, one breast becoming larger or lower, a nipple changing position or shape or becoming inverted, breast skin puckering or dimpling, a rash on or around a nipple, discharge from one or both nipples, constant pain in part of the breast or armpit, and swelling beneath the armpit or around the collarbone.

In general, breast cancers can be divided into at least four types based on gene expression, cellular morphology, and response to treatment. Breast cancers can first be divided into two broad groups, estrogen-receptor (ER)-positive and ER-negative. These two groups can further be subdivided into additional distinct biologically and clinically significant subgroups. ER-positive tumors express estrogen-receptor, ER-responsive genes, and other proteins of luminal epithelial cells. Thus, ER-positive tumors are referred to as luminal tumors, which can further be classified into luminal A and luminal B tumors, depending on the characteristic gene expression patterns. ER-negative tumors can be further classified into at least two groups, HER-2 positive or HER-2 enriched, and basal-like tumors. HER-2 positive tumors express high levels of genes located in the HER2 amplicon on chromosome 17 at location 17q21, including HER-2. Basal-like tumors express genes characteristic of basal cells. Basal-like tumors lack expression or express lower levels of ER, ER-responsive genes, and other genes characteristic of luminal epithelial cells. Thus, optionally, the breast cancer is ER-positive breast cancer or ER-negative breast cancer. Optionally, the breast cancer is luminal breast cancer, HER-2 positive breast cancer or basal-like breast cancer. Optionally, the breast cancer is luminal A- or luminal B-type breast cancer.

Optionally, the breast cancer is metastatic breast cancer. Common sites of metastatic breast cancer include bone, liver, lung and brain. As used herein, the term metastatic refers to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if breast cancer metastasizes to the lung, the secondary tumor at the site of the lung consists of abnormal breast cells and not abnormal lung cells. The secondary tumor in the lung is referred to a metastatic breast cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic breast cancer refers to a disease in a subject with or with a history of a primary breast tumor and with one or more secondary tumors at a second location or multiple locations, e.g., in the lung.

The step of determining the levels of miR-105 and/or miR-122 includes detecting miR-105 and/or miR-122 in a biological sample. As used herein, biological samples include, but are not limited to, cells, tissues and bodily fluids. Bodily fluids that used to evaluate the presence or absence of the herein disclosed biomarkers include without limitation blood, urine, serum, tears, lymph, bile, cerebrospinal fluid, interstitial fluid, aqueous or vitreous humor, colostrum, sputum, amniotic fluid, saliva, perspiration, transudate, exudate, and synovial fluid. By way of example, levels of biomarker are measured in the blood or biopsy before and/or after treatment in a subject. Biopsy refers to the removal of a sample of tissue for purposes of diagnosis. For example, a biopsy is from a cancer or tumor, including a sample of tissue from an abnormal area or an entire tumor. Optionally, the biological sample is a blood-derived biological sample.

miRNA can be separated from other RNA molecules in a biological sample using methods known to in the art. Optionally, miRNA are separated from other RNA molecules using chromatography. Optionally, gel chromatography can be performed using a polyacrylamide gel and tube electrophoresis.

Disclosed herein are biomarkers, e.g., miR-105 and miR-122, and methods for identifying and using the biomarkers. By biomarker is meant any assayable characteristics or compositions that are used to identify or monitor a condition (e.g., a tumor or other cancer, or lack thereof) or a therapy for said condition in a subject or sample. A biomarker is, for example, miR-105 and/or miR-122 whose presence, absence, or relative amount is used to identify a condition or status of a condition in a subject or sample. Biomarkers identified herein are measured to determine levels, expression, activity, or to detect variants.

As discussed above, miR-105 and miR-122 are miRNA molecules. Methods for detecting and determining levels of miRNA molecules including miR-105 and miR-122 are known. Methods for detecting and identifying nucleic acids and proteins and interactions between such molecules involve conventional molecular biology, microbiology, and recombinant DNA techniques within the skill of the art. Such techniques are explained fully in the literature (see, e.g., Sambrook, Fritsch & Maniatis, Molecular Cloning: A Laboratory Manual, Second Edition 1989, Cold Spring Harbor Laboratory Press, Cold Spring Harbor, N.Y.; Animal Cell Culture, R. I. Freshney, ed., 1986). Optionally, the level of SEQ ID NO:1, the level of SEQ ID NO:2, the level of the mature form of miR-105 (residues 13-35 of SEQ ID NO:1), the level of the mature form of miR-122 (residues 15-36 of SEQ ID NO:2), or a combination thereof is determined.

Methods for detecting RNA are largely cumulative with the nucleic acid detection assays and include, for example, Northern blots, RT-PCR, arrays including microarrays and sequencing including high-throughput sequencing methods. In some embodiments, a reverse transcriptase reaction is carried out and the targeted sequence is then amplified using standard PCR. Quantitative PCR (qPCR) or real time PCR (RT-PCR) is useful for determining relative expression levels, when compared to a control. Quantitative PCR techniques and platforms are known in the art, and commercially available (see, e.g., the qPCR Symposium website, available at qpersymposium.com). Nucleic acid arrays are also useful for detecting nucleic acid expression. Customizable arrays are available from, e.g., Affymatrix.

Optionally, methods for detecting RNA include sequencing methods. RNA sequencing are known and can be performed with a variety of platforms including, but not limited to, platforms provided by Illumina, Inc., (La Jolla, Calif.) or Life Technologies (Carlsbad, Calif.). See, e.g., Wang, et al., Nat Rev Genet. 10(1):57-63 (2009); and Martin, Nat Rev Genet. 12(10):671-82 (2011). Optionally, methods for detecting RNA including miRNA include microarray methods, which are known and can be performed with a variety of platforms including, but not limited to, platforms provided by Ambion, Inc., (Austin, Tex.) and Life Technologies (Carlsbad, Calif.).

Optionally, the miRNA molecules, e.g., miR-105 and miR-122, are detecting using one or more probes, which can be referred to herein as miRNA probes. Thus, optionally, the provided methods include contacting a sample, e.g., a biological sample, with one or more probes capable of binding to miR-105 or miR-122. Optionally, the probes are labeled. The miRNA probes can be made of DNA, though in some embodiments, they may be RNA, nucleotide analogs, peptide nucleic acids (PNAs), or any combination of DNA, RNA, nucleotide analogs, and PNAs. The provided probes can be complementary to one or more nucleic acid residues of miR-105 or miR-122. Thus, the provided probes can bind miR-105, wherein the miR-105 comprises SEQ ID NO:1, residues 13 to 35 of SEQ ID NO:1, or a fragment, variant, modification, or derivative thereof. Optionally, the provided probes bind miR-122, wherein the miR-122 comprises SEQ ID NO:2, residues 15 to 36 of SEQ ID NO:2, or a fragment, variant, modification or derivative thereof. By way of example, the probes can be of 10, 11, 12, 13, 14, 15, 16, 17, 18, 19, 20, 21, 22, 23, 24, or 25 residues in length. Optionally, the probes are 25, 30, 35, 40, 45, 50, 55, 60, 65, 70, 75, 80, 85, or any length between 25-85 inclusive, residues in length. The provided probes can be complementary to at least 10 nucleic acid residues of miR-105 or miR-122. Thus, the provided probes are or are at least complementary to 10, 11, 12, 13, 14, 15, 16, 17, 18, 19, 20, 21, 22, 23, 24, 25, 30, 35, 40, 45, 50, 55, 60, 65, 70, 75, 80, or 85 nucleic acid residues of the miRNA. Optionally, the nucleic acid residues of the miRNA, e.g., miR-105 and miR-122, to which the probes bind are continugous. Optionally, the provided probes are fully complementary to the sequences of miR-105 or miR-122. Thus, the provided probes can be the same as or nearly the same as the miRNA gene and complementary to the processed miRNA, i.e., mature form, or its precursors, e.g., the pri- or pre-form. As discussed above, it is contemplated that miRNA probes may be almost fully complementary (1, 2, 3, 4, 5, 6, 7, 8, 9, 10 base-pair mismatches or fewer) or fully complementary to any miRNA sequence or set of sequences that is targeted. Optionally, the probe is a probe that binds miR-105 and the probe comprises residues 51-72 of SEQ ID NO:1. Optionally, the probe is a probe that binds miR-122 and the probe comprises residues 51-72 of SEQ ID NO:2.

Provided herein is an in vitro complex comprising a nucleic acid probe hybridized to a nucleic acid, wherein said nucleic acid is a miR-105 or miR-122 sequence extracted from a subject that has or is at risk for developing breast cancer or is an amplification product of a miR-105 or miR-122 sequence extracted from a subject that has or is at risk for developing breast cancer. The probe can be labeled. As discussed above, the probe can be complementary to at least 10 nucleic acid residues of miR-105 or miR-122. Optionally, the probe is fully complementary. Optionally, the nucleic acid residues of miR-105 or miR-122 to which the probe is hybridized are continugous. Optionally, the miR-105 sequence comprises the pri-, pre-, and/or mature forms of miR-105. Optionally, the miR-105 sequence comprises SEQ ID NO:1 or residues 13-35 of SEQ ID NO:1. Optionally, the miR-122 sequence comprises the pri-, pre-, and/or mature forms of miR-122. Optionally, the miR-122 sequence comprises SEQ ID NO:2 or residues 15-36 of SEQ ID NO:2. As noted above, the probes can be 10, 11, 12, 13, 14, 15, 16, 17, 18, 19, 20, 21, 22, 23, 24, or 25, residues in length. Optionally, the probe is 25, 30, 35, 40, 45, 50, 55, 60, 65, 70, 75, 80, or 85 residues in length. Optionally, the probe is a probe that binds miR-105 and the probe comprises residues 51-72 of SEQ ID NO:1. Optionally, the probe is a probe that binds miR-122 and the probe comprises residues 51-72 of SEQ ID NO:2.

In addition to miR-105 and miR-122, additional biomarkers of breast cancer can be assayed. Thus, in the provided methods, the expression or activity of at least one additional breast cancer marker can be determined and compared to a standard control for the breast cancer marker. Other biomarkers of breast cancer, include, but are not limited to, BRCA1, BRCA2, p53, PTEN, STK11, CHEK2, ATM, BRIP1, and PALB2. Thus, the provided methods optionally include the step of determining the level or activity of one or more of BRCA1, BRCA2, p53, PTEN, STK11, CHEK2, ATM, BRIP1, and PALB2.

The disclosed methods involve comparing the levels or activity of a biomarker, e.g., miR-105 and/or miR-122, from a test sample to a control sample. A control sample or value refers to a sample that serves as a reference, usually a known reference, for comparison to a test sample. For example, a test sample can be taken from a patient suspected of having breast cancer and compared to samples from a known breast cancer subject or a known normal (non-disease) subject. A control can also represent an average value gathered from a population of similar individuals, e.g., breast cancer patients or healthy individuals with a similar medical background, same age, weight, etc. A control value can also be obtained from the same individual, e.g., from an earlier-obtained sample, prior to disease, or prior to treatment. One of skill will recognize that controls can be designed for assessment of any number of parameters. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

The terms comparing, correlating and associated, in reference to determination of a breast cancer risk factor, refers to comparing the presence or amount of the risk factor (e.g., dysregulation of miR-105 and/or miR-122) in an individual to its presence or amount in persons known to suffer from, or known to be at risk of breast cancer, or in persons known to be free of breast cancer, and assigning an increased or decreased probability of having/developing breast cancer to an individual based on the assay result(s).

Optionally, the methods of determining whether a subject has or is at risk for developing breast cancer further include administering to the subject an effective amount of a composition comprising an inhibitor of miR-105 or miR-122 or a combination thereof. Optionally, the inhibitor is selected from the group consisting of a peptide, small molecule, nucleic acid and an antibody. Optionally, the inhibitor is an inhibitory nucleic acid such as, for example, an miRNA or siRNA. Optionally, the methods of determining whether a subject has or is at risk for developing breast cancer includes administering to the subject an effective amount of a further therapeutic agent. Therapeutic agents, include, for example, a chemotherapeutic agent, a HER2 antibody. Optionally, the therapeutic agent is selected from the group consisting of cyclophosphamide, doxorubicin, docetaxel, methotrexate, 5-fluorouracil, trastuzumab, tamoxifen, and an aromatase inhibitor.

Thus, provided are methods of treating breast cancer in a subject in need thereof comprising administering to the subject an effective amount of an inhibitor of miR-105 or an inhibitor of miR-122. Optionally, the inhibitor of miR-105 or the inhibitor of miR-122 forms part of a pharmaceutical composition that further comprises a pharmaceutically acceptable excipient.

Provided herein are inhibitors of miR-105 or miR-122 that can be used in the provided compositions and methods. As used herein, an inhibitor refers to an agent or compound that inhibits miR-105 or miR-122 directly or indirectly. For example, an inhibitor of miR-105 can inhibit the expression or activity of miR-105. Similarly, an inhibitor of miR-105 can inhibit the expression or activity of miR-122 Inhibitors of miR-105 or miR-122 include, but are not limited to of a peptide, small molecule, nucleic acid and an antibody. Such inhibitors can be made using the nucleic acid sequences of miR-105 and miR-122. Nucleic acid sequences of miR-105 can be found, for example, at GenBank Accession Nos. AF480503, and AF480547 and UGUGCAUCGUGGU-CAAAUGCUCAGACUCCUGUGGUGGCUGCUCAUG-CACCACGGAUGUUUGAGCAUGUGCUACGGUGU-CUA (SEQ ID NO:1) and functional fragments thereof. Nucleic acid sequences of miR-122 can be found, for example, at GenBank Accession No. NR_029667.1 and CCUUAGCAGAGCUGUGGAGUGUGACAAUGGU-GUUUGUGUCUAAACUAUCAAACGCCAUUAUCA-CACUAAAUAGCUACUGCUAGGC (SEQ ID NO:2) and functional fragments thereof.

Inhibitors of miR-105 or miR-122 include inhibitory peptides or polypeptides. As used herein, the term peptide, polypeptide, protein or peptide portion is used broadly herein to mean two or more amino acids linked by a peptide bond. Protein, peptide and polypeptide are also used herein interchangeably to refer to amino acid sequences. The term fragment is used herein to refer to a portion of a full-length polypeptide or protein. It should be recognized that the term polypeptide is not used herein to suggest a particular size or number of amino acids comprising the molecule and that a peptide of the invention can contain up to several amino acid residues or more.

Optionally, the inhibitor of miR-105 or miR-122 is a functional nucleic acids. Such functional nucleic acids include, but are not limited to, antisense molecules and ribozymes. Thus, for example, an antisense oligonucleotide could be used to reduce or eliminate miR-105 or miR-122. Functional nucleic acids are generally designed using algorithms and a conventional nucleic acid synthesizer. As discussed in more detail below, such nucleic acids can, optionally, comprise one or more chemical modifications to improve in vitro and in vivo stability or delivery.

Functional nucleic acids are nucleic acid molecules that have a specific function, such as binding a target molecule or catalyzing a specific reaction. Functional nucleic acid molecules can interact with any macromolecule, such as DNA, RNA, polypeptides, or carbohydrate chains. Thus, functional nucleic acids can interact with the miR-105 or miR-122 directly. Optionally, the inhibitor is an indirect inhibitor that interacts with the targets of miR-105 or miR-122 to inhibit the activity of miR-105 or miR-122 or reduce or eliminate the presence of miR-105 or miR-122. Often functional nucleic acids are designed to interact with other nucleic acids based on sequence homology between the target molecule and the functional nucleic acid molecule.

Antisense molecules or antisense oligonucleotides (ASOs) are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. See for example, Vermeulen et al., RNA 13: 723-730 (2007) and in WO2007/095387 and WO 2008/036825; Yue, et al., Curr. Genomics, 10(7):478-92 (2009) and Lennox Gene Ther. 18(12):1111-20 (2011), which are incorporated by reference herein in their entireties.

Thus, antisense molecules that inhibit miR-105 or miR-122 can be designed and made using standard nucleic acid synthesis techniques or obtained from a commercial entity, e.g., Regulus Therapeutics (San Diego, Calif.). Optionally, the antisense molecule is single-stranded and comprises RNA and/or DNA. Optionally, the backbone of the molecule is modified by various chemical modifications to improve the in vitro and in vivo stability and to improve the in vivo delivery of antisense molecules. Modifications of antisense molecules include, but are not limited to, 2'-O-methyl modifications, 2'-O-methyl modified ribose sugars with terminal phosphorothioates and a cholesterol group at the 3' end, 2'-O-methoxyethyl (2'-MOE) modifications, 2'-fluoro modifications, and 2',4' methylene modifications (referred to as "locked nucleic acids" or LNAs). Thus, inhibitory nucleic acids include, for example, modified oligonucleotides (2'-O-methylated or 2'-O-methoxyethyl), locked nucleic acids (LNA; see, e.g, Valóczi et al., Nucleic Acids Res. 32(22): e175 (2004)), morpholino oligonucleotides (see, e.g, Kloosterman et al., PLoS Biol 5(8):e203 (2007)), peptide nucleic acids (PNAs), PNA-peptide conjugates, and LNA/2'-O-methylated oligonucleotide mixmers (see, e.g., Fabiani and Gait, RNA 14:336-46 (2008)). Optionally, the antisense molecule is an antagomir. Antagomirs are oligonucleotides comprising 2'-O-methyl modified ribose sugars with terminal phosphorothioates and a cholesterol group at the 3' end. An exemplary antagomir of miR-105 includes ACCACAGGAGTCTGAGCATTTGA (SEQ ID NO:3). An exemplary antisense oligonucleotide of miR-122 includes CCATTGTCACACTCC (SEQ ID NO:4), which is optionally 2'-deoxy-2'-fluoro-modified on the residues in capital letters. Other miR-122 inhibitors include 5'-CcAttGTcaCaCtCC-3' (SEQ ID NO:4), with LNA in capitals, DNA in lower case, complete phosphorothioate backbone, and capital C denotes LNA methylcytosine, as described in Lanford et al., Science 327(5962):198-201 (2010), which is incorporated by reference herein in its entirety. See also Elmen et al., Nature 452:896-9 (2008); and Elmen et al., Nucleic Acids Res. 36:1153-1162 (2008), which are incorporated by reference herein in their entireties. MiR-122 inhibitors also include A*C*AAACACCAUUGUCACAC*U*C*C*A (SEQ ID NO:44) being fully 2'-O-Me RNA and * indicates phosphorothioate linkage, as well as CaAaCaCcAttGTcA (SEQ ID NO:45) and TTaGaGtgATaaTgG (SEQ ID NO:46) with LNA in capitals and DNA in lower case, as described in Gebert et al., Nucleic Acids Res. 42(1):609-21 (2013), which is incorporated herein by reference in its entirety.

Optionally, the nucleic acid comprises a targeting sequence of miR-105 or miR-122. Such miRNA-binding nucleic acids are referred to as miRNA decoys or miRNA sponges. For example, mRNAs with multiple copies of the miRNA target can be engineered into the 3' UTR of the mRNA creating an miRNA "sponge." The miRNA inhibitors function by sequestering the cellular miRNAs away from the mRNAs that normally would be targeted by them. Such nucleic acid decoys can be delivered, e.g., by viral vectors, and expressed to inhibit the activity of miR-105 or miR-122.

Ribozymes are nucleic acid molecules that are capable of catalyzing a chemical reaction, either intramolecularly or intermolecularly. Typically, ribozymes cleave RNA or DNA substrates. There are a number of different types of ribozymes that catalyze chemical reactions which are based on ribozymes found in natural systems, such as hammerhead ribozymes, and hairpin ribozymes. There are also a number of ribozymes that are not found in natural systems, but which have been engineered to catalyze specific reactions. See, for example, U.S. Pat. Nos. 5,807,718, and 5,910,408. Representative examples of how to make and use ribozymes to catalyze a variety of different reactions can be found in, for example, U.S. Pat. Nos. 5,837,855, 5,877,022, 5,972, 704, 5,989,906, and 6,017,756. Exemplary ribozymes of miR-122 are described in, for example, Lee et al., Nucleic Acid Ther. 22(1):17-29 (2012).

Thus, based on the sequences of miR-105 and miR-122, inhibitory nucleic acids can be designed to bind to any form of the miRNA, e.g., the pri-, pre- or mature form Inhibitory nucleic acids typically bind to at least a portion of the targeted sequence, in this case miR-105 or miR-122. The inhibitory nucleic acids are at least partially complementary to the pri-, pre-, or mature sequence of miR-105 or miR-122. A percent complementarity indicates the percentage of residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). 100% complementary means that all the residues of a nucleic acid sequence will hydrogen bond with the same number of residues in a second nucleic acid sequence. Thus, the microRNA inhibitor sequence has 100%, 95%, 90%, 85%, 80%, 75%, 70% complementarity, or any percent complementarity between 100% and 70%, to the pri-, pre-, or mature sequence of miR-105 or miR-122. Optionally, a first portion of the microRNA inhibitor sequence is identical (i.e., has 100% complementarity) to the pri-, pre-, or mature sequence of miR-105 or miR-122, while a second portion of the microRNA inhibitor sequence has less than 100% complementarity, e.g. 50%, to the pri-, pre-, or mature sequence of miR-105 or miR-122.

Optionally, the inhibitory nucleic acids specifically hybridizes to one or more of the pre-, pri- or mature forms of miR-105 or miR-122. The phrase selectively (or specifically) hybridizes to refers to the binding, duplexing, or hybridizing of a molecule only to a particular nucleotide sequence with a higher affinity, e.g., under more stringent conditions, than to other nucleotide sequences (e.g., total cellular or library DNA or RNA). One of skill in the art will appreciate that specific hybridization between nucleotides usually relies on Watson-Crick pair bonding between complementary nucleotide sequences, which is discussed in more detail above. Optionally, the inhibitory nucleic acids bind to the pri-, pre-, or mature forms of miR-105 or miR-122 under stringent or highly stringent conditions. The degree of stringency can be controlled by temperature, ionic strength, pH and/or the presence of a partially denaturing solvent such as formamide. For example, the stringency of hybridization is conveniently varied by changing the concentration of formamide within the range up to and about 50%. The degree of complementarity (sequence identity)

required for detectable binding will vary in accordance with the stringency of the hybridization medium and/or wash medium.

High stringency conditions for nucleic acid hybridization are well known in the art. For example, conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleotide content of the target sequence(s), the charge composition of the nucleic acid(s), and by the presence or concentration of formamide, tetramethylammonium chloride or other solvent(s) in a hybridization mixture. As discussed above, nucleic acids can be completely complementary to a target sequence or exhibit one or more mismatches.

Methods of screening for agents that inhibit the expression or activity of miR-105 or miR-122 directly or indirectly are provided. Such a screening method includes the steps of providing a cell or sample that expresses miR-105 or miR-122, contacting the cell with a candidate agent to be tested and determining whether the candidate agent reduces the level of miR-105 or miR-122 in the cell or sample. The cell can also be a prokaryotic or an eukaryotic cell that has, optionally, been transfected with a nucleotide sequence encoding a miR-105 or miR-122, operably linked to a promoter. Such agents may be useful as active ingredients included in pharmaceutical compositions for treating patients suffering from breast cancer. Methods for determining whether the candidate agent inhibits expression or activity of an miRNA molecule are well known to those of skill in the art. The assay can be, for example, a RT-PCR assay, sequencing, or one of the provided methods described in the examples below.

Optionally, the provided methods include administering a further therapeutic agent to the subject. Therapeutic agents, include, for example, a chemotherapeutic agent, .a HER2 antibody. Optionally, the therapeutic agent is selected from the group consisting of cyclophosphamide, doxorubicin, docetaxel, methotrexate, 5-fluorouracil, trastuzumab, tamoxifen, and an aromatase inhibitor. Optionally, the methods treatment further include determining a level of miR-105 or a level miR-122 in a biological sample from the subject as described herein.

Combinations of agents, e.g., an miR-105 inhibitor and a miR-122 inhibitor, may be administered either concomitantly (e.g., as an admixture), separately but simultaneously (e.g., via separate intravenous lines into the same subject), or sequentially (e.g., one of the compounds or agents is given first followed by the second). Thus, the term combination is used to refer to either concomitant, simultaneous, or sequential administration of two or more agents. The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

According to the methods provided herein, the subject is administered an effective amount of the agent. The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

Therapeutically effective amount, as used herein, refers to that amount of a therapeutic agent sufficient to reduce or ameliorate one or more symptoms of a disease or disorder. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

The terms higher, increases, elevates, or elevation refer to increases above a control. The terms low, lower, reduces, or reduction refer to any decrease below control levels. For example, control levels are in vivo levels prior to, or in the absence of, addition of an agent. The reduction includes a complete elimination of the invasiveness. Inhibit, inhibiting, and inhibition mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

As described herein, a control or standard control refers to a sample, measurement, or value that serves as a reference, usually a known reference, for comparison to a test sample, measurement, or value. For example, a test sample can be taken from a patient suspected of having a given disease (e.g. an autoimmune disease, inflammatory autoimmune disease, cancer, infectious disease, immune disease, or other disease) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. One of skill will recognize that standard controls can be designed for assessment of any number of parameters (e.g. RNA levels, protein levels, specific cell types, specific bodily fluids, specific tissues, and the like).

Provided are compositions comprises a single agent or more than one agent. Thus, provided are compositions comprising miR-122 or miR-105 or a combination thereof and, optionally, one or more further therapeutic agents. Optionally, the provided compositions comprise an inhibitor of miR-122 or miR-105 or a combination thereof and, optionally, one or more further therapeutic agents. The provided compositions are, optionally, suitable for formulation and administration in vitro or in vivo. Suitable carriers and excipients and their formulations are described in Remington: The Science and Practice of Pharmacy, 21st Edition, David B. Troy, ed., Lippicott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

The compositions disclosed herein can be administered by any means known in the art. For example, compositions may include administration to a subject intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intrathecally, subcutaneously, subconjunctival, intravesicularlly, mucosally, intrapericardially, intraumbilically, intraocularly, orally, locally, by inhalation, by injection, by infusion, by continuous infusion, by localized perfusion, via a catheter, via a lavage, in a creme, or in a lipid composition. Administration can be local, e.g., at or near the site of a tumor, or systemic.

The compositions for administration will commonly comprise an agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion Sterile injectable solutions can be prepared by incorporating the active compounds or constructs in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

Compositions can be formulated to provide quick, sustained or delayed release after administration by employing procedures known in the art. Certain carriers may be more preferable depending upon, for instance, the route of administration and concentration of composition being administered. Suitable formulations for use in the provided compositions can be found in Remington: The Science and Practice of Pharmacy, 21st Edition, David B. Troy, ed., Lippicott Williams & Wilkins (2005).

Provided herein are kits for treating breast cancer in a subject and for determining whether a subject has or is at risk for developing breast cancer. Optionally, the kit for treating breast cancer in a subject comprises one or more doses of an effective amount of a composition comprising an inhibitor of miR-105 and/or miR-122. Optionally, the composition is present in a container such as a vial or packet. Optionally, the kit comprises one or more additional agents for treating or preventing one or more symptom of breast cancer. Thus, for example, the kit further includes an additional or second therapeutic agent, e.g., a chemotherapeutic agent. The additional or second therapeutic agent may be included in the composition or formulated as a second composition. Optionally, the kit comprises a means of administering the compositions, such as, for example, a syringe, needle, tubing, catheter, patch, and the like. The kit may also comprise formulations and/or materials requiring sterilization and/or dilution prior to use.

Provided are kits for determining a level of miR-105 or miR-122 or a combination thereof. The provided kits include components for assessing miR-105 and/or miR-122 expression comprising, e.g., a nucleic acid capable of detecting miR-105 and/or miR-122, optionally labeled. Thus, the provided kits may include a binding agent capable of binding to a substance within a biological sample from a subject that has or is at risk for developing breast cancer, wherein said substance is (i) a nucleic acid sequence comprising a miR-105 or miR-122 sequence, or (ii) a nucleic acid amplification product of miR-105 or miR-122. Optionally, the binding kits further include a detecting reagent or a detecting apparatus capable of detecting binding of said binding agent to said substance. Optionally, the detecting reagent is a label on the probe. Optionally, the detecting apparatus is an apparatus for performing Northern blot analysis, RT-PCR, microarray analysis or sequencing analysis. The binding agent can be a probe capable of binding the nucleic acid sequence comprising miR-105 or miR-122 or the nucleic acid amplification product of miR-105 or miR-122. Optionally, the kit includes one or more probes capable of binding miR-105 and one or more probes capable of binding miR-122. Optionally, the probes are labeled probes.

The probes can be complementary to at least 10 nucleic acid residues of miR-105 or miR-122. Optionally, the miR-105 comprises SEQ ID NO:1 or residues 13-35 of SEQ ID NO:1. Optionally, the miR-122 comprises SEQ ID NO:2 or residues 15-36 of SEQ ID NO:2. Optionally, the probes are fully complementary to miR-105 or miR-122. Optionally, the nucleic acid residues in miR-105 or miR-122 to which the probe binds are contiguous. As discussed herein, the probes can be 10, 11, 12, 13, 14, 15, 16, 17, 18, 19, 20, 21, 22, 23, 24, or 25, residues in length. Optionally, the probe is 25, 30, 35, 40, 45, 50, 55, 60, 65, 70, 75, 80, or 85 residues in length. As discussed above, the provided probes can be designed to bind to the pri-, pre-, or mature forms of miR-105 or miR-122. Optionally, the miR-105 comprises SEQ ID NO:1 or residues 13-35 of SEQ ID NO:1. Optionally, the miR-122 comprises SEQ ID NO:2 or residues 15-36 of SEQ ID NO:2. Optionally, the probe is a probe that binds miR-105 and the probe comprises residues 51-72 of SEQ ID NO:1. Optionally, the probe is a probe that binds miR-122 and the probe comprises residues 51-72 of SEQ ID NO:2. Thus, provided is a kit comprising a probe comprising residues 51-72 of SEQ ID NO:2 and/or a probe comprising residues 51-72 of SEQ ID NO:1. The kit can further include assay containers (tubes), buffers, or enzymes necessary for carrying out the detection assay.

In some embodiments, the kit includes components to examine more than one breast cancer marker. For example, the kit can include marker detection agents, such as marker specific primers or probes attached to an addressable array. Kits can also include components for comparing results such as a suitable control sample, for example a positive and/or negative control. The kit can also include a collection device for collecting and/or holding the sample from the subject. The collection device can include a sterile swab or needle (for collecting blood), and/or a sterile tube (e.g., for holding the swab or a bodily fluid sample). Optionally, the provided kits include instructions for use.

As used throughout, a subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient, individual and subject may be used interchangeably and these terms are not intended to be limiting. That is, an individual described as a patient does not necessarily have a given disease, but may be merely seeking medical advice. The terms patient or subject include human and veterinary subjects.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

A number of embodiments have been described. Nevertheless, it will be understood that various modifications may be made. Accordingly, other embodiments are within the scope of the claims below.

EXAMPLES

Example 1. Cancer-Derived miR-105 Promotes Tumor Invasion and Destroys the Natural Barriers Against Metastasis Metastasis is the leading cause of mortality in cancer patients. For breast cancer (BC), nearly 50% of patients treated with chemotherapeutic and/or hormonal agents develop distant metastatic disease (Nicolini et al., Biomed Pharmacother., 60:548-556 (2006); Rubens, Int. J. Clin. Pract. 55:676-9 (2001)); these patients face a median survival of 1-2 years and a 5-year survival rate of only ~20% (Yardley, Clin. Breast Cancer, 10:64-73 (2010)). Therefore, there is need to develop predictive or early diagnostic markers for metastasis and to elucidate the molecular mechanisms of metastasis that would allow development of efficient treatment options. In the "seed and soil" hypothesis for metastasis (Paget, Lancet, 133:571-3 (1989)), migratory tumor cells leave the primary tumor through intravasation, disseminate throughout the body via the circulation, and eventually engraft in a distant organ that provides an appropriate microenvironment. These consecutive steps require close interplay between cancer cells and their microenvironment. The intrinsic properties of cancer cells, e.g., their potential to migrate and traverse the epithelial and endothelial barriers in the primary niche, and, once disseminated, to invade, survive, and colonize the metastatic niche, are prerequisites for metastasis. Meanwhile, the adaptation of primary and secondary (metastatic) niches by cancer to facilitate cancer cell dissemination and distant engraftment also plays an important pro-metastatic role that is starting to be recognized (Chambers et al., Nat. Rev. Cancer, 2:563-572 (2002); Podsypanina et al., Science, 321:1841-4 (2008); Psaila and Lyden, Nat. Rev. Cancer, 9:285-293 (2009); Sethi and Kang, Nat. Rev. Cancer, 11:735-748 (2011)). The recent discovery of microRNAs (miRNAs) and their extracellular presence suggest a potential role of these regulatory molecules in defining the metastatic potential of cancer cells and mediating the cancer-host communication.

MiRNAs are small non-coding RNAs that base-pair with the 3' untranslated regions (UTRs) of protein-encoding mRNAs, resulting in mRNA destabilization and/or translational inhibition. The biogenesis of miRNAs is tightly controlled, and dysregulation of miRNAs is linked to cancer (Calin and Croce, Nat. Rev. Cancer, 6:857-866 (2006); Iorio et al., Cancer Res. 65:7065-7070 (2005)). It was recently discovered that miRNAs are also present extracellularly, either through binding to protein or lipid carriers (Arroyo et al., PNAS, 108:5003-8 (2011); Turchinovich et al., Nucleic Acids Res. 39:7223-7233 (2011); Vickers and Remaley, Curr. Opin. Lipidol. 23:91-7 (2012)) or as a major RNA component of exosomes (Redis et al., Pharmacol. Ther. 136:169-174 (2012); Valadi et al., Nat. Cell. Biol., 9:654-9 (2007)). Exosomes are small (30-100 nm) membrane-encapsulated vesicles that are released into the extracellular environment by many cell types, including cancer cells (Skog et al., Nat. Cell Biol. 10:1470-6 (2008); Valadi et al., Nat. Cell Biol. 9:654-9 (2007); Yuan et al., PLoS One 4:e4722 (2009)). Exosomal RNAs are heterogeneous in size but enriched in small RNAs, such as miRNAs. Cancer-secreted exosomes and miRNAs can be internalized by other cell types in the cancer niche (Hood et al., Cancer Res., 71:3792-3801 (2011); Peinado et al., Nat. Med., 18:883-891 (2012); Skog et al., Nat. Cell Biol., 10:1470-1476 (2008); Yuan et al., PLoS One, 4:e4722 (2009); Zhang et al., Mol. Cell, 39:133-144 (2010); Zhuang et al., EMBO J., 31:3513-3523 (2012)). MiRNAs loaded in these exosomes, which to a certain extent reflect the dysregulated miRNA profile in cancer cells, can thus be transferred to recipient niche cells to exert genome-wide regulation of gene expression. In addition, cancer-derived exosomal miRNAs may bind as ligands to Toll-like receptors in surrounding immune cells (Fabbri et al., PNAS, 109:E2110-6 (2012)). Therefore, cancer-secreted miRNAs may play a crucial role in regulating various cellular components of the tumor microenvironment in order to facilitate metastasis.

Cancer-derived circulating miRNAs carried by exosomes have been detected in the blood of cancer patients, and reflect the pathologic features of cancer (Mitchell et al., PNAS, 105:10513-10518 (2008); Taylor and Gercel-Taylor, Gynecol. Oncol., 110:13-21 (2008); Zhu et al., BMC Res. Notes, 2:89 (2009)). Previous studies from our and other groups have identified circulating miRNAs associated with the histopathological features of breast tumors and clinical outcomes in BC patients (Heneghan et al., Ann. Surg., 215:499-505 (2010); Jung et al., Cancer, 118:2603-2614 (2012); Roth et al., Breast Cancer Res., 12:R90 (2010); Wu et al., J. Transl. Med., 10:42 (2012)). Some of these miRNAs may play a role in cancer's preparation for metastasis. Herein miR-105, a miRNA uniquely expressed and secreted by metastatic breast cancer cells, is described and identified for its dual roles in promoting metastasis both inside and outside of cancer cells. The results indicate that miR-105 may serve as a predictive marker and therapeutic target for BC metastasis.

Results

MBC-Secreted Exosomal RNA Regulates Migration in Epithelial and Endothelial Niche Cells.

Figures 1A, 1B:
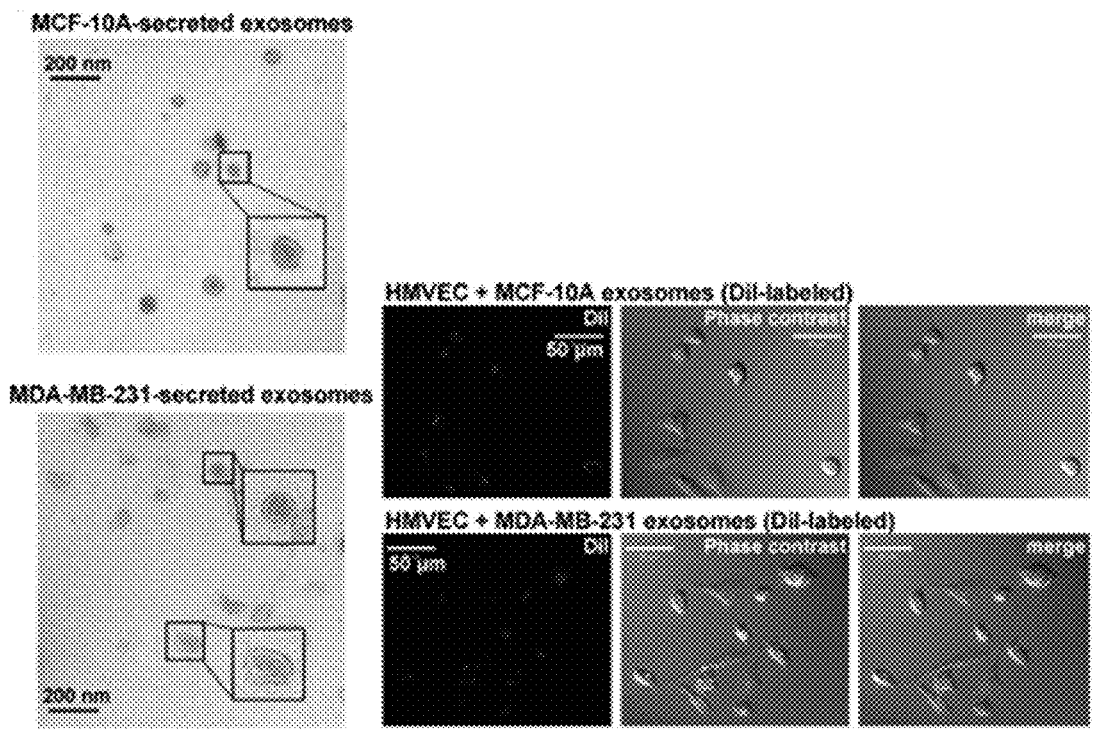
FIGS. 1A, 1B, 1C, 1D, and 1E show MDA-MB-231 metastatic breast cancer (MBC)-secreted exosomal RNA regulates migration in epithelial and endothelial cells.
Figure 1C:
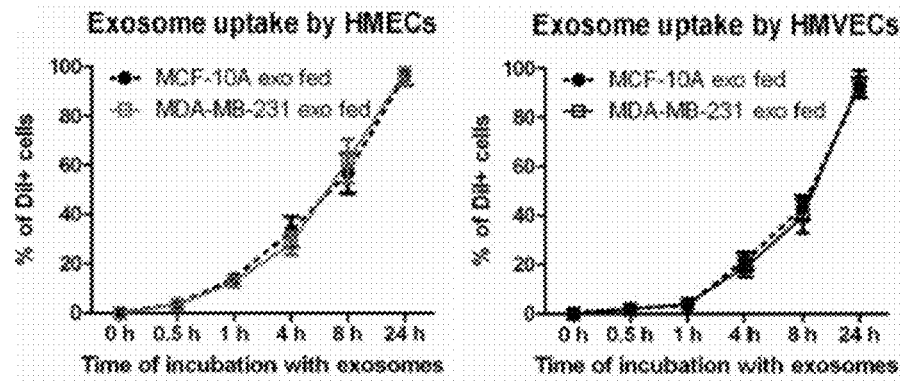
Figures 1D, 1E:
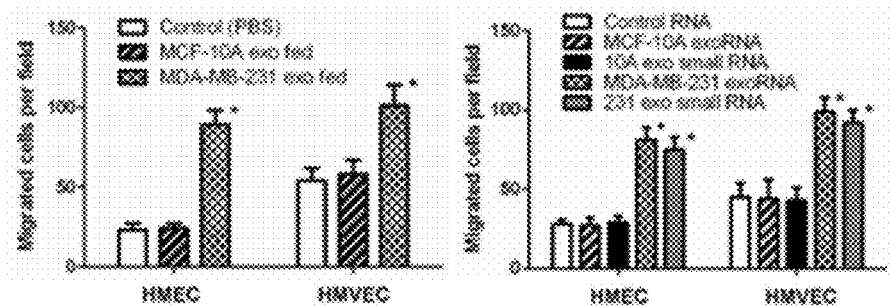

The MDA-MB-231 metastatic BC (MBC) line and the MCF-10A non-tumor mammary epithelial line were chosen as models for studying cancer-secreted exosomes and miRNAs. Exosomes purified from conditioned media (CM) by ultracentrifugation exhibited typical cup-shaped morphology by electron microscopy and a size range of 30-100 nm (FIGS. 1A and 9). When exosomes labeled with the fluorescent dye DiI were incubated with primary human mammary epithelial cells (HMECs) and human microvascular endothelial cells (HMVECs), both recipient cell types exhibited high uptake efficiency, as indicated by fluorescence microscopy (FIG. 1B) and flow cytometry (FIG. 1C), without a significant difference between MCF-10A- and MDA-MB-231-derived exosomes. After a 24 hour incubation with labeled exosomes, >90% of recipient cells were positive for DiI fluorescence (FIG. 1C). Among a series of cellular analyses in exosome-treated HMECs and HMVECs, it was found that the transwell migration of both cell types was significantly stimulated by MDA-MB-231-secreted, but not MCF-10A-secreted exosomes (FIG. 1D). Transfection of total or small RNA extracted from MDA-MB-231 exosomes, but not that from the MCF-10A exosomes, recapitulated the migration-inducing effect (FIG. 1E), thereby indicating that the unique small RNA content of MDA-MB-231 exosomes functions as a migratory regulator in recipient epithelial and endothelial cells.

MiR-105 is Specifically Expressed and Secreted by Metastatic Cancer Cells and can be Transferred to Niche Cells Via Exosome Secretion.

Figures 11C, 11D:
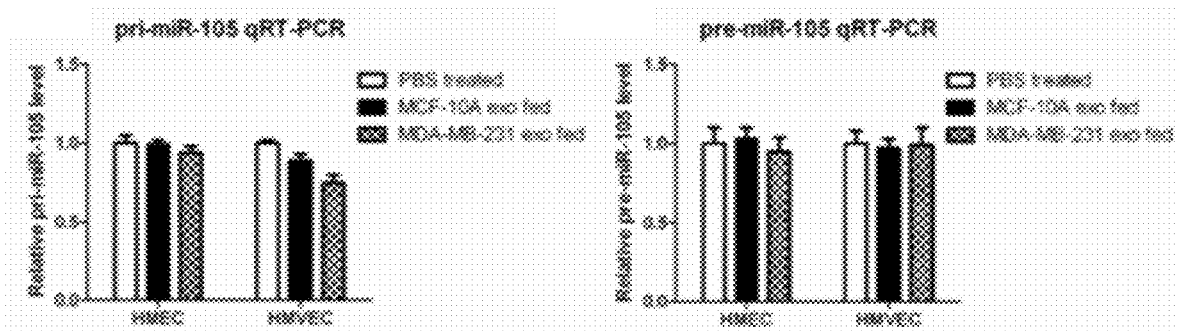

To identify the exosome-associated small RNA(s) that induce migration, all small RNAs in the exosomes were selected and profiled by Solexa deep sequencing. Exosomes from MDA-MB-231 and MCF-10A cells exhibited similar small RNA composition (FIG. 10). The focus was miRNAs that are known for their gene regulatory function, and a list of miRNAs differentially secreted between the two lines was identified. Among these, some showed the corresponding up- or down-regulation in the cells whereas others exhibited opposite changes between the exosomal and cellular compartments, which may suggest cell-type-specific mechanisms for highly selective enrichment or exclusion of the miRNA in exosome-mediated secretion. MiR-105 was a further focus that was predicted by multiple algorithms (TargetScan, miRDB, and PicTar) to target TJP1 (tight junction protein 1; also known as zonula occludens 1 or ZO-1), a migration-related gene. The secretion of mature miR-105 was highly specific to MDA-MB-231 and its expression was significantly higher in these cells compared to MCF-10A (FIGS. 2A and 2B). Although the primary (pri-) and precursor (pre-) miR-105 also exhibited higher intracellular levels in MDA-MB-231, these forms were not detectable in exosomes (FIGS. 11A and 11B). Among a panel of BC lines, the expression and secretion of miR-105 were specific to highly metastatic cells originally isolated from pleural effusion (indicating metastasis to lungs) (FIGS. 2A and 2B).

To confirm that MBC-secreted miR-105 can be transferred to recipient cells via exosomes, the miR-105 levels were measured in HMECs and HMVECs treated with exosomes derived from MCF-10A or MDA-MB-231 cells. An increase of the cellular level of mature miR-105, but not prior pre-miR-105, was observed in both recipient cell types following the treatment with MBC-originated exosomes with kinetics starting at 4 hours and peaking at 24 hours (FIGS. 2C, 2D, 2F, 11C, and 11D), similar to that observed for exosome uptake (FIG. 1C). The results indicate that this increase of miR-105 reflects the exosome-mediated miRNA transfer but not an induction of miR-105's endogenous expression in the recipient cells, as its level in exosome-treated cells was not significantly affected by an RNA polymerase II inhibitor (FIGS. 2E and 2G). When HMVECs were treated with PKH67-labeled exosomes secreted by MDA-MB-231 cells that were transfected with Cy3-labeled miR-105, the Cy3 fluorescence was observed in >90% of recipient cells where it largely colocalized with the PKH67 lipid dye that labeled the exosomal membranes. In contrast, no internalization of naked Cy3-labeled miR-105 was observed in HMVECs.

MiR-105 Regulates Migration Through Targeting the Tight Junction Protein ZO-1.

Figure 3A:
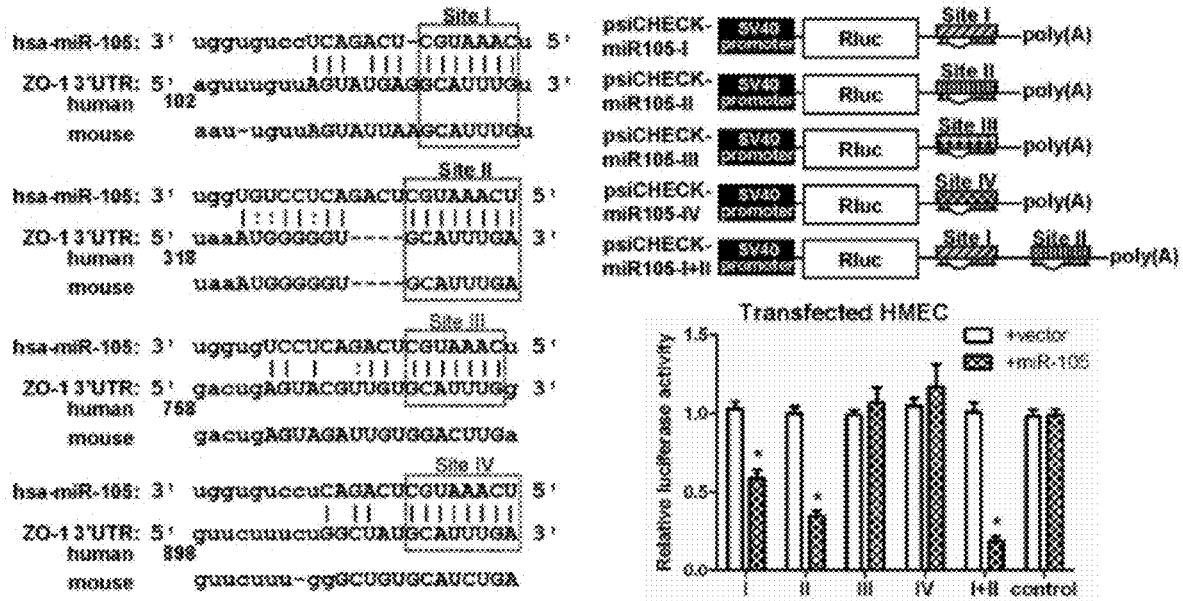
Figures 12A, 12B, 12C:
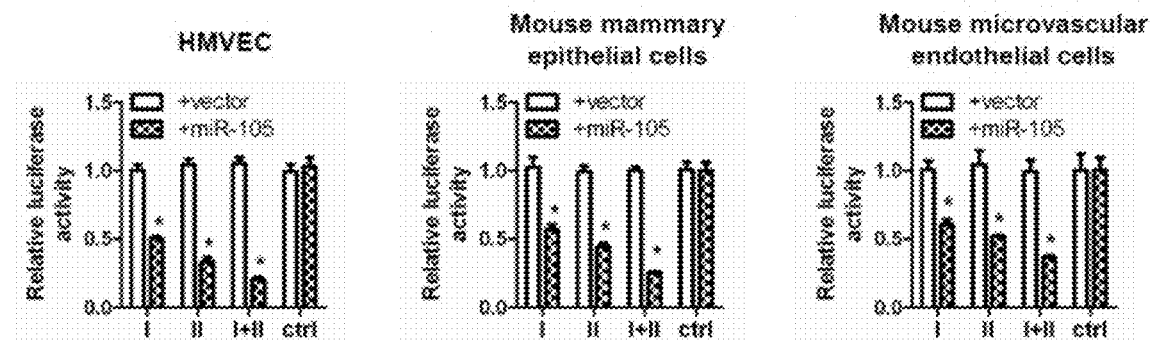
FIGS. 12A, 12B, and 12C are graphs showing ZO-1 3'UTR reporters respond to miR-105 in various cell types. The psiCHECK luciferase reporters indicated in FIG. 3A were used to transfect HMVECs (FIG. 12A), mouse mammary epithelial cells (FIG. 12B), or mouse microvascular endothelial cells (FIG. 12C) that were also infected with retrovirus expressing miR-105 or vector (as control). Luciferase activity was analyzed at 48 hours post transfection, and compared to the cells infected with the control virus. *p<0.005.

MiR-105 regulation of the putative target ZO-1 was then examined. ZO-1 is a central molecular component of tight junctions (TJs), which comprise a major group of cell-cell adjesion complexes in endothelial and epithelial cells. The four predicted miR-105 binding sites in the 3'UTR of human ZO-1 were cloned into a reporter plasmid and assessed for their responsiveness to miR-105 in HMECs. Site I and site II, which are conserved among most species, responded to retrovirus-expressed miR-105 by directing a 50-65% reduction in reporter gene expression, whereas the other two sites did not. When both sites I and II were present downstream of reporter gene, a greater reduction in gene expression was observed (FIG. 3A). Transfection into HMVECs as well as mouse primary epithelial and endothelial cells also showed similar results (FIGS. 12A, 12B and 12C).

Figure 3B:
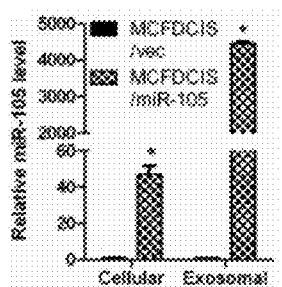
Figure 3C:
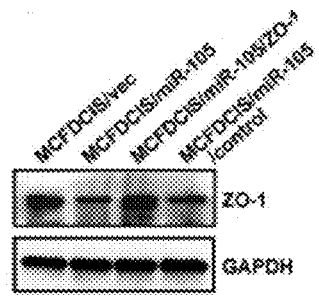
Figure 3D:
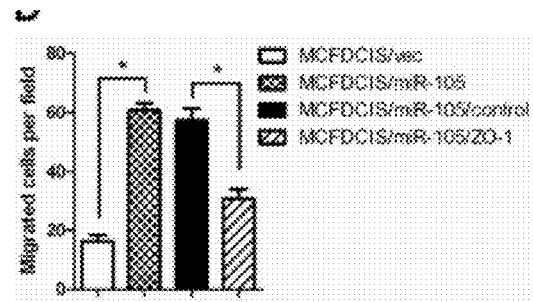
Figure 3E:
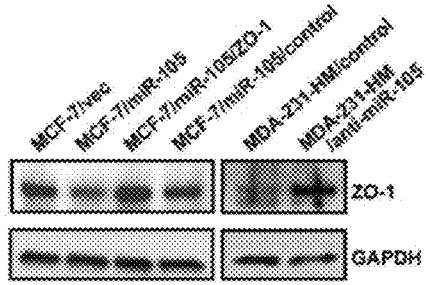
Figure 3C:
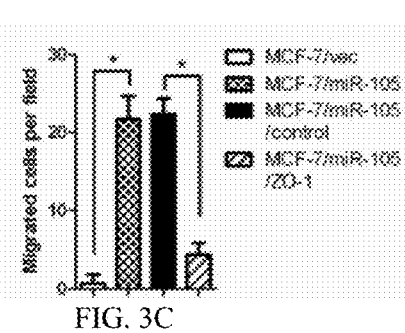
Figure 3D:
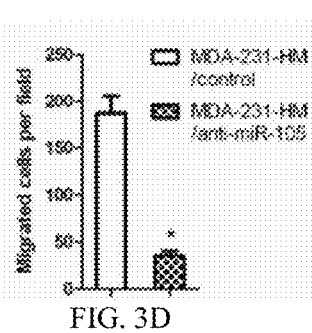

To further test the role of miR-105 and ZO-1, miR-105 was stably overexpressed in an MCF-10A-derived tumorigenic line MCFDCIS. Compared to vector-transduced control cells, the miR-105-overexpressing MCFDCIS cells also secreted a higher level of miR-105 (FIG. 3B), and showed reduced ZO-1 protein expression and significantly enhanced migration in transwell and wound closure assays (FIGS. 3C, 3D, and 13D). Restoration of ZO-1 using an overexpressing plasmid that lacks the 3'UTR abolished the pro-migratory effect of miR-105. Similar results of miR-105 overexpression were also observed in the poorly metastatic MCF-7 BC cell line (FIGS. 3E and 3F). In contrast, inhibition of endogenous miR-105 using an anti-miR-105 compound increased ZO-1 expression and suppressed migration in a highly metastatic MDA-MB-231 derivative line MDA-231-HM (FIG. 3G), which was generated through explant culture of a spontaneous meningeal metastasis of MDA-MB-231. Altogether, the data indicate that miR-105 is a potent regulator of cellular migration by targeting ZO-1, and may partially mediate the enhanced migratory potential of MBC cells.

Cancer-Secreted miR-105 Downregulates Tight Junctions in Epithelial Cells.

Figure 3H:
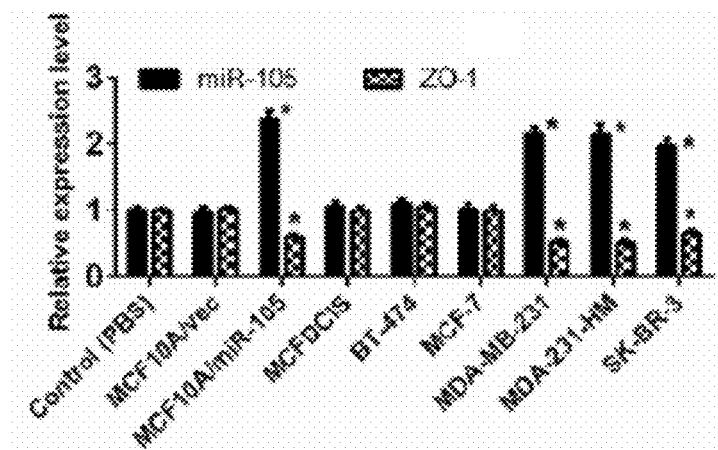
Figures 4A, 4B, 4C:
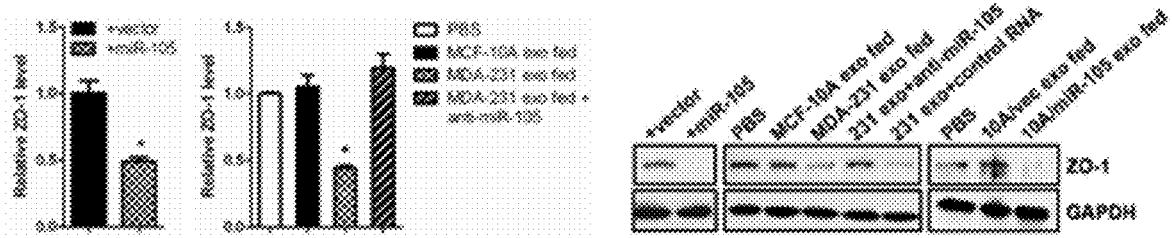
FIGS. 4A, 4B, 4C, 4D, 4E, 4F, 4G, and 4H, show cancer-secreted miR-105 downregulates tight junctions (TJs) in epithelial cells.
Figure 4D:
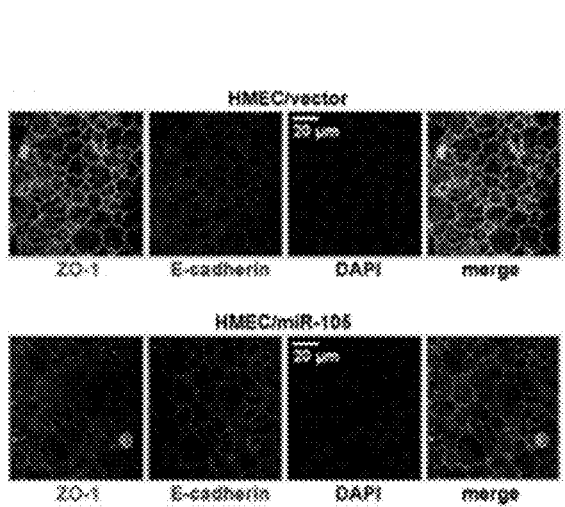
Figure 4E:
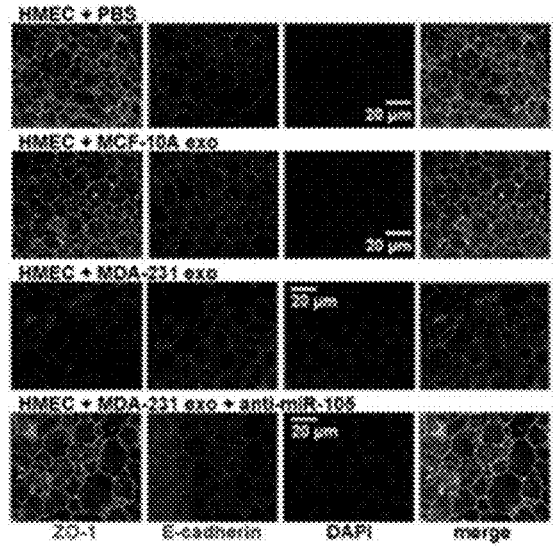
Figure 4F:
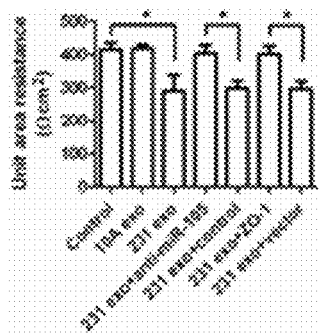
Figure 4G:
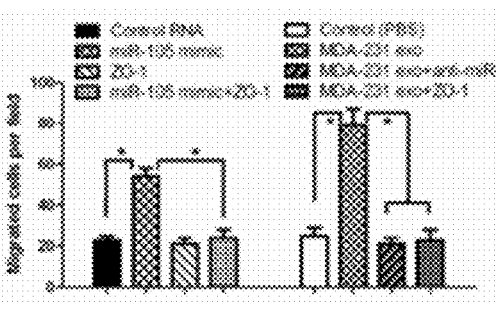
Figure 4H:
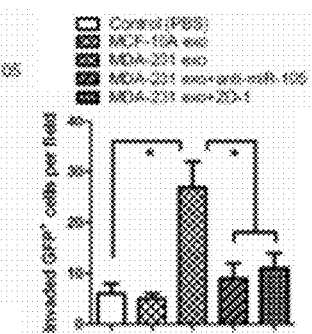

Similar to that observed in cancer lines, ectopic expression of miR-105 in HMECs resulted in a significant decrease of ZO-1 expression at both mRNA and protein levels (FIGS. 4A and 4C). Treatment with exosomes derived from the MDA-MB-231 (high-miR-105) but not the MCF-10A cells (low-miR-105) also reduced ZO-1 expression in HMECs, an effect that could be abolished by transfecting the recipient cells with miR-105 inhibitor (FIGS. 4B and 4C). This was unlikely to require additional exosomal components that are unique to MDA-MB-231, as exosomes secreted by MCF-10A cells stably overexpressing miR-105 (FIGS. 14A, 14B and 14C) and by SK-BR-3 cells (high-miR-105; FIGS. 2A and 2B) but not by BT-474 or MCF-7 cells (low-miR-105; FIGS. 2A and 2B) also downregulated ZO-1 expression in recipient HMECs (FIGS. 3H, 4C and 15A). When HMEC monolayers were analyzed by immunofluorescence, those transfected with miR-105 mimic or treated with MDA-MB-231 exosomes exhibited marked reduction of ZO-1 at the cell junctions, whereas the junctional level of E-cadherin was not significantly affected (FIGS. 4D and 4E). This effect was not observed in HMECs treated with MCF-10A exosomes, or with the MDA-MB-231 exosomes in the presence of miR-105 inhibitor. The transepithelial electrical resistance (TEER) in HMEC monolayers was further measured. Treatment with MDA-MB-231 exosomes significantly reduced the unit area resistance compared to untreated or MCF-10A exosome-treated HMECs. Inhibition of miR-105 and restored expression of ZO-1 in recipient HMECs both abolished the effect of MBC-derived exosomes (FIG. 4F). Consistent with these results, ectopic expression of miR-105 or treatment with MBC exosomes significantly induced migration in HMECs through the miR-105/ZO-1-mediated mechanism (FIG. 4G). Lastly, to directly simulate the barrier-traversing step in metastasis, trans-epithelial invasion of cancer cells was examined using HMEC monolayers grown on 3-μm filters. The number of GFP-labeled MDA-231-HM cells that had invaded through HMECs treated with MDA-MB-231 exosomes was significantly greater compared to those invaded through untreated or MCF-10A exosome-treated HMECs, and both miR-105 inhibition and ZO-1 restoration in recipient cells interfered with this effect (FIG. 4H).

Cancer-Secreted miR-105 Destroys the Barrier Function of Endothelial Monolayer.

Figure 5A:
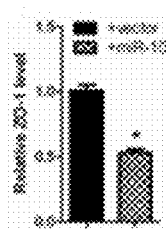
FIGS. 5A, 5B, 5C, 5D, 5E, 5F, 5G, 5H, and 5I, show cancer-secreted miR-105 destroys the barrier function of endothelial monolayer.
Figure 5B:
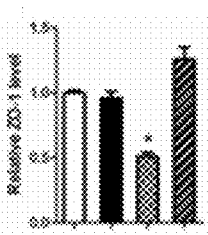
Figure 5C:
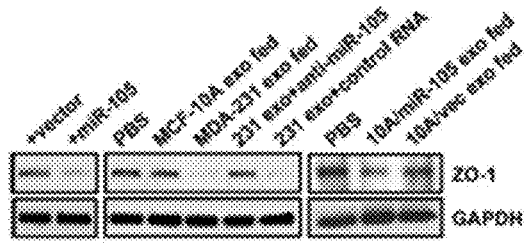
Figure 5D:
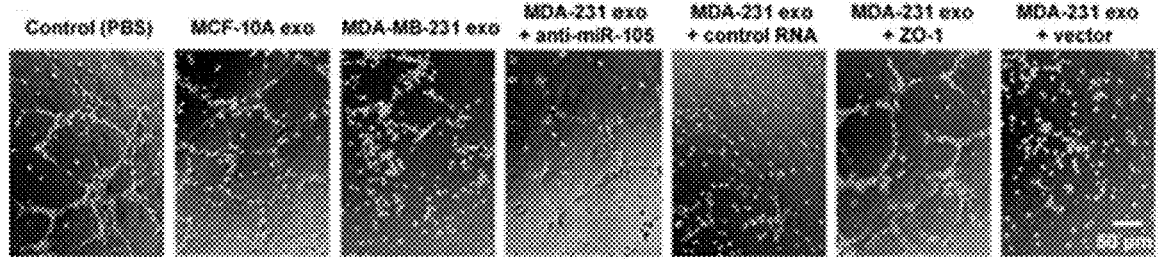

Downregulation of ZO-1 by miR-105 and high-miR-105 exosomes (secreted by MDA-MB-231, MCF10A/miR-105, and SK-BR-3) was also observed in HMVECs (FIGS. 5A, 5B, 5C and 15B). Using a tube formation assay to model endothelial alignment and migration, it was observed that MDA-MB-231-secreted exosomes efficiently disrupted tube formation in HMVECs, which required functional miR-105 and subsequent downregulation of ZO-1 (FIG. 5D).

Figure 5E:
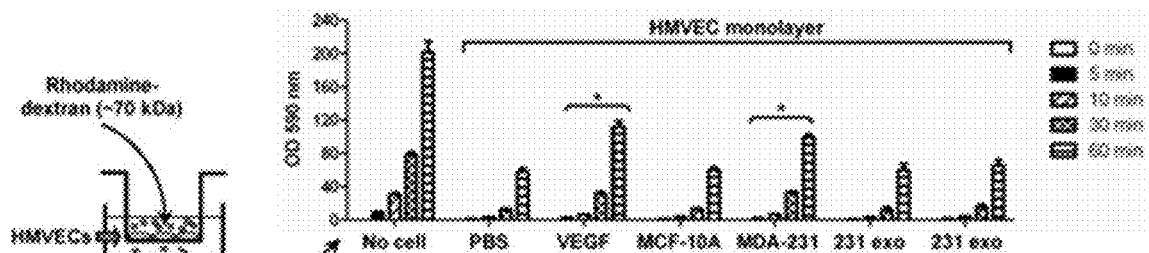
Figures 5F, 5G:
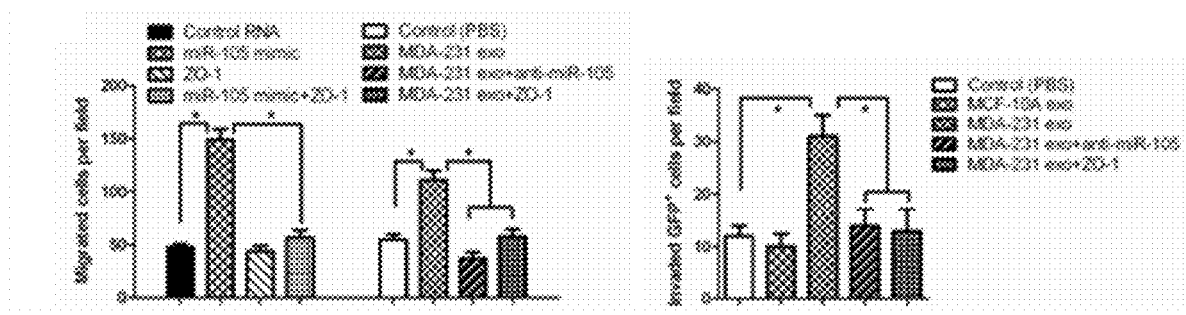
Figures 5H, 5I:
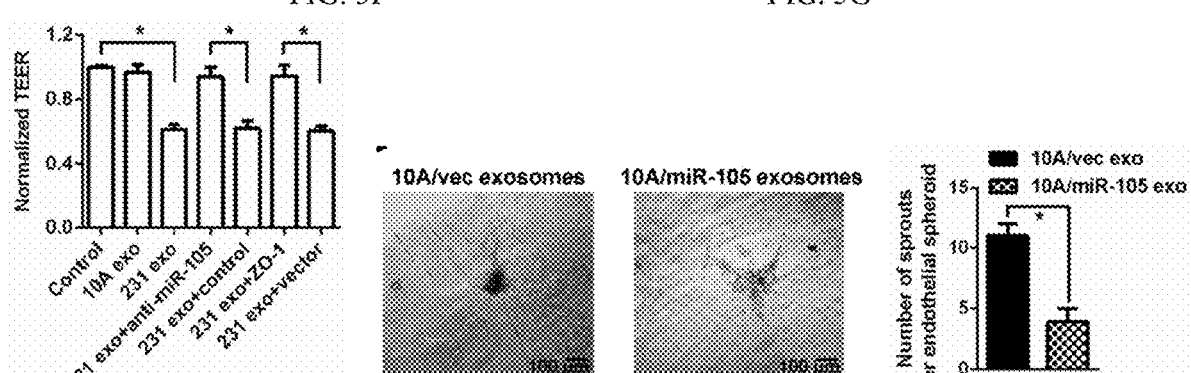

An in vitro permeability assay was performed by measuring the traversing of rhodamine-labeled Mr 70K dextran probes through HMVEC monolayers growing on 0.4-μm filters. Similar to an effect induced by VEGF, treatment of the endothelial barrier with MDAMB-231 exosomes also induced passage of the fluorescent probes from top to the bottom wells in a manner that was dependent on functional miR-105 and downregulation of ZO-1 (FIG. 5E). When the trans-endothelial electrical resistance was measured in HMVEC monolayers, treatment with MDA-MB-231 exosomes significantly reduced the unit area resistance compared to PBS or MCF-10A exosome treatment Inhibition of miR-105 and restored expression of ZO-1 in recipient HMVECs both abolished the effect of MBC-derived exosomes (FIG. 5H). The effect of miR-105-containing exosomes on vascular destruction was further tested in a 3D vascular sprouting assay. In this system, endothelial cells formed vascular sprouts after 4 to 5 days in culture. At this time, purified exosomes from MCF10A/vec (control) or MCF10A/miR-105 cells were added into the culture media, and the effects on already established vascular structures were analyzed 5 days later. A clear and significant destruction of vascular structures was observed with the treatment of miR-105-containing exosomes (from MCF10A/miR-105) compared to the control (FIG. 5I). Consistent with these results, ectopic expression of miR-105 or treatment with MBC exosomes significantly induced migration in HMVECs through the miR-105/ZO-1-mediated mechanism (FIG. 5F). Lastly, to directly simulate the barrier-traversing step in metastasis, trans-endothelial invasion of cancer cells was examined using HMVEC monolayers grown on 3-μm filters. The number of GFP-labeled MDA-231-HM cells that had invaded through HMVECs treated with MDA-MB-231 exosomes was significantly greater compared to those invaded through untreated or MCF-10A exosome-treated HMVECs, and both miR-105 inhibition and ZO-1 restoration in recipient cells interfered with this effect (FIG. 5G).

Cancer-Secreted miR-105 Induces Vascular Permeability and Promotes Metastasis In Vivo.

Figure 20A:
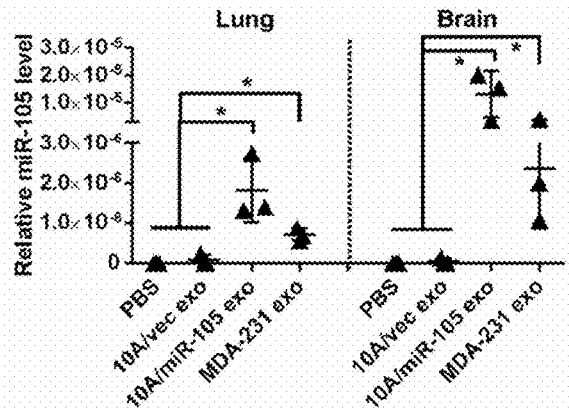
FIGS. 20A, 20B and 20C show cancer-secreted miR-105 induces vascular permeability and promotes metastasis in vivo.
Figure 20B:
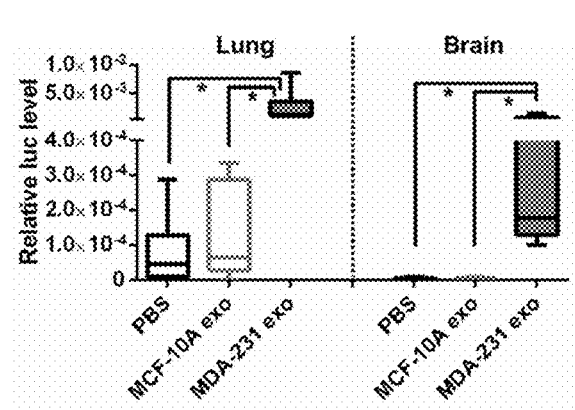
Figure 20C:
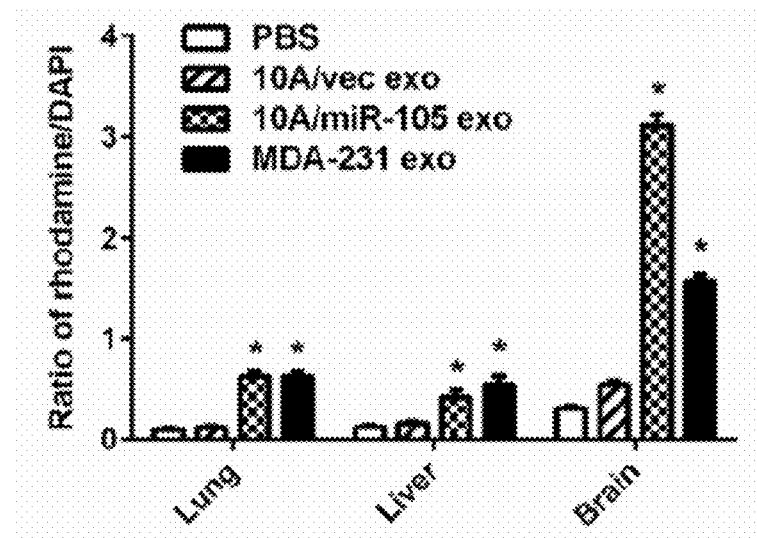

To further demonstrate the in vivo effect of exosomal miR-105 on endothelial barriers, exosomes secreted by MCF10A/vec (low-miR-105), MCF10A/miR-105 (high-miR-105), or MDA-MB-231 cells (high-miR-105), or PBS as control, was injected into the tail vein of NOD/SCID/IL2Rγ-null (NSG) mice and examined lung and brain, organs that frequently host BC metastases, after exosome treatment. The results indicated that exosomes with high-miR-105, but not those with low-miR-105, significantly increased miR-105 levels in lung and brain (FIG. 20A), accompanied by reduced ZO-1 expression in CD31+ endothelial cells and enhanced vascular permeability (FIG. 20C). In another experiment, mice were pretreated with exosomes secreted by MCF-10A or MDA-MB-231 cells (or PBS as control) before an intracardiac injection of luciferase-labeled MDA-MB-231 cells. Three weeks later, tissues were collected for RT-qPCR of luciferase gene using mouse 18S as internal control to quantify metastases. Consistent with their effect on destroying the endothelial barriers, MDA-MB-231, but not MCF-10A exosomes significantly increased metastases in lung and brain (FIG. 20B).

MiR-105 Overexpression Promotes Tumor Invasion and Metastasis In Vivo.

Figures 6A, 6B:
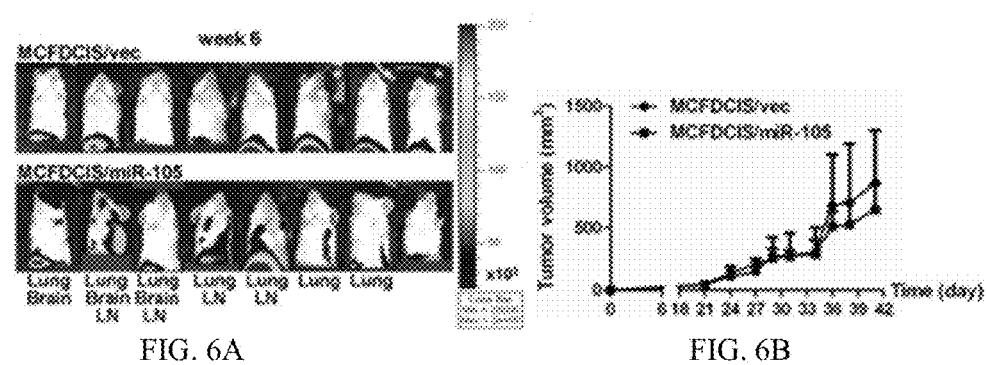
FIGS. 6A, 6B, 6C, 6D, 6E, 6F, and 6G, show miR-105 overexpression promotes tumor invasion and metastasis in vivo.
Figures 6C, 6D:
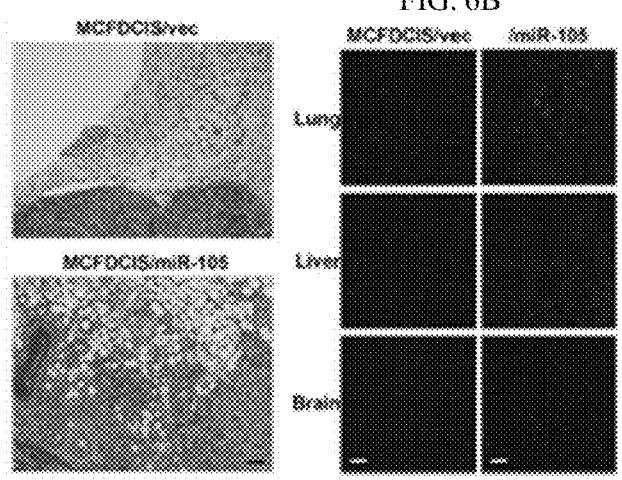
Figure 6E:
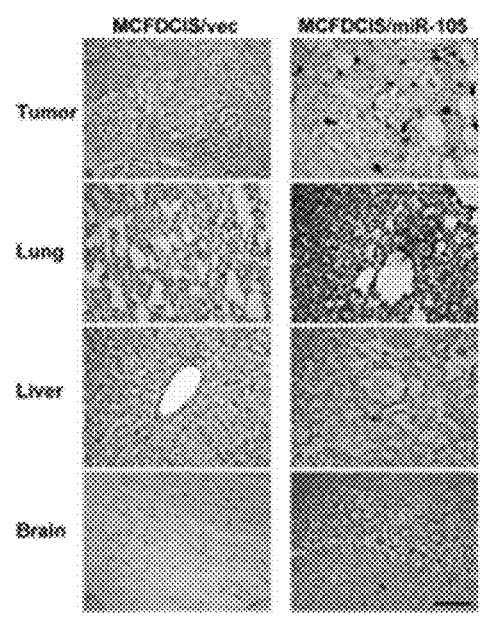
Figure 6F:
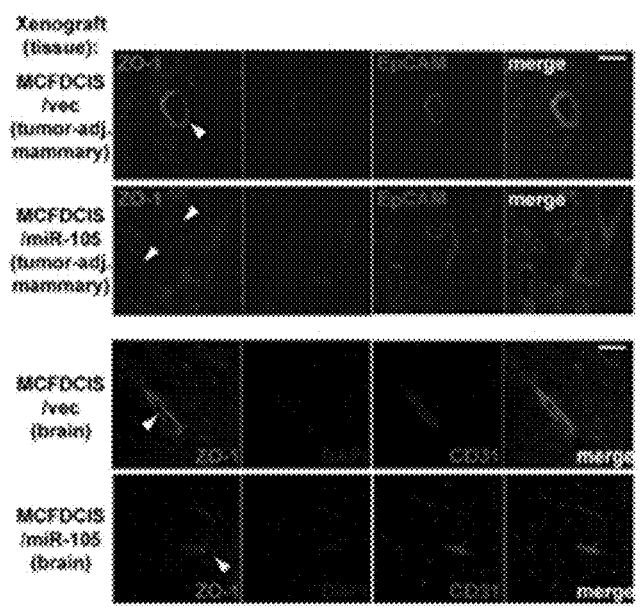
Figure 6G:
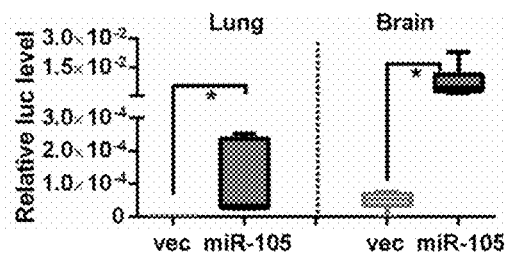
Figures 13A, 13B, 13C:
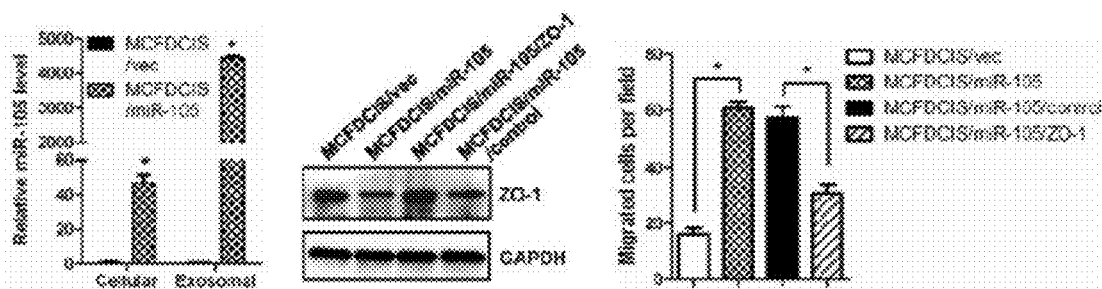
Figure 16B:
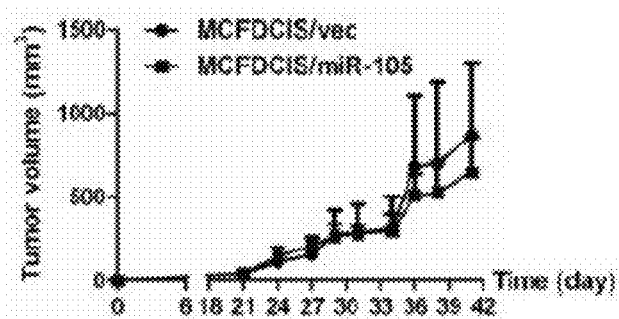
Figure 17A:
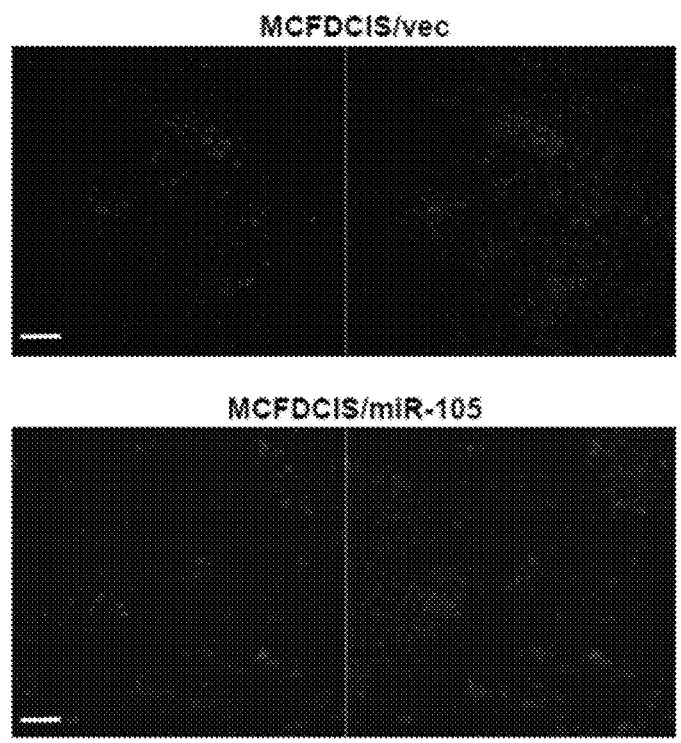
FIGS. 17A and 17B show vascular permeability in primary MCFDCIS xenograft tumors.
Figure 17B:
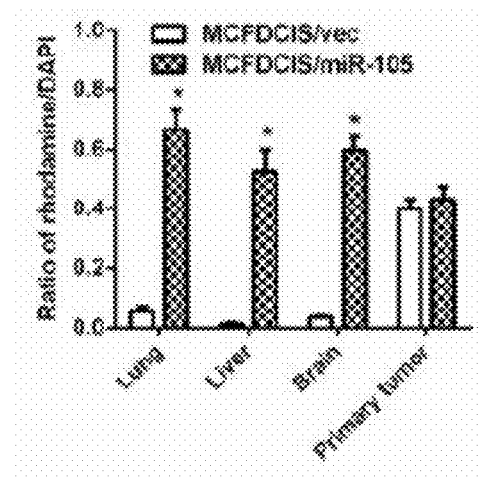
Figure 18:
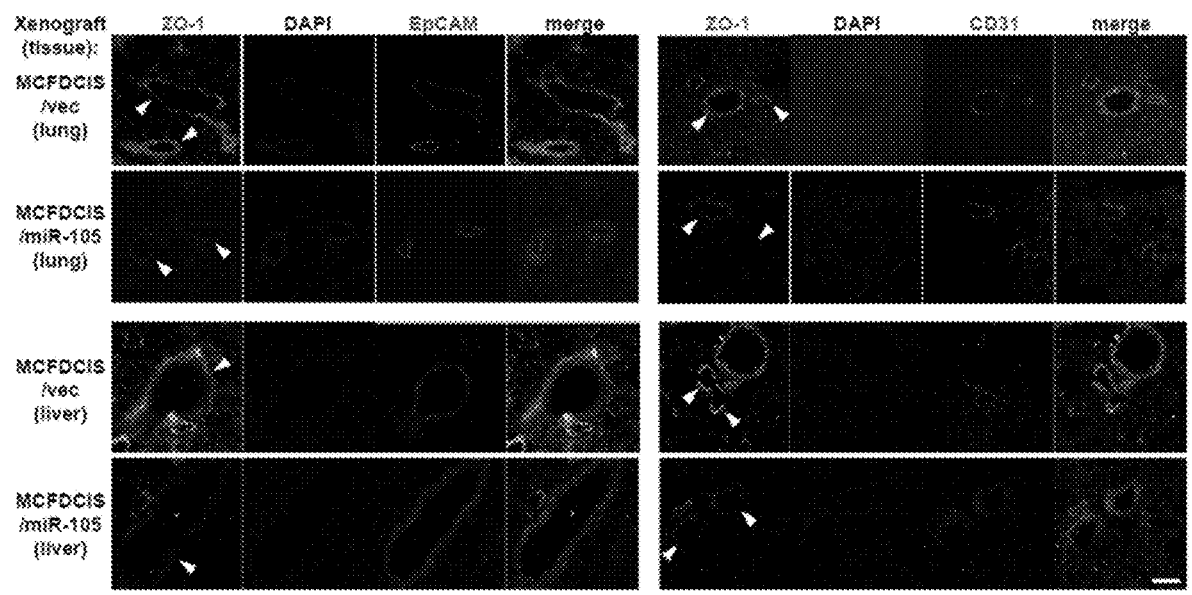
FIG. 18 are images of tissue IF in mice bearing MCFD-CIS xenografts. Collected lung and liver tissues were subjected to double-label IF for ZO-1 and CD31 or EpCAM. DAPI was used for cell nuclei. Structures positive for CD31 or EpCAM are indicated by arrowheads. Bar=100 μm.

To determine if the miR-105 level in primary tumors regulates endothelial barriers and metastasis, miR-105 was stably overexpressed in an MCF-10A-derived tumorigenic line MCFDCIS, which forms comedo ductal carcinoma in situ-like lesions that spontaneously progress to invasive tumors. Compared to vector-transduced control cells, the miR-105-overexpressing MCFDCIS cells also secreted a higher level of miR-105 (FIG. 13A), and showed reduced ZO-1 protein expression and significantly enhanced migration in transwell and wound closure assays (FIGS. 13B, 13C, and 13D). Restoration of ZO-1 using an overexpressing plasmid that lacks the 3'UTR abolished the pro-migratory effect of miR-105. Next orthotopic xenografts were established using luciferase-labeled MCFDCIS cells with or without miR-105 overexpression. Although miR-105 did not seem to affect primary tumor growth (FIGS. 16A and 16B), distant metastases were significantly induced in lung and brain in mice bearing miR-105-overexpressing tumors at week 6 (FIGS. 6A, 6B and 6G). Histological staining indicated that in contrast to the MCFDCIS/vec tumors showing moderate local invasiveness, MCFDCIS/miR-105 tumors displayed no clear margin and extensively infiltrated into the surrounding tissues (FIG. 6C). In addition, the in vivo vascular permeability in lung, liver, and brain of mice bearing miR-105-overexpressing tumors was dramatically increased compared to the control group (FIGS. 6D, 17A, and 17B), whereas a relatively high vascular permeability was observed in the primary tumors of both groups (FIGS. 17A and 17B). In mice bearing miR-105-overexpressing tumors, miR-105 was detected not only in primary tumors but also in the metastasis-free areas of distant organs (FIG. 6E). Reduced level of ZO-1 was observed in the CD31+ vascular endothelial cells in the lung and brain of mice with high-miR-105 xenografts (FIGS. 6F and 18). These results collectively suggest that tumor cells expressing and consequently secreting higher level of miR-105 acquire greater metastatic potential through the dual advantages of enhanced tumor cell invasion and weakened endothelial barriers in the host.

MiR-105 Intervention Suppresses Metastasis and Restores Vascular Integrity In Vivo.

Figure 7A:
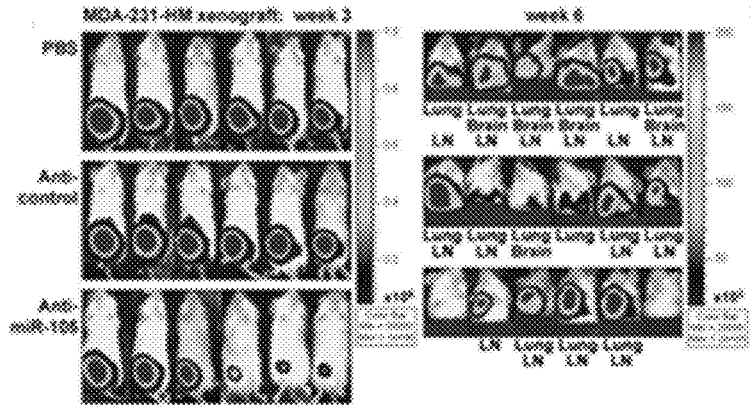
FIGS. 7A, 7B, 7C, 7D, 7E, 7F, 7G, 7H, 7I, and 7J show miR-105 intervention suppresses metastasis and restores vascular integrity in vivo.
Figure 7B:
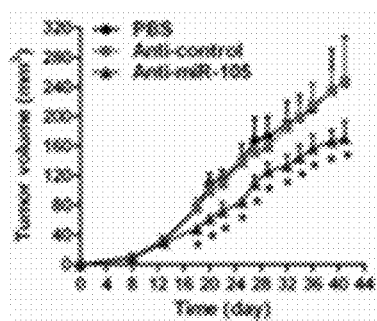
Figure 7C:
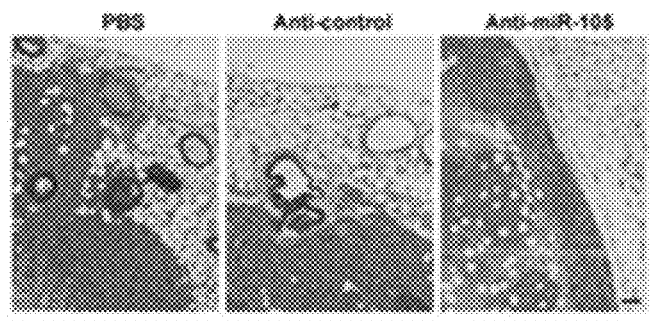
Figure 7D:
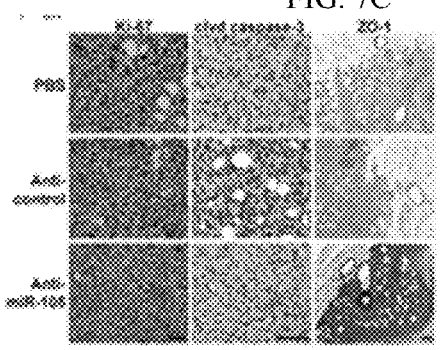
Figure 7E:
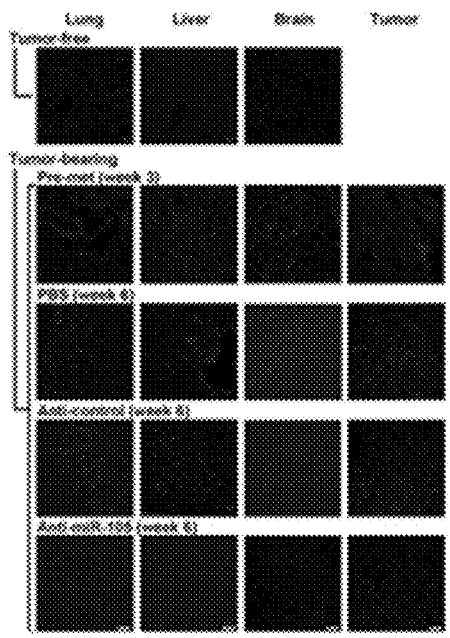
Figure 7F:
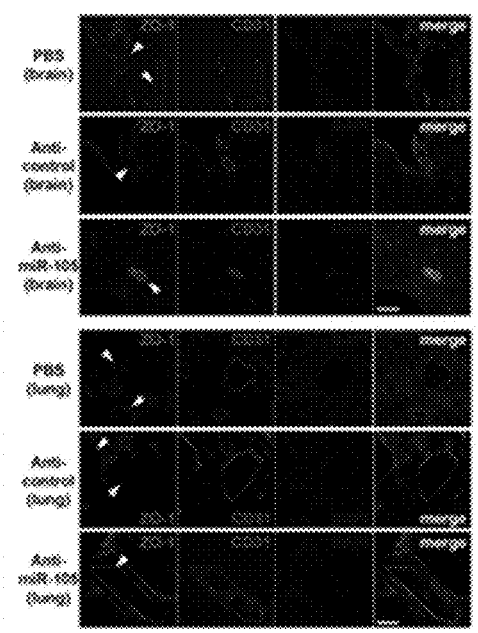
Figure 7G:
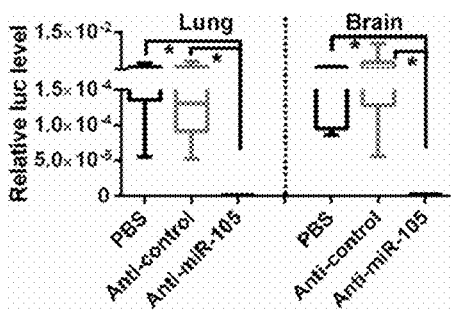
Figure 7H:
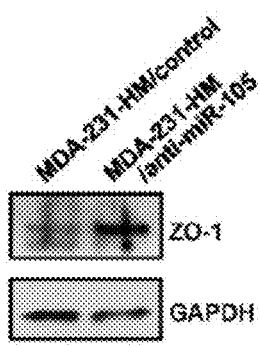
Figure 7I:
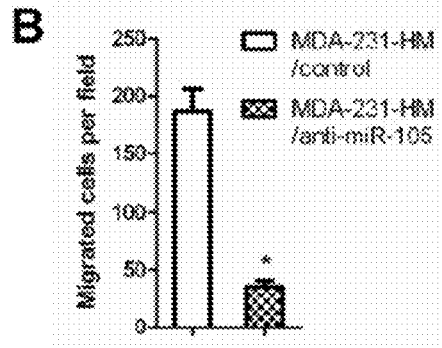
Figure 7J:
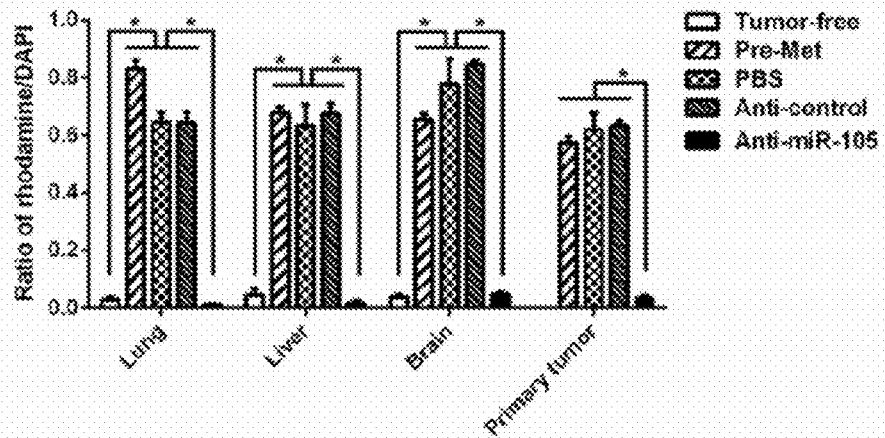

To further explore the potential therapeutic effect of miR-105 intervention, xenografts were established from high-miR-105, high-metastatic MDA-231-HM cells that were generated through explant culture of a spontaneous meningeal metastasis of MDA-MB-231. In vitro treatment of these cells with an anti-miR-105 compound increased ZO-1 expression and suppressed migration (FIGS. 7H and 7I), consistent with the effect of miR-105 observed in other experiments. In vivo treatment with the anti-miR-105 compound reduced the volume of primary tumors and suppressed distant metastases to lung and brain compared to the groups receiving PBS or control compound (FIGS. 7A, 7B, and 7G). Tumors treated with anti-miR-105 had a clear margin with significantly reduced tumor cell infiltration into the surrounding tissues (FIG. 7C). Although Ki-67 staining did not show a significant difference among the tumor groups, anti-miR-105-treated tumors showed a higher level of ZO-1 and a higher percentage of apoptotic cells, as indicated by cleaved caspase-3 (FIG. 7D). The in vivo vascular permeability assay indicated lack of rhodamine-dextran penetration into various tissues in tumor-free mice; conversely, leakage of the dye into these tissues in tumor-bearing animals occurred even at a premetastatic stage (FIGS. 7E and 7J), which suggests an effect of tumor-secreted factors in destroying the vascular integrity of a distant organ during early pre-metastatic niche formation. Notably, treatment with anti-miR-105 efficiently blocked this effect, restoring the vascular integrity in tumor-bearing animals (FIGS. 7E and 7J). Restored ZO-1 expression in CD31+ vascular endothelial cells was observed in the lung and brain of tumor-bearing mice treated with anti-miR-105 compound (FIG. 7F). Thus, anti-miR-105 treatment suppresses metastasis by reducing tumor invasiveness and restoring the barrier function of endothelial niche cells.

MiR-105 is Associated with ZO-1 Expression and Metastatic Progression in BC.

Figure 8A:
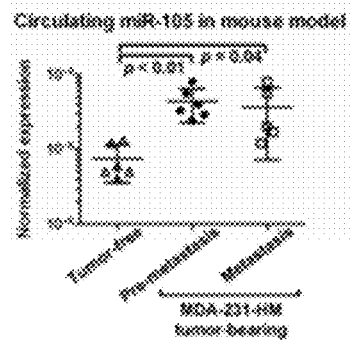
Figure 8B:
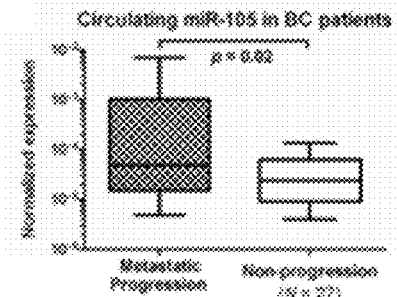

Because miR-105 is uniquely expressed and secreted by MBC cells, it is possible that cancer-secreted miR-105 can be detected in the circulation of BC patients, where miR-105 may serve as a prognostic marker for metastatic potential. To explore this, the serum miR-105 levels were measured in mice bearing MDA-231-HM xenograft tumors at either pre-metastatic (week 3 after cancer cell implantation) or metastatic stages (week 6 after cancer cell implantation) in comparison to tumor-free animals. Circulating miR-105, but not two other miRNAs (miR-155 and miR-275), was significantly elevated in tumor-bearing animals at both pre- and metastatic stages (FIG. 8A and FIG. 8H), suggesting that miR-105 derived from primary tumors with high miR-105 levels and high metastatic potential can be detected in the blood at an early stage before clinical detection of metastasis. The serum miR-105 levels were then compared among 44 stage II-III BC patients. Levels of the circulating miR-105 were significantly higher in patients who later developed distant metastases during the 4.2 years of mean follow-up (N=17) than those who did not (N=27) (FIG. 8B). Further, miR-181a predominantly existed in exosomes while two other miRNAs (miR-375 and miR-422b) were detected in both exosomes and exosome-depleted fraction at comparable levels (FIG. 8K). FIG. 8I shows that, in circulating exosomes, purified from sera levels of miR-105 but not two other miRNAs (miR-181a and miR-375) were significantly higher in patients that later developed distance metastases during the 4.2 years of mean follow-up (n=16) than those who did not (n=22). To further determine if circulating miR-105 in BC patients are functionally active in regulating endothelial cells, 3D vascular structures were treating with serum from a healthy donor or a BC patient with a high level of circulating miR-105. The patient serum but not normal serum resulted in destruction of vascular structures, which was abolished by the anti-miR-105 compound (FIG. 8J). Using a logistic regression model, higher levels of circulating miR-105 predicted metastasis at a sensitivity of 35% (6/17) and specificity of 93% (25/27), with an odds ratio of 1.47 and a 95% confidence interval of 1.08-20.1. In patients with paired serum and tumor specimens, a strong positive correlation was detected between circulating and tumor miR-105 levels (R=0.85, p<0.01). In contrast, strong inverse correlations were detected between tumor miR-105 and ZO-1 (R=−0.48, p=0.03), as well as between circulating miR-105 and tumor-adjacent vascular ZO-1 expression (R=−0.49, p=0.04) (FIGS. 8C, 8D and 8E). These observations are consistent with the role of miR-105 in downregulating ZO-1. In addition, higher levels of tumor miR-105 and lower levels of tumor and vascular ZO-1 were observed in patients who later developed distant metastases compared to those who did not and to normal mammary tissues (FIGS. 8D and 8E). In a BC tissue array, significantly higher miR-105 and lower ZO-1 levels were detected in the primary tumors with distant or lymph node metastases (n=15) compared to those without (n=60), and the inverse correlation between miR-105 and ZO-1 remained significant among all cases (r=−0.24, p=0.04) (FIG. 8G). Overall, the clinical data suggest that cancer-derived miR-105 can serve as a blood-based marker for the prediction or early diagnosis of BC metastasis, and may play a role in promoting cancer progression by targeting ZO-1.

Discussion

Exchange of cellular materials between cells through various mechanisms, such as paracrine and endocrine, is an important means of intercellular communication. Exosomes as a unique type of carrier of proteins, mRNAs and miRNAs for intercellular transfer have attracted increasing attention for their roles in mediating the crosstalk between cancer cells and their hosting niche. Here it is shown that miR-105 is specifically expressed and secreted by BC cells with high metastatic potential. This miRNA induces migration and invasion in cancer cells by targeting ZO-1, and upon exosome-mediated transfer to epithelial and endothelial niche cells, destroys the barrier function of these cells to facilitate metastasis (FIG. 8F). These features of miR-105 make it a target for the prevention and early treatment of metastasis. Indeed, the in vivo data shows that miR-105 intervention reduces the local invasiveness of primary tumor and restores vascular integrity at distant metastatic sites, resulting in a suppression of distant metastasis (FIG. 7). Thus, anti-miR-105 therapy, by simultaneously targeting both the tumor lesion and the systemic barrier-destroying effect of cancer-derived miR-105, may serve as an effective treatment for cancer patients with a high risk of metastasis (e.g., indicated by high levels of circulating miR-105; FIG. 8B), in combination with existing conventional therapies.

The TJ component ZO-1 was identified as a target mediating miR-105's dual effect on cancer and niche cells. In polarized epithelial and endothelial monolayers, TJs are located at the apical-most region of the lateral membrane, and play fundamental roles in the regulation of paracellular permeability (barrier function) and asymmetric distribution of membrane components required for developing membrane polarity (fence function). ZO family members function as TJ-associated scaffolding proteins by anchoring integral membrane TJ proteins, such as occludin and claudin, to the actin cytoskeleton, and by organizing TJ complexes to initiate downstream signal transduction. Downregulation or loss of TJs, frequently as a result of reduced expression of TJ-associated proteins, contributes to cancer progression by altering cell migration, proliferation, polarity, and differentiation (Brennan et al., J. Biomed. Biotechnol. 2010:460607 (2010); Georgiadis et al., PLoS One 5:e15730 (2010); Itoh and Bissell, J. Mammary Gland Biol. Neoplasia 8:449-462 (2003); Martin and Jiang, Biochem. Biophys. Acta 1788:872-891 (2009)). Reduction of TJ-associated ZO-1 in primary breast tumors due to decreased expression or cytoplasmic localization is associated with metastasis in BC patients (Martin et al., Eur. J. Cancer 40:2717-2725 (2004); Polette et al., Cancer Res. 65:7691-7698 (2005)). This application identifies miR-105 as a key regulator of ZO-1, and provide a mechanism of TJ disruption associated with cancer progression and metastasis. In epithelial and endothelial niche cells that normally express low miR-105 levels, ectopic, cancer-derived miR-105 transferred via exosomes can effectively reduce ZO-1 expression and disrupt the barrier function of these cells both in vitro (FIGS. 4 and 5) and in vivo (FIGS. 6 and 7). Although miR-105 secreted by the primary tumor may only affect a fraction of epithelial and endothelial niche cells, this would be sufficient to open "gates" in these natural monolayer barriers for traversal of cancer cells thereby facilitating metastasis. In addition, contact-dependent intercellular miRNA transfer between two adjacent cells through the transmembrane channel protein SIDT1 has recently been reported (Elhassan et al., J. Biol. Chem. 287:5267-5277 (2012)). Through this pathway, cancer-derived miRNAs (e.g., miR-105) that are transferred to a distant organ via circulating exosomes may further extend their regulatory effect to those interconnected niche cells without direct exosome uptake.

MiRNA transfer between cancer cells and the genetically normal niche cells is apparently two-way traffic. In addition to the cancer-derived adaptation of niche cells, normal epithelial cells also secrete and transfer anti-proliferative miRNAs (e.g., miR-143) to cancer cells, as a potential strategy to maintain tissue homeostasis at an early stage in cancer formation (Kosaka et al., J. Biol. Chem. 287:1397-1405 (2012)). In contrast, exosomes secreted by stromal fibroblasts promote BC cell protrusion and motility through Wnt-planar cell polarity signaling (Luga et al., Cell 151: 1542-1556 (2012)). Because exosomes are secreted by multiple types of normal cells and mediate their natural functions such as antigen presentation (Thery et al., Nat. Rev. Immunol., 2:569-579 (2002)), targeting exosome secretion as a potential means of blocking this mode of cancer-host crosstalk requires identification of cancer-specific molecules/pathways that control exosome production. Characterization of cancer-secreted messengers and effectors, such as miR-105, enables selection of patients for the corresponding targeted therapy and eventually combination therapy simultaneously targeting multiple secretory miRNAs and/or proteins. As provided herein patient selection may be achieved by a quantitative blood test for circulating miR-105, which predicts metastasis in early-stage BC patients (FIG. 8B). In developing stage-specific and personalized therapy, a combination of miR-105, optionally with other miRNA and/or protein markers in the blood, will enhance the sensitivity and specificity of selecting patients with a high risk of metastasis for preventive treatment that targets miR-105 and other effectors.

Experimental Procedures

Clinical Specimens.

Human specimens were obtained from voluntarily consenting patients at the City of Hope Medical Center (Duarte, Calif.) under institutional review board-approved protocols. For circulating miR-105 analysis, patients with stage II-III BC at the time of registration were included, including those who developed systemic recurrence while on study and those who had not developed systemic relapse. The two groups were balanced for age, treatment regimen, and sample collection time. The mean follow-up is 4.2 years for the group with disease progression and 4.7 years for the group without at the time of analysis. Exosomes were isolated from serum, and RNA was extracted using TRIZOL LS reagent (Life Technologies; Grand Island, N.Y.) and subjected to reverse transcription-quantitative PCR (RT-qPCR) for miRNAs as described (Wu et al., J. Transl. Med. 10:42 (2012)). For the evaluation of miR-105 and ZO-1 expression using tumor specimens, a cohort including 20 stage II-III BC patients (10 developed systemic recurrence later with a mean follow-up of 3.5 years and 10 did not with a mean follow-up of 4.7 years) that partially overlaps with the serum cohort was studied. Among these, 18 patients had paired serum and tumor specimens available. The BC tissue array (FIG. 8G) was purchased from US Biomax (Cat # BR1505a; Rockville, Md.).

Cells, Plasmids and Viruses.

Human BC cell lines and the non-cancerous cell line MCF-10A were obtained from American Type Culture Collection (Manassas, Va.) and cultured in the recommended media in a humidified 5% $CO_2$ incubator at 37° C. Primary HMECs and HMVECs (from adult dermis) were purchased from Life Technologies and cultured according to the manufacturer's instructions. Primary mouse mammary epithelial cells were purified and cultured as described (Muraoka-Cook et al., Oncogene, 25:3408-3423, (2006)), and primary mouse brain microvascular endothelial cells were purchased from Cell Biologics (Chicago, Ill.). MCF10DCIS.com (MCFDCIS) cells were purchased from Asterand (Detroit, Mich.). The MDA-231-HM cells were generated in our lab through explant culture of a spontaneous meningeal metastasis of MDA-MB-231 BC cells from an immunocompromised mouse. To construct the ZO-1 3'UTR reporter plasmids, annealed oligonucleotides encompassing the putative miR-105 binding sites indicated in FIG. 3A or a scrambled control sequence were inserted into the XhoI/NotI sites of psiCHECK-2 vector (Promega; Madison, Wis.) downstream of the Renilla luciferase gene. The human ZO-1 expression plasmid was kindly provided by Dr. Alan Fanning (University of North Carolina at Chapel Hill). For miR-105 overexpression, the hsa-mir-105-1 gene was cloned by PCR using primers 5'-TGTTTGCCTCCTTCTTCGTC (SEQ ID NO:5) and 5'-ACAGGAACAAATGGCTTTGG (SEQ ID NO:6), and constructed into the BamHI/XhoI sites of pBABE-Puro or pBABE-GFP retroviral vector. Cell transfection, reporter assays, production of viruses, as well as infection and selection of transduced cells were carried out as previously described (Wang et al., Cancer Cell, 10:25-38 (2006); Wang et al., Oncogene, 30:1470-1480 (2011)). MiRIDIAN miR-105 mimic and hairpin inhibitor as well as their corresponding negative controls were purchased from Thermo Fisher Scientific (Waltham, Mass.). MiR-105 labeled with Cy3 at the 3' end was synthesized by Integrated DNA Technologies (Coralville, Iowa). The RNA polymerase II inhibitor 5,6-dichloro-1-β-D-ribofuranoside (DRB) and VEGF were purchased from Sigma (St. Louis, Mo.).

Exosome Purification and Electron Microscopy (EM).

For exosomes secreted by cultured cell lines, conditioned media (CM) was first prepared by incubating cells grown at sub-confluence in growth media containing exosome-depleted FBS (prepared by overnight ultracentrifugation at 100,000×g at 4° C.) for 48 hours and pre-cleared by centrifugation at 500×g for 15 minutes and then at 10,000×g for 20 minutes. Cell-secreted exosomes were purified by ultracentrifugation at 110,000×g for 70 min, and washed in PBS using the same ultracentrifugation conditions. When indicated, DiI (1,1'-Dioctadecyl-3,3,3',3'-tetramethylindocarbocyanine perchlorate; Sigma) was added into the PBS at 1 μM and incubated for 20 min before the washing spin, followed by an additional wash to remove the excess dye. Exosome labeling with PKH67 (Sigma) was performed following manufacturer's procedures. The pelleted exosomes were resuspended in ~100 μl of PBS, and subjected to EM, cell treatment, or RNA extraction using mirVana miRNA isolation kit (Life Technologies) for small RNA extraction in FIG. 1E or TRIZOL LS reagent for all other experiments. For EM, exosomes were fixed with 2% paraformaldehyde, loaded on 200-mesh Formvar-coated grids, and then contrasted and embedded as described in (Thery et al., Nat. Rev. Immunol. 2:569-579 (2006)). The grids were observed under an FEI Tecnai12 transmission electron microscope equipped with a CCD camera. For cell treatment, 2 µg of exosomes (equivalent to those collected from ~$10^6$ producer cells) based on protein measurement using Bradford protein assay (Bio-Rad; Hercules, Calif.) were added to $2 \times 10^5$ recipient cells. Solexa deep sequencing of exosomal RNA and genome-wide interrogation were performed as described (Wu et al., J. Transl. Med. 10:42 (2012)).

RNA extraction, RT-qPCR, Western blot analysis, immunofluorescence (IF), and flow cytometry. These procedures were performed as described previously (Tsuyada et al., Cancer Res. 72:2768-2779 (2012); Wang et al., Oncogene 30:1470-1480 (2011); Yu et al., Mol. Cancer Res. 8:1633-1642 (2010)). Primers used in qPCR are: 5'-ATGGAG-GAAACAGCTATATGGGA (SEQ ID NO:7) and 5'-CCAAATCCAAATCCAGGAGCC (SEQ ID NO:8) for TJPJ (ZO-1), and 5'-CTACCACATCCAAGGAAGCA (SEQ ID NO:9) and 5'-TTTTTCGTCACTACCTCCCCG (SEQ ID NO:10) for 18S rRNA (as internal control for ZO-1). The hsa-mir-105-1 gene cloning primers were used for pri-miR-105 qPCR, and primers for mature miR-105, U6 (as internal control for intracellular miR-105), and pre-miR-105 were purchased from Qiagen (Valencia, Calif.). An annealing temperature of 55° C. was used for all primers. ZO-1 and E-cadherin antibodies were purchased from Santa Cruz Biotechnology (Santa Cruz, Calif.), CD31 and EpCAM antibodies from eBioscience (San Diego, Calif.), and GAPDH antibody from Cell Signaling (Danvers, Mass.).

TEER measurement, endothelial tube formation and permeability assays and 3D vascular sprouting assays. Treated HMEC monolayers grown on 0.3 cm$^2$ polyethylene terephthalate transwell filters (0.4-µm pore size; BD Biosciences; Franklin Lakes, N.J.) were analyzed for TEER using an EVOM2 epithelial voltohmmeter (World Precision Instruments; Sarasota, Fla.). Unit area resistance was calculated following the manufacturer's instructions. Three filters were used for each treatment. For the endothelial tube formation assay, 8-well chamber slides were coated with growth factor reduced Matrigel (BD Biosciences) and treated HMVECs were plated at $2 \times 10^4$ cells/well. After 4 h incubation at 37° C., tube formation was assessed under a microscope. The permeability of treated HMVEC monolayers grown on transwell filters (0.4-µm pore size; BD Biosciences) was assessed by the passage of rhodamine β isothiocyanate-dextran (average MW 70,000; Sigma). Briefly, rhodamine-dextran was added to the top well at 20 mg/ml, and the appearance of fluorescence in the bottom well was monitored by measuring 40 µl medium aliquots in a time course using a SpectraMax microplate reader (Molecular Devices; Sunnyvale, Calif.) at 544 nm excitation and 590 nm emission. Vascular sprouting assay was performed as described using microcarrier-beads coated with endothelial cells and embedded in 3D fibrin gel (Newman et al., Mol. Biol. Cell, 22:3791-3800 (2011)). Briefly, HMVECs were coated on microcarrier-beads in EGM2 medium for 24 hours, followed by embedding the beads into 3D fibrin gel in a 24-well plate, and overlaid with normal human lung fibroblasts in 300 µl of EGM2 medium. The cells were incubated at 37° C. with 5% $CO_2$.

Wound closure, transwell migration, and trans-epithelial/endothelial invasion assays. Wound closure and transwell migration assays were performed as previously described (Wang et al., Cancer Cell, 10:25-38 (2006)). For the trans-epithelial/endothelial invasion assay, pre-treated HMECs or HMVECs were plated and allowed to reach confluence for 3 days on collagen-coated transwell filters (3-µm pore size; BD Biosciences). GFP-labeled MDA-231-HM cells (with pBABE-GFP retrovirus) were seeded into transwell inserts at 50,000 cells per well. After 10 hours, cells on the top side of inserts were scraped off and the transwell filters were examined under an IX81 inverted fluorescent microscope (Olympus; Center Valley, Pa.) for invading GFP$^+$ cells.

Animals.

All animal experiments were approved by the institutional animal care and use committee at City of Hope. For exosome treatment experiments, exosomes secreted by MCF10A/vec, MCF10A/miR-105, or MDA-MB-231 cells, or PBS (as control), were intravenously injected into the tail vein of 6-week-old female NSG mice (2 µg exosomes per injection; two injections per week). After 5 injections, mice were either sacrificed for tissue collection and assessments, or subjected to intracardiac injection of 1×105 luciferase-labeled MDA-MB-231 cells. For xenograft experiments, luciferase-labeled cells (2×105 MCFDCIS or MDA-231-HM) were injected into the No. 4 mammary fat pad of 6-week-old female NSG mice. Weekly bioluminescence imaging (BLI) was carried out using a Xenogen system (Caliper Life Sciences; Alameda, Calif.). When tumors became palpable, tumor volume was assessed by caliper measurements using the formula (width2×length)/2 (mm3). For the miR-105 intervention study, mice were divided into 3 groups for treatment with PBS, an anti-miR-105 compound or a control compound of a sequence that does not target any miRNA. The control and miR-105 targeted compounds had the same chemical modification pattern, chimeric 2'-fluoro and 2'-methoxyethyl modifications on a phosphorothioate backbone (Davis et al., Nucleic Acids Res. 34:2294-2304 (2006)) and were synthesized at Regulus Therapeutics (San Diego, Calif.). At first, compounds (25 mg/kg) were intraperitoneally injected daily for 5 days starting at day 3 after cancer cell implantation, and then twice weekly until the end of experiment. The same compounds were also used in vitro to transfect MDA-231-HM cells in FIGS. 7H and 7I. For in vivo vascular permeability assay, 100 mg/kg rhodaminedextran (average MW ~70,000) was intravenously injected 3 hr before a transcardiac perfusion was carried out to remove the excess dye. Tissues were formaldehyde-fixed and paraffinembedded for hematoxylin and eosin (H&E) stain or embedded in Tissue-Tek O.C.T. Compound (Sakura; Torrance, Calif.) to make frozen blocks for sectioning and fluorescent microscopy. For serum miRNA analysis, blood was collected through cardiac puncture and fractionated by centrifugation, and serum RNA was extracted using TRIZOL LS.

In situ hybridization (ISH) and immunohistochemistry (IHC). IHC staining was performed as previously reported (Tsuyada et al., Cancer Res. 72:2768-2779 (2012)). ISH was performed in formaldehyde-fixed, paraffin-embedded tissue sections using miRCURY LNA™ microRNA ISH optimization kit and the miR-105 detection probe (Exiqon; Woburn, Mass.) by following the manufacturer's protocol. Probes for U6 and a scrambled sequence were used as positive and negative controls, respectively. IHC staining was performed as previously reported (Tsuyada et al., Cancer Res. 72:2768-2779 (2012)) using human Ki-67 (Clone MIB-1; Dako; Carpinteria, Calif.), cleaved caspase-3 (Cat #9661; Cell Signaling), and ZO-1 (Cat # sc-10804; Santa Cruz Biotechnology). Stained slides were scored according to intensity of staining (−: 0; +: 1; ++: 2; and +++: 3) and percentage of the cells of interest staining positive for each antigen (0%: 0; 1~29%: 1; 30~69%: 2; and ≥70%: 3). The intensity score was multiplied by the percentage score to obtain a final score, which was used in the statistical analyses.

Statistical Analyses.

All quantitative data are presented as mean±standard deviation (SD). All results were confirmed in at least three independent experiments, and data from one representative experiment was shown. The statistical analysis was performed using SAS 9.2 software package. Student t tests were used for comparison of means of quantitative data between groups. The association between differential levels of circulating miR-105 and having metastatic disease progression (as outcome) were analyzed using a logistic regression model. The correlations between serum and tumor miR-105 and between miR-105 and ZO-1 expression were evaluated by Pearson correlation coefficient (R). Values of p<0.05 were considered significant.

Example 2. De Novo Sequencing of Circulating miRNAs Identifies Novel Markers Predicting Clinical Outcome of Locally Advanced Breast Cancer Breast cancer (BC) is the most common cancer among females and a leading cause of cancer death worldwide. Current clinical decision-making for BC treatment relies on tumor characteristics and therapeutic targets including the estrogen receptor (ER), progesterone receptor (PR), and human epidermal growth factor receptor 2 (HER2). Chemotherapy is given in the neoadjuvant and adjuvant settings to patients with locally advanced/high-risk primary BC as treatment for metastatic BC leading to life-threatening parenchymal disease, or to treat endocrine resistant (ER/PR-negative) metastatic BC (Guarneri V, Conte P: *Oncologist* 2009, 14:645-656; Guarneri V, et al., *Cancer Lett* 2007, 248:175-185). Neoadjuvant chemotherapy (NCT) is increasingly being used for initial treatment of locally advanced and inflammatory BCs. Pathologic complete response (pCR), defined as the preoperative eradication of tumors from the breast and axillary lymph nodes (Symmans et al., *J Clin Oncol* 2007, 25:4414-44224), is associated with optimal clinical outcome, including improved disease-free and overall survival (Alm El-Din M A, Taghian A G, *Semin Radiat Oncol* 2009, 19:229-235; Specht J, Gralow J R *Semin Radiat Oncol* 2009, 19:222-228). However, conventional NCT regimens result in pCR in only 10-30% of treated BC patients. In patients with residual invasive disease after NCT, a substantial proportion experience disease progression to metastatic stage within a few years after surgical resection. Patients with both de novo and recurrent metastatic BC face poor prognosis, with a median survival of 1-2 years and a 5-year survival rate <20% (Nicolini A, et al., *Biomed Pharmacother* 2006, 60:548-556; Rubens R D. *Int J Clin Pract* 2001, 55:676-679; Yardley D A *Clin Breast Cancer* 2010, 10:64-73). Development of early diagnostic markers capable of predicting a patient's response to therapy and recurrence with metastatic BC is therefore critical to advancing more effective, personalized treatment. In this example, the use of circulating miRNAs as blood-based, minimally invasive biomarkers for NCT response and disease relapse in locally advanced and inflammatory BC patients was explored.

MiRNAs are naturally-occurring, non-coding small RNA molecules of 21-24 nucleotides (nts) that form partially complementary base pairs within the 3' untranslated regions of protein-encoding mRNAs, resulting in mRNA destabilization and/or translational inhibition (Bartel D P *Cell* 2004, 116:281-297). To date, approximately 1000 miRNAs have been identified in humans. Compared to the large number of mRNA genes (~30,000 mRNAs per cell), this relatively small number of miRNAs allows for large-scale evaluation for individualized diagnosis and treatment with higher efficiency and lower cost. Increasingly, reports demonstrate applications of miRNAs as tissue-based markers for the classification and prognosis of several human cancers, including BC (Calin G A, Croce C M *Nat Rev Cancer* 2006, 6:857-866; Iorio M V, et al: *Cancer Res* 2005, 65:7065-7070; Calin G A, et al., *PNAS* 2004, 101:2999-3004; Fu, et al., *J Cancer* 2011, 2:116-122). A number of miRNAs have been found differentially expressed between BC and normal tissues, with significant up- (e.g., miR-21 and miR-155) or down-regulation (e.g., miR-10b and miR-145) in cancerous tissues (Iorio M V, et al., *Cancer Res* 2005, 65:7065-7070; Blenkiron C, et al., *Genome Biol* 2007, 8:R214; Mattie M D, et al., *Mol Cancer* 2006, 5:24). Expression of certain BC-related miRNAs has been correlated with specific biopathologic features, such as ER and PR expression, tumor stage, vascular invasion, and proliferation index (Iorio M V, et al., *Cancer Res* 2005, 65:7065-7070; Fu S W, et al., *J Cancer* 2011, 2:116-122; Blenkiron C, et al., *Genome Biol* 2007, 8:R214; Mattie M D, et al., *Mol Cancer* 2006, 5:24; Maillot G, et al., *Cancer Res* 2009, 69:8332-8340; Fassan M, et al., *Breast Cancer Res* 2009, 11:R58).

MiRNAs are stably present in whole blood, serum, and plasma. Therefore, assessment of circulating miRNA profiles from cancer patients allowing for correlations between tumor traits (e.g., treatment response and metastatic potential) and cancer-released miRNAs are of great clinical interest. Using PCR assessments of selected miRNAs that are reportedly dysregulated in BC, several recent studies indicate associations of different circulating miRNAs with primary BC, metastatic disease, and ER status (Asaga S, et al., *Clin Chem* 2011, 57:84-91; Heneghan H M, et al., *Ann Surg* 2010, 251:499-505; Pigati L, et al., *PLoS One* 2010, 5:e13515; Roth C, et al., *Breast Cancer Res* 2010, 12:R90; Zhu W, et al., *BMC Res Notes* 2009, 2:89). Microarray-based profiling has also been carried out in pilot studies, in which certain circulating miRNAs exhibit promising role as BC diagnostic markers (Lodes M J, et al., *PLoS One* 2009, 4:e6229; Zhao H, et al., *PLoS One* 2010, 5:e13735). Results from these previous studies, however, share limited consistency, possibly due to the different sensitivity and specificity of the detection approaches, as well as different patient numbers and compositions in the study cohorts.

Because some miRNAs may exclusively exist in the circulation with low or undetectable levels in cancer cells, powerful discovery approaches, such as deep sequencing analysis, may be more likely to identify diagnostic miRNA markers in the blood. Accordingly, the potential of deep sequencing was explored in the current example to comprehensively analyze miRNAs that can serve as blood-based markers for NCT response and relapse with metastasis. As the first exploration to profile circulating miRNAs in BC patients using a de novo sequencing strategy, this example revealed global patterns of circulating miRNAs, and led to the identification of miRNA markers that can predict clinical outcome in primary stage II-III BC.

Methods

Study Cohort and Validation Cohort

Patients at City of Hope Medical Center (COH) had given informed consent before blood sera were collected under Institutional Review Board (IRB)-approved protocols, aliquoted and stored at −80° C. until use.

Serum specimens of the training cohort were obtained as part of an NCT clinical trial conducted at COH. Forty-two female stage II-III BC patients deemed appropriate for NCT at the time of diagnosis were collected between December 2005 and April 2009. Upon diagnosis, all patients received conventional chemotherapy lasting 4-6 months followed by surgical resection of the tumor. Among the 42 patients, 7 received docetaxel/doxorubicin/cyclophosphamide (TAC) treatment regimen (group A), and 12 received doxorubicin/cyclophosphamide (AC) treatment followed by carboplatin and nab-paclitaxel (group B). The other 23 patients had $HER2^+$ BC, and were given the same regimen as for group B but with addition of trastuzumab (group C). One of the $HER2^+$ patients was likely stage IV based on presence of pleural effusion at diagnosis, which later was documented to be malignant. Biopsies of the primary tumor were analyzed for pathological classification. Upon completion of NCT, patients with Symmans residual cancer burden (RCB) score (Symmans W F, et al., *J Clin Oncol* 2007, 25:4414-4422) of 0 were defined as pathologic complete response (pCR), whereas those with RCB score of ≥1 were defined as non-pCR. In the training cohort, 11 patients from all 3 treatment groups relapsed with metastatic disease within 1.5 years after serum collection, whereas the other 31 patients have not had disease progression to date during 2-5 years of follow-up. Patients with or without metastatic progression exhibit balanced age, tumor subtype, sample collection time and treatment regimen.

For the testing cohort, patients were selected from the COH Circulating Breast Cancer Tumor Marker Registry, an observational cohort study that recruits women with a variety of breast tumor histologies at the time of diagnosis, collects pretreatment biospecimens, and follows them throughout their clinical course, recording patient and tumor characteristics, treatments delivered, and clinical outcomes. Patients who had stage II-III BC at the time of registration who developed systemic recurrence while on study were defined as cases (N=9). Eight of these had sufficient serum RNA for inclusion in the study. Controls were matched for 2:1 (N=18) from the remaining stage II-III BC patients who had not developed systemic relapse on study and who had been followed at least as long as the case. All controls had sufficient serum RNA for the study. Other matching characteristics included age at diagnosis, hormone receptor and HER2 expression, and lymph node involvement. These patients were recruited onto the parent study between July 2006 and May 2010, a similar era to the training cohort; however, as an observational cohort, their systemic therapy regimen was determined by their primary oncologist. Half of the patients received a similar regimen to the training cohort, including a taxane with either doxorubicin, cyclophosphamide, and/or carboplatin, plus trastuzamab if their tumor was $HER2^+$. The remaining individuals received a hormonal regimen for $ER^+HER2^-$ BC. All therapies were delivered in the adjuvant rather than neoadjuvant setting; therefore, metastatic relapse was the only measurable clinical outcome in this group. Mean follow-up for the testing cohort was 5.8 years.

RNA Purification from Serum

TRIZOL LS reagent (Invitrogen) was used to extract total RNA from ~1.5 ml of serum, as described in the manufacturer's protocol. RNA pellet was dissolved in 10 μl of RNase-free water, and subjected to deep sequencing and qRT-PCR as described below.

Solexa Deep Sequencing for Small RNAs

Each serum sample was independently subjected to library preparation and deep sequencing. All small RNAs of 15-52 nts were selected and sequenced using the Solexa system, following the manufacturer's protocol (Illumina Inc., San Diego, Calif.). Library preparation, as well as cluster generation and deep sequencing, was performed according to the 5' ligation-dependent (5' monophosphate-dependent) manufacturer's protocol (Digital Gene Expression for small RNA; Illumina, Inc., San Diego, Calif.). For each sample, 5 μl of total RNA extracted from serum was used for small RNA library preparation. Small RNAs were size-selected between 17 and 52 nt according to the single-stranded DNA marker in the small RNA sequencing kit (Illumina). The library was quantified using picoGreen and qPCR. Sequencing was performed on a Genome Analyzer IIx (Illumina), and image processing and base calling were conducted using Illumina's pipeline.

MiRNA-Directed and Genome-Wide Interrogation of Identified Sequences

Sequenced reads from Solexa were first mapped onto human genome version hg18 using novoalign software and the expression level of mature miRNAs in the miRBase human miRNA database v15 was summarized as described before (Weng L, et al., *J Pathol* 2010, 222:41-51). Normalization and identification of differentially expressed miRNAs between groups were carried out using Bioconductor package "edgeR" (Robinson M D, et al., *Bioinformatics* 2010, 26:139-140).

Reverse Transcription (RT) and Real Time Quantitative PCR (qPCR)

For qRT-PCR assays, 5 μl of total RNA extracted from serum was used as input into the RT reaction. RT was carried out using the miScript Reverse Transcription Kit (Qiagen) according to the manufacturer's protocol. For qPCR amplification, RT product was combined with PCR assay reagents containing miScript Primer Assay, Universal Primer, and SYBR Green PCR Master Mix (Qiagen). Real-time qPCR was carried out on a BioRad iQ5 thermocycler.

Statistical Analyses

Sequence data analysis and statistical comparisons were carried out using Bioconductor packages and an in-house developed analysis pipeline using R statistical environment. After mapping the deep sequencing data onto the human genome and counting the reads for the mature miRNAs in the miRBase database, raw miRNA expression data were quantile normalized and log 2 transformed with offset of 1. Predictive miRNA classifiers for clinical outcome (the miR-375/miR-122 two-gene signature, and each gene individually) in the NCT training cohort was evaluated using univariate logistic regression and leave-one-out cross-validation. Briefly, one sample was left out as the test sample, and the remaining 31 samples served as the training set and used to train a univariate logistic regression model using the two-gene signature, which was then used to predict the status of the left out sample. If the predicted probability from the logistic regression model is more than a cutoff determined by minimizing the prediction error rate of training samples, the predicted status of that sample would be assigned as "relapsed", or "non-relapsed" otherwise. The predicted classification was then compared to the observed relapse status using 2-by-2 tables, from which sensitivity and specificity were calculated. This procedure was then repeated for each of the two single gene markers. To evaluate the performance of the two-gene signature in predicting the independent validation cohort, the entire NCT cohort (32 samples with RT-PCR data) was used as a training set. Odds ratio and 95% confidence internal were calculated using univariate unconditional logistic regression to determine if the histopathological parameters and circulating miRNAs were associated with NCT response.

Results

Study Design, Deep Sequencing and Annotation Strategy

To comprehensively profile all small RNA species in the circulation, total RNA was isolated from ~1.5 ml serum collected from BC patients at initial diagnosis (prior to NCT), and small RNAs of 15-52 nts was selected for library preparation and deep sequencing. The profiling study involved 42 stage II-III BC patients who participated in a clinical trial comparing docetaxel, doxorubicin, cyclophosphamide versus doxorubicin and cyclophosphamide, followed by nab-paclitaxel and carboplatin. All patients signed voluntary informed, IRB-approved consent forms, and were treated with NCT at the City of Hope Medical Center (ClinicalTrials.gov; NCT00295893). Among them, 11 relapsed with metastatic disease progression to stage IV during the follow-up, and the other 31 non-progressive control cases had matched ages, tumor subtypes and follow-up time, thus comprising the study cohort for metastatic relapse. The 23 HER2$^+$ patients received the trastuzumab-containing NCT regimen, upon which comparable numbers of pCR (12 cases; 52%) and non-pCR (11 cases; 48%) were observed. Correlation of miRNAs to NCT response and metastatic relapse was examined (see Methods below).

Total sequence reads obtained from each serum sample were first aligned to human genome database NCBI36/hg18 to overview the composition of circulating small RNAs and to identify known RNA species. Among aligned reads (~7-12 million) in all sequenced samples, miRNAs represented ~50% of all read counts. Other detected small RNA populations included tRNA (~28%), small cytoplasmic RNA (scRNA; ~8.8%), rRNA (~4.4%), small nuclear RNA (snRNA; ~0.6%), and small nucleolar RNA (snoRNA; ~0.4%), etc.

Identification of Circulating miRNAs Associated with Clinical Parameters

Figure 19A:
FIGS. 19A and 19B show miRNAs detected in circulation.
Figure 19B:
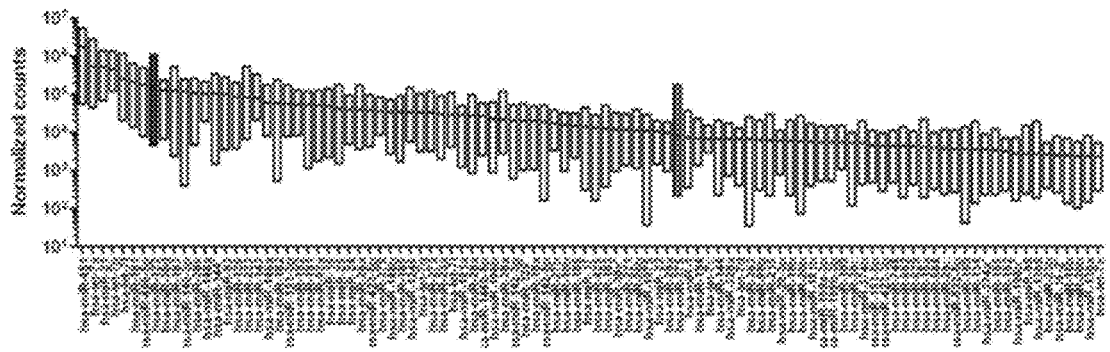

MiRNAs were assessed and were deemed detectable if seen in at least 2 patients. This resulted in detection of more than 800 miRNAs, including 373 miRNAs with sequence counts of >50 in at least 10% of the samples. Unsupervised hierarchical clustering of these miRNAs detected in the circulation separated ER$^+$ from ER$^-$ cases (FIGS. 19A and 19B). No perfect separation was observed between relapsed and non-relapsed cases at the global level. The top 100 circulating miRNAs with the highest average counts among all tested patients are indicated in FIG. 19B. These include several miRNAs that had been measured by PCR in previous studies, such as miR-21, let-7a, miR-155, and miR-10b, as well as miR-375 and miR-122, two genes were subsequently identified as outcome-associated genes.

The association of each miRNA with a given clinical parameter, i.e., status of relapse, NCT response, ER/PR/HER2 expression or inflammatory disease, was analyzed. Multivariate comparison, taking into account the different NCT regimens the patients received, led to the identification of two miRNAs, miR-375 and miR-122, that were differentially expressed between patients who later developed metastatic relapse and those who did not, with P<0.005 and false discovery rate (FDR)<0.1 (Table 1). Because only 2 HER2$^-$ patients in the whole 42-patient cohort had pCR to NCT, the comparison on treatment response was only carried out among HER2$^+$ patients, all of whom received the same trastuzumab-containing NCT regimen. Seven (7) miRNAs were identified that were associated with NCT response (pCR vs. non-pCR) in HER2$^+$ patients with FDR<0.1 (Table 1). Of note, miR-375 was identified in both analyses as the most significantly different miRNA, whose prevalence in circulation appeared to reflect better clinical outcome, i.e., pCR to NCT and absence of relapse. In addition to the clinical outcome, miRNAs associated with the biopathological characteristics of primary BC were also identified. A partial list (FDR<0.05) of miRNAs significantly correlated with the status of ER, PR, HER2 and inflammatory BC is indicated in Table 2. Higher levels of circulating miR-375 were linked to negative ER/PR status, positive HER2 status, and inflammatory BC, whereas higher levels of circulating miR-122 were associated with HER2-negative and non-inflammatory tumors (Tables 2).

TABLE 1

Circulating miRNAs associated with clinical outcome in stage II-III BC patients*

Metastatic Relapse in All patients in the Study Cohort

| Game name | Relapsed (N = 11) Ave. counts (normalized) | Non-relapsed (N = 31) Ave. counts (normalized) | Log fold diff. (relapsed vs. non-relapsed) | P value |
|---|---|---|---|---|
| hsa-miR-375 | 2,177 | 14,316 | −1.90 | 5.89E−05 |
| hsa-miR-122 | 532,501 | 168,532 | 1.35 | 2.98E−03 |

NCT Response in HER2$^+$ Patients

| Game name | pCR (N = 12) Ave. counts (normalized) | Non-pCR (N = 11) Ave. counts (normalized) | Log2 fold diff (pCR vs. non-pCR) | P value |
|---|---|---|---|---|
| hsa-miR-375 | 32,629 | 4,014 | 3.02 | 1.10E−09 |
| hsa-miR-184 | 245 | 31 | 2.99 | 2.59E−09 |
| hsa-miR-1299 | 454 | 89 | 2.35 | 1.24E−06 |
| hsa-miR-196a | 989 | 239 | 2.05 | 1.79E−05 |
| hsa-miR-381 | 384 | 1,235 | −1.69 | 2.48E−04 |
| hsa-miR-410 | 129 | 364 | −1.50 | 1.09E−03 |
| hsa-miR-1246 | 19,969 | 55,915 | −1.49 | 1.16E−03 |

TABLE 2

Circulating miRNAs associated with histopathological features of BC*

ER+ vs. ER−

| Gene name | ER+ (N = 21) Ave. counts | ER− (N = 21) Ave. counts | Log$^2$ fold diff. (ER+ vs. ER−) | P value | FDR |
|---|---|---|---|---|---|
| hsa-miR-375 | 3,189 | 18,356 | −2.23 | 6.28E−10 | 3.46E−07 |
| hsa-miR-429 | 58 | 221 | −1.94 | 7.48E−08 | 1.28E−05 |
| hsa-miR-196a | 184 | 694 | −1.92 | 8.14E−08 | 1.28E−05 |
| hsa-miR-141* | 21 | 75 | −1.82 | 5.99E−07 | 6.59E−05 |
| hsa-miR-376a | 200 | 65 | 1.63 | 4.72E−06 | 4.33E−04 |

TABLE 2-continued

Circulating miRNAs associated with histopathological features of BC*

| | | | | | |
|---|---|---|---|---|---|
| hsa-miR-370 | 585 | 198 | 1.56 | 9.98E−06 | 8.44E−04 |
| hsa-miR-141 | 442 | 1,216 | −1.46 | 3.34E−05 | 2.45E−03 |
| hsa-miR-200b | 150 | 400 | −1.42 | 5.82E−05 | 3.37E−03 |
| hsa-miR-125a-5p | 2,222 | 914 | −1.28 | 2.55E−04 | 1.17E−02 |
| hsa-miR-205 | 83 | 196 | −1.24 | 4.43E−04 | 1.87E−02 |
| hsa-miR-200a | 218 | 482 | −1.14 | 1.11E−03 | 4.08E−02 |
| hsa-miR-224 | 870 | 402 | 1.12 | 1.39E−03 | 4.79E−02 |

PR+ vs. PR−

| Gene name | PR+ (N = 14) Ave. counts | PR− (N = 28) Ave. counts | Log2 fold diff. (PR+ vs. PR−) | P value | FDR |
|---|---|---|---|---|---|
| hsa-miR-216a | 56 | 17 | 1.75 | 1.20E−06 | 1.56E−04 |
| hsa-miR-184 | 28 | 115 | −2.03 | 1.28E−06 | 1.56E−04 |
| hsa-miR-196a | 160 | 578 | −1.85 | 5.80E−06 | 5.28E−04 |
| hsa-miR-370 | 699 | 238 | 1.55 | 6.24E−06 | 5.28E−04 |
| hsa-miR-375 | 4,457 | 14,477 | −1.70 | 2.55E−05 | 1.76E−03 |
| hsa-miR-376a* | 225 | 86 | 1.40 | 5.27E−05 | 3.22E−03 |
| hsa-miR-133a | 84 | 32 | 1.36 | 8.72E−05 | 4.57E−03 |
| hsa-miR-654-5p | 154 | 64 | 1.25 | 2.88E−04 | 1.29E−02 |
| hsa-miR-125a-5p | 2,550 | 1077 | 1.24 | 2.93E−04 | 1.29E−02 |
| hsa-miR-224 | 1,028 | 440 | 1.22 | 3.72E−04 | 1.52E−02 |
| hsa-miR-217 | 120 | 52 | 1.22 | 4.97E−04 | 1.89E−02 |
| hsa-miR-429 | 67 | 176 | −1.38 | 5.72E−04 | 2.10E−02 |
| hsa-miR-494 | 255 | 114 | 1.16 | 7.86E−04 | 2.62E−02 |
| hsa-miR-99b | 10,464 | 4934 | 1.08 | 1.56E−03 | 4.40E−02 |

HER2+ vs. HER2−

| Gene name | HER2+ (N = 23) Ave. counts | HER2− (N = 19) Ave. counts | Log2 fold diff. (HER2+. vs. HER−) | P value | FDR |
|---|---|---|---|---|---|
| hsa-miR-885-3p | 32 | 160 | −2.31 | 2.05E−10 | 1.13E−07 |
| hsa-miR-122 | 98,310 | 464,256 | −2.24 | 3.08E−10 | 1.13E−07 |
| hsa-miR-375 | 17,052 | 3,977 | 2.10 | 1.72E−08 | 4.74E−06 |
| hsa-miR-184 | 128 | 35 | 1.88 | 5.72E−07 | 1.05E−04 |
| hsa-miR-1228* | 65 | 166 | −1.35 | 1.32E−04 | 7.62E−03 |
| hsa-miR-483-5p | 194 | 484 | −1.32 | 1.60E−04 | 8.80E−03 |
| hsa-miR-429 | 193 | 75 | 1.37 | 1.81E−04 | 9.48E−03 |
| hsa-miR-205 | 189 | 80 | 1.23 | 7.03E−04 | 3.14E−02 |
| hsa-miR-217 | 49 | 106 | −1.12 | 1.41E−03 | 5.00E−02 |

Inflammatory vs. Non-inflammatory

| Gene name | Inflam. (N = 10) Ave. counts | Non-inflam. (N = 32) Ave. counts | Log2 fold diff. (Inflam. vs. Non inflam.) | P value | FDR |
|---|---|---|---|---|---|
| hsa-miR-375 | 35,465 | 3,535 | 3.33 | 3.76E−20 | 4.14E−17 |
| hsa-miR-184 | 267 | 29 | 3.18 | 5.28E−18 | 2.90E−15 |
| hsa-miR-196a | 1217 | 195 | 2.64 | 3.62E−13 | 1.33E−10 |
| hsa-miR-429 | 341 | 77 | 2.15 | 4.14E−09 | 5.69E−07 |
| hsa-miR-200a | 811 | 206 | 1.98 | 6.26E−08 | 7.65E−06 |
| hsa-miR-200c | 3,714 | 1,033 | 1.85 | 4.22E−07 | 4.65E−05 |
| hsa-miR-3065-5p | 86 | 29 | 1.56 | 3.11E−05 | 3.45E−04 |
| hsa-miR-141 | 1,571 | 597 | 1.40 | 1.44E−04 | 7.19E−03 |
| hsa-miR-203 | 403 | 155 | 1.38 | 1.93E−04 | 8.85E−03 |
| hsa-miR-200b* | 89 | 36 | 1.33 | 3.90E−04 | 1.59E−02 |
| hsa-miR-1308 | 5,332 | 2,358 | 1.18 | 1.35E−03 | 4.96E−02 |

*FDR <0.05

PCR Validation of Selected miRNAs

Several miRNAs were selected, including miR-375, miR-122, miR-184, miR-196a, miR-1, miR-410, miR-432, and miR-16, for qRT-PCR-based validation using the same total RNA extracts used for deep sequencing (32 out of the 42 sequenced samples had sufficient amounts left for PCR assays). The sequencing-determined abundance of these miRNAs ranged from very high (e.g., miR-122, ranged from 4,683-1,094,999 counts with an average of 16,456) to very low (e.g., miR-184, ranged from 6-1,097 counts with an average of 61, and miR-410, ranged from 1-1,620 counts with an average of 220). For PCR analyses, levels of miR-16, which were consistent among all samples, and reportedly used as the internal control for circulating miRNAs in previous PCR-based studies (Heneghan H M, et al., Ann Surg 2010, 251:499-505; Roth C, et al., Breast Cancer Res 2010, 12:R90), were used as the reference for data normalization. Our results indicated that gene-specific PCR could detect miRNA with as few as 20 counts in a sample, and the low-abundant miR-184 and miR-410 could be detected from ~90% of all tested samples (29 out of 32). Pairwise Pearson correlation was calculated to determine the consistency of the miRNA levels determined by deep sequencing (normalized log 2 counts and PCR-determined levels relative to miR-16) in each sample. For all tested miRNAs, significant (P<0.05) correlations were observed between the two methods.

MiR-375 and miR-122, two miRNAs with the most significant fold differences in the associations with metastatic relapse and NCT response (Table 1), were identified for further study. Consistent with the deep sequencing results, lower levels of miR-375 and higher levels of miR-122 detected by PCR both significantly correlated with disease relapse in all patients and with resistance to NCT (non-pCR) in HER2$^+$ patients (FIG. 21). These data indicated the feasibility of cost-efficient PCR assays of these two genes to potentially predict clinical outcome of locally advanced BCs. Levels of other miRNAs examined by PCR did not show significant differences in the comparisons for disease relapse and NCT response.

Prediction of Relapse by Circulating miR-375 and miR-122

The sensitivity and specificity of the two circulating miRNA markers identified, i.e., miR-375 and miR-122, was analyzed in predicting metastatic relapse in our NCT study cohort using leave-one-out cross validation (See methods below for details). Results indicated that both circulating miR-375 and miR-122 could predict metastasis with relatively high sensitivity and specificity, and the miR-375/miR-122 two-gene signature demonstrated the best predicting performance, with a sensitivity of 80% and specificity of 100% (Table 3).

Figure 22:
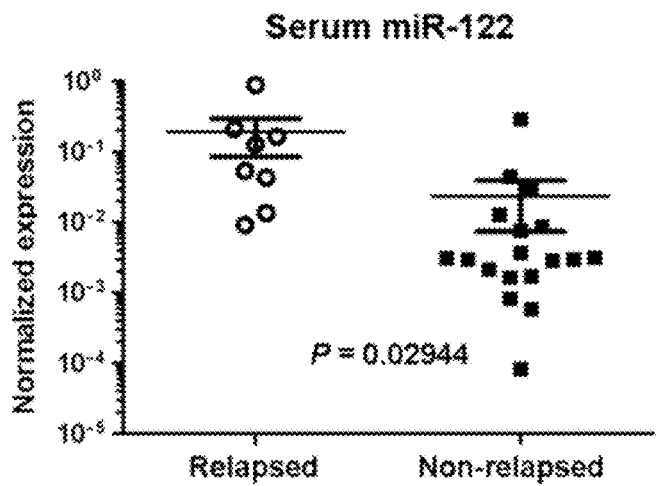
FIG. 22 is a graph showing circulating miR-122 predicts metastatic relapse in an independent BC cohort. Levels of serum miR-122 in an independent validation cohort of 26 stage II-III BC patients were measured by PCR and normalized to the level of miR-16 in each sample.

(FIG. 22 and Table 3). Levels of miR-375, however, were not significantly different between the relapsed and non-relapsed groups (Table 3), possibly due to the fact that patients in the validation cohort were generally lower stage at diagnosis, with more hormone receptor positive disease, and more frequently overexpressed HER2. In addition, they received diverse therapies seen in a general oncology practice. Because the status of ER/PR and HER2 in primary BCs have been historically linked to clinical outcomes (Rouzier R, et al., *Clin Cancer Res* 2005, 11:5678-5685; Caudle A S, et al., *J Clin Oncol* 2010, 28:1821-1828), the sensitivity and specificity of each histopathological parameter in association with development of metastatic relapse in the testing cohort was determined. Results indicated that, in comparison to the histopathological parameters, circulating miR-122 served as a better predictor of metastasis, regardless of the heterogeneity of this cohort (Odds Ratio 24.5; P<0.01).

Discussion

Using a comprehensive de novo sequencing approach, sets of circulating miRNAs were identified that were associated with various clinicopathological parameters and clinical outcome in stage II-III BC patients. Previous studies have linked higher circulating levels of miR-10b and miR-21 to negative ER status (Heneghan H M, et al., *Ann Surg* 2010, 251:499-505), and higher circulating levels of miR-155 to positive PR status (Zhu W, et al., *BMC Res Notes* 2009, 2:89). None of these miRNAs exhibited correlations

TABLE 3

Performance analysis among training and testing cohorts

| Predictor | | Predicted Relapse | Predicted Non-relapse | Sensitivity | Specificity |
|---|---|---|---|---|---|
| Training Cohort (N = 32) | | | | | |
| Circulating miR-375 | Observed relapse | 9 | 1 | 9/10 (90%) | 20/22 (91%) |
| | Observed non-relapse | 2 | 20 | | |
| Circulating miR-122 | Observed relapse | 4 | 6 | 4/10 (40%) | 11/22 (50%) |
| | Observed non-relapse | 11 | 11 | | |
| 375/122 two-gene signature | Observed relapse | 8 | 2 | 8/10 (80%) | 22/22 (100%) |
| | Observed non-relapse | 0 | 22 | | |
| Training Cohort (N = 26) | | | | | |
| Circulating miR-375 | Observed relapse | 0 | 8 | 0/8 (0%) | 11/18 (61%) |
| | Observed non-relapse | 7 | 11 | | |
| Circulating miR-122 | Observed relapse | 7 | 1 | 7/8 (88%) | 14/18 (78%) |
| | Observed non-relapse | 4 | 14 | | |
| 375/122 two-gene signature | Observed relapse | 2 | 6 | 2/8 (25%) | 17/18 (94%) |
| | Observed non-relapse | 1 | 17 | | |

Circulating miR-122 Predicts Metastasis in an Independent Cohort of Early-Stage BCs An independent validation cohort of 26 stage II-III BC patients, including 8 patients with metastatic recurrence within 2 years after initial diagnosis, as well as appropriate controls with matched clinical parameters but without disease recurrence was assembled. Serum RNA was isolated and subjected to qRT-PCR to detect levels of miR-375, miR-122 and miR-16. Upon normalization to miR-16, circulating miR-122 levels were significantly higher in the group with relapse (P=0.0294), and could predict metastasis at a sensitivity of 88% and specificity of 78% in this cohort with ER/PR status in our study, possibly due to the differences of the size, composition of study cohorts, and/or treatment regimens. Two miRNA clusters, miR-200b-200a-429 and miR-200c-141, were significantly associated with negative ER status and inflammatory BC (Tables 2). In addition, it was found that several miRNAs, including miR-375, miR-429, miR-196a, miR-370, miR-125a-5p, and miR-224, simultaneously correlated with both ER and PR status in the same direction (Table 2). Among these miRNAs, miR-375 and miR-429 also correlated with HER2 status but in the opposite direction as compared to their correlations with ER/PR status (Table 2). Expression of these miRNAs in primary BCs and their functional links with ER/PR/HER2 merit additional investigation, and may further elucidate the pathogenic mechanisms of these long-known receptors in BC.

Figures 21A, 21B:
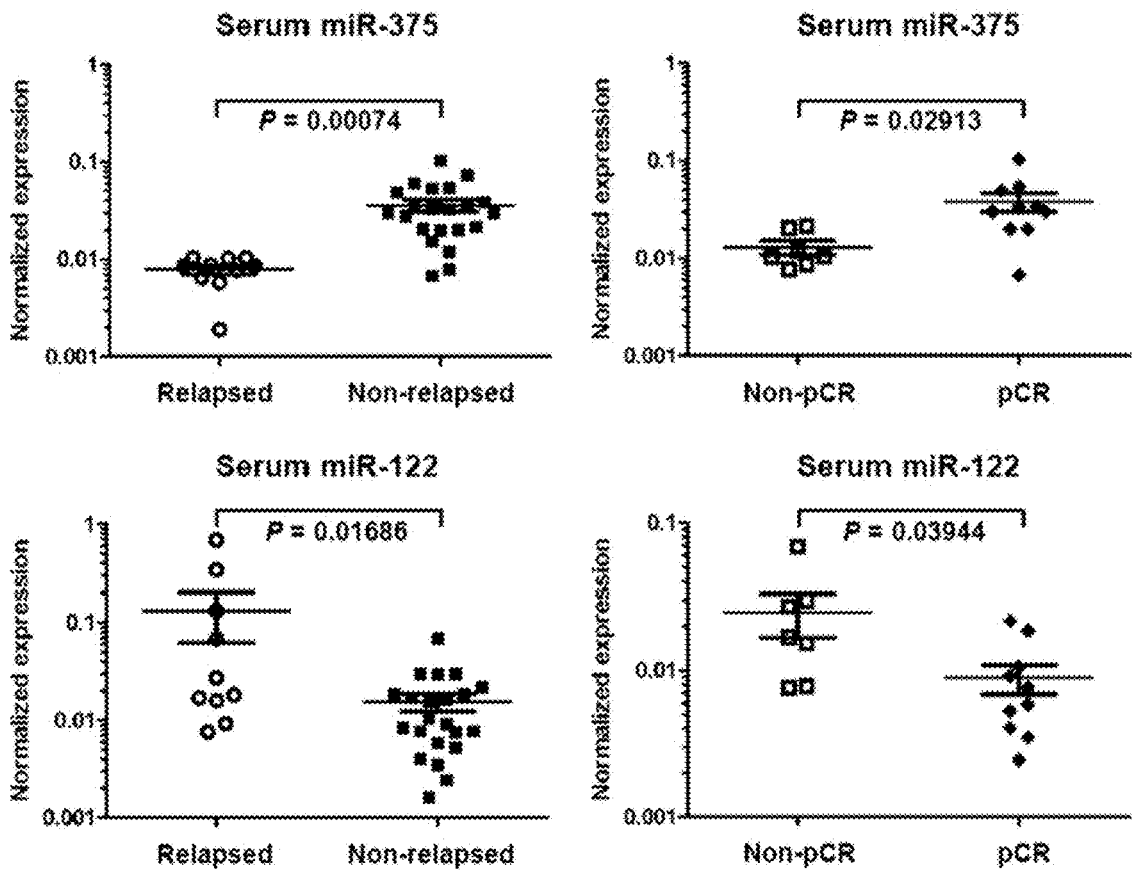
FIGS. 21A and 21B show PCR-determined levels of miR-375 and miR-122 are associated with clinical outcome. Levels of miR-375 and miR-122 were measured by PCR and normalized to the level of miR-16 in each sample. Comparisons were carried out between the two groups of relapsed vs. non-relapsed (FIG. 21A) or pCR vs. non-pCR (FIG. 21B). For each group, mean and the standard error of the mean (SEM) are indicated. T-tests were performed between the two groups and P values are indicated.

A two-gene signature was identified consisting of miR-375 and miR-122 with the capacity to predict disease relapse in our study cohort of stage II-III BC patients who received identical NCT regimens. In a heterogeneous validation set derived from an observational cohort, circulating miR-122, but not miR-375, remained as a predictor of metastasis (FIG. 22). Interestingly, both miR-375 and miR-122 correlated with HER2 status (Table 2), with higher levels of miR-375 and lower levels of miR-122 associating with positive HER2 status (Table 2), pCR to NCT (FIG. 21B), and absence of relapse (FIG. 21A).

MiR-122, the circulating miRNA that consistently predicted metastasis in both the present study cohort and validation cohort, is the most frequent miRNA isolated in the liver and is involved in the regulation of lipid metabolism (Girard M, et al., *J Hepatol* 2008, 48:648-656). Downregulation of miR-122 has been reported in hepatocarcinoma (HCC) (Kutay H, et al., *J Cell Biochem* 2006, 99:671-678). In contrast, higher levels of miR-122 in circulation correlate with HCC (Xu J, et al., *Mol Carcinog* 2011, 50:136-142) and liver injury (Zhang Y, et al., *Clin Chem* 2010, 56:1830-1838). Expression of miR-122 has also been reported in primary fibroblasts, where the miRNA is involved in p53 mRNA polyadenylation/translation by targeting the cytoplasmic polyadenylation element binding protein (CPEB) (Burns D M, et al., *Nature* 2011, 473:105-108). Expression and function of miR-122 have not yet been reported in BC. Our results here, however, show a role of miR-122 in BC progression.

Roth et al. report that circulating levels of miR-10b, miR-34a and miR-155 correlate with the presence of overt metastases in BC patients (Roth C, et al., *Breast Cancer Res* 2010, 12:R90). These miRNAs, however, did not significantly correlate with metastatic relapse in our retrospective study in stage II-III patients. It is possible that the change of circulating miR-10b, miR-34a and miR-155 levels occurs after cancer dissemination, whereas levels of circulating miR-122 and miR-375, as identified herein, start to change and reflect metastatic potential at an earlier stage of disease.

Conclusions

Using a comprehensive de novo sequencing approach, sets of circulating miRNAs were identified that were associated with various clinicopathological parameters and clinical outcome in stage II-III BC patients. A two-gene signature set consisting of miR-375 and miR-122 was identified with the capacity to predict disease relapse in our study cohort of stage II-III BC patients who received identical NCT regimens. In a heterogeneous validation set derived from an observational cohort, circulating miR-122, but not miR-375, remained as a predictor of metastasis. These results allow for optimized chemotherapy treatments and preventive anti-metastasis interventions in future clinical applications.

Example 3. Breast Cancer-Secreted miR-122 Regulates Glucose Allocation in Niche Cells to Promote Cancer Progression and Metastasis Reprogrammed energy metabolism to fuel rapid cell growth and proliferation is an emerging hallmark of cancer. Unlike normal cells, most cancer cells use aerobic glycolysis with reduced mitochondrial oxidative phosphorylation for glucose metabolism even when oxygen is sufficient. This phenomenon, known as the "Warburg effect", is believed to favour the uptake and incorporation of nutrients needed to produce a new cell. To compensate for the compromised ATP production caused by this metabolic switch, cancer cells often adopt mechanisms to increase glucose uptake and utilization. One mechanism involves the regulation of glucose transporters, among which GLUT1 is responsible for basal levels of glucose uptake in all cells (Zhao, F. Q. and Keating, A. F. Curr Genomics 8, 113-128 (2007)). GLUT1 can be regulated by numerous pathways such as the PI3K/Akt/mTOR pathway which is frequently activated in cancer. In addition, hypoxia can stimulate glucose uptake and metabolism through the hypoxia-inducible factor 1 (HIF-1) transcription factor complex to induce GLUT3 and several glycolytic genes including aldolase A (ALDA), phosphoglycerate kinase 1 (PGK1) and PKM (O'Rourke, J. F., et al., Eur J Biochem 241, 403-410 (1996); Semenza, G. L., et al., J Biol Chem 269, 23757-23763 (1994)). Moreover, it was recently reported that phosphorylation or sumoylation of PKM2 leads to translocation to the nucleus, where it acts as a co-activator of β-catenin, STAT3, Oct-4, and HIF-1α to induce multiple target genes including GLUT1, PDK1 and HK1 (Spoden, G. A. et al. J Cell Biochem 107, 293-302 (2009); Yang, W. et al. Nat Cell Biol 14, 1295-1304 (2012); Gao, X., et al., Mol Cell 45, 598-609 (2012); Yang, W. et al. Nature 480, 118-122 (2011); Lee, J., et al., Int J Biochem Cell Biol 40, 1043-1054 (2008); and Luo, W. et al., Cell 145, 732-744 (2011)). Herein is described a mechanism mediated by a cancer-secreted extracellular microRNA (miRNA) that reallocates glucose to favour uptake by cancer cells.

MiRNAs negatively regulate gene expression by binding to the 3' untranslated region (3'UTR) of a target mRNA, leading to degradation or translation blockade (Bartel, D. P. Cell 136, 215-233 (2009)). MiRNAs are involved in a variety of biological pathways. Therefore, deregulation of miRNAs is tightly linked to cancer. Circulating miRNAs that reflect the presence and pathologic features of cancer have emerged as potential biomarkers for cancer diagnosis and prognosis (Mitchell, P. S. et al. PNAS; 105, 10513-10518 (2008); Taylor, D. D. and Gercel-Taylor, C., Gynecol Oncol 110, 13-21 (2008); Wu, X. et al. J Transl Med 10, 42 (2012); Zhu, W., et al., BMC Res Notes 2, 89 (2009)). MiRNAs can be secreted into the extracellular environment through microvesicles (such as exosomes) or in complexes with protein or lipid-based carriers (Zen, K. and Zhang, C. Y. Med Res Rev 32, 326-348 (2012); Redis, et al., Pharmacol Ther 136, 169-174 (2012)). Accumulating evidence demonstrates that miRNAs as well as proteins can be transferred to neighbouring or distant cells in these secretory forms to modulate cell function (Valadi, H. et al. Nat Cell Biol 9, 654-659 (2007); Wang, K., et al., Nucleic Acids Res 38, 7248-7259 (2010); Arroyo, J. D. et al. PNAS, 108, 5003-5008 (2011); Vickers, K. C. and Remaley, A. T., Curr Opin Lipidol 23, 91-97 (2012); Skog, J. et al. Nat Cell Biol 10, 1470-1476 (2008); Peinado, H. et al. Nat Med 18, 883-891 (2012)). Extracellular miRNAs are emerging as group of messengers and effectors in intercellular communication.

Several miRNAs have been implicated in metabolism and metabolic disorders. Among them, miR-122 regulates cholesterol efflux, liver triglyceride content, and the rate of β-oxidation by targeting multiple genes (Moore, K. J., et al., Annu Rev Nutr 31, 49-63 (2011)). Potential miR-122 targets have been analyzed by luciferase reporter-based 3'UTR screening, identifying the glycolytic gene PKM as one of the targets (Boutz, D. R. et al. J Biol Chem 286, 18066-18078

(2011)), which suggests that miR-122 may play a role in glucose metabolism. As described herein, in breast cancer (BC) patients, circulating miR-122 was identified as a marker for predicting clinical outcomes, including metastatic progression in early-stage BC. The function of extracellular miR-122 in cancer progression and metastasis was then investigated. In this example, it is demonstrated that cancer cells secrete high levels of miR-122 which can be transferred to normal cells in the pre-metastatic niches, thereby suppressing glucose utilization in these cells to accommodate the massive energy needs of cancer cells during metastatic growth.

Results

MiR-122 is Highly Secreted in Cancer Derived Exosomes

Figures 23A, 23B:
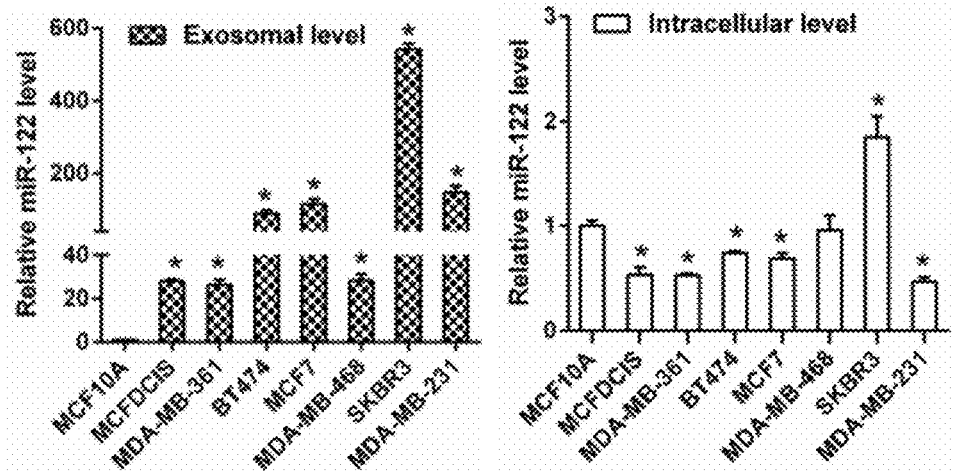
FIGS. 23A, and 23B show miR-122 is highly secreted in cancer derived exosomes. Exosomal (FIG. 23A) and cellular (FIG. 23B) RNA were extracted from various cell lines and subjected to miR-122 RT-qPCR. Data was normalized to levels of miR-16 (exosomal.

In the example above, higher levels of circulating miR-122 were associated with metastatic progression in early-stage BC patients, suggesting a pro-malignant role of extracellular miR-122. Therefore, it was determined whether BC cells could secrete miR-122, and thus contribute to the presence of this miRNA in the circulation. Exosomes were isolated from a panel of BC cell lines as well as the non-cancerous MCF10A mammary epithelial cells. It was found that all BC-derived exosomes carried significantly elevated miR-122 compared to MCF10A-derived exosomes (FIG. 23A). The increased cancer cell secretion of miR-122 was not accompanied by increased intracellular level, as most cancer lines exhibited reduced intracellular miR-122 compared to MCF10A (FIG. 23B). These results indicate that high secretion of exosomal miR-122 is cancer-specific and that excretion of miR-122 may provide a more favourable outcome for the cancer cell. This further suggests that the potential effect of cancer-derived miR-122 may be ectopically observed in the recipient cells upon exosome-mediated transfer rather than in the cancer cells producing it.

MiR-122 Suppresses Glucose Metabolism by Down-Regulating PKM2

Figure 24A:
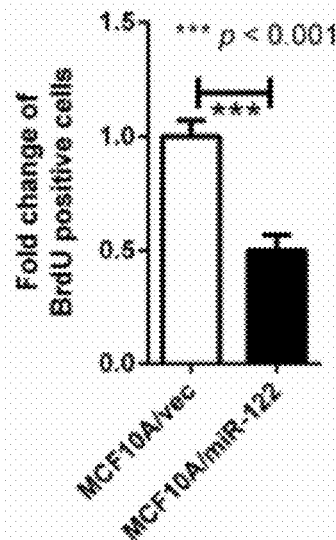

To study of function of miR-122, MCF10A cells were engineered to stably over-express miR-122 (MCF10A/miR-122; FIG. 30A) or the control pBABE vector (MCF10A/vec). It was observed that MCF10A/miR-122 cells had reduced proliferation which was confirmed by BrdU incorporation analyzed by flow cytometry (FIG. 24A). This led to testing if the reduced proliferation was a consequence of nutrient uptake. Metabolome analysis of the cells by nuclear magnetic resonance (NMR) spectroscopy revealed significantly decreased intracellular glucose and pyruvate in MCF10A/miR-122 cells (FIG. 24B), consistent with the reduced activity of PKM and decreased GLUT1 expression. Increased UDP-glucose (FIG. 24B) and glycogen staining (FIG. 30B) were also observed in the MCF10A/miR-122 cells, likely due to the excessive glucose in these cells. In contrast, levels of the amino acids in the cells were not significantly altered by miR-122 (FIG. 24B). Next changes of metabolites were analyzed in the culture media of MCF10A cells with or without miR-122 over-expression after 72 hours. Cells overexpressing miR-122 displayed ~50% decreased glucose uptake from the media and ~40% reduced lactate production (FIG. 24C). Modestly diminished glutamine metabolism was also observed in these cells, possibly reflecting cell adaptation for the altered overall metabolic rate.

The changes in intracellular glucose and glycogen staining suggested miR-122 may have a target involved in glycolysis. Sequence analysis predicted a single, species-conserved miR-122 binding site in the 3'UTRs of human PKM and citrate synthase (CS) genes (FIG. 24D). Therefore, the full length 3'UTR of these two genes was cloned as well as their seed-sequence-mutated version into a luciferase plasmid and assessed for the ability of miR-122 to down-regulate luciferase expression. For both genes, the wild-type but not mutated site responded to exogenously expressed miR-122 by directing ~50% reduction of reporter gene expression (FIG. 24E), thus confirming that miR-122 targets PKM and CS through these sites in the 3'UTRs.

Figure 24E:
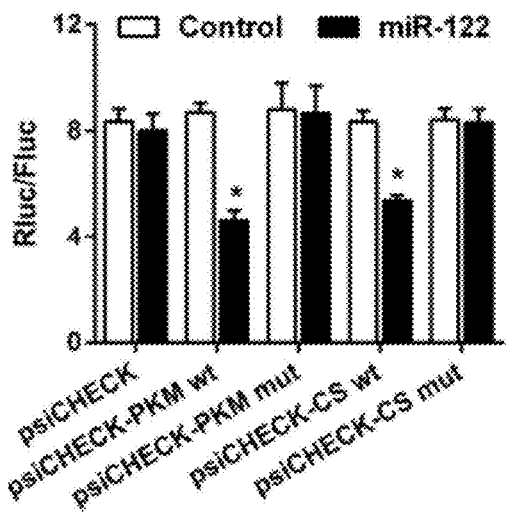
Figure 24F:
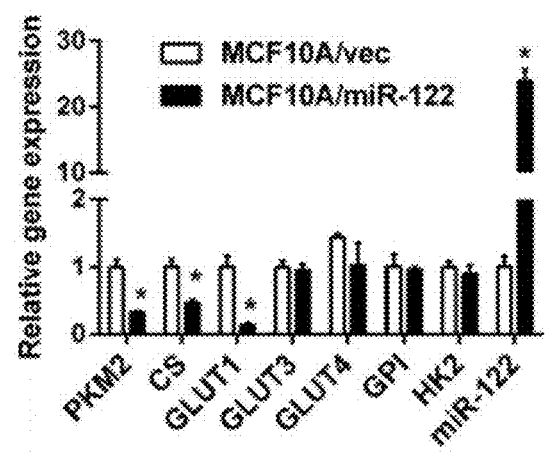
Figure 24G:
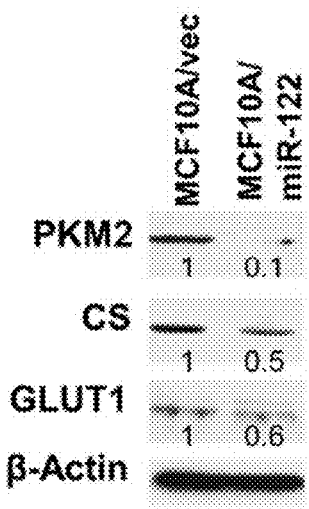
Figure 24H:
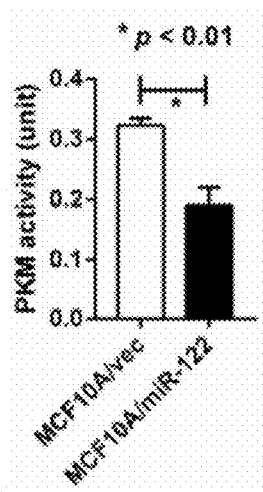
Figure 24I:
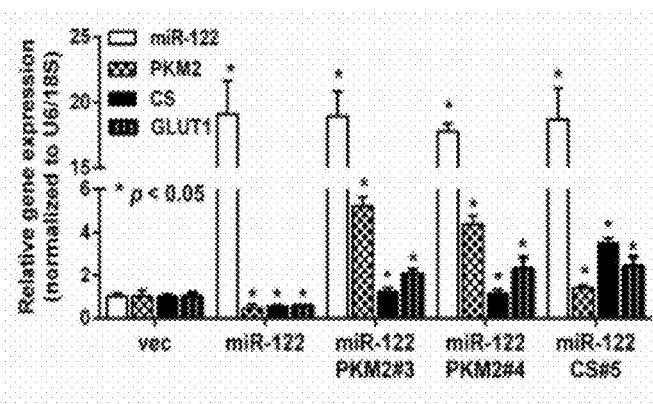
Figure 24J:
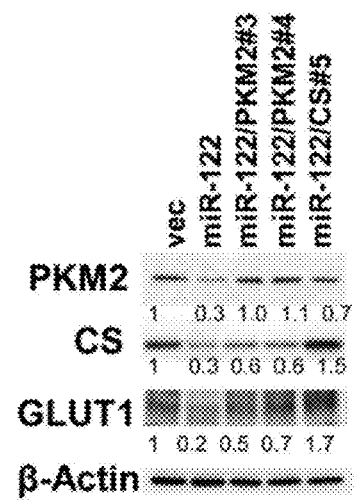
Figure 24K:
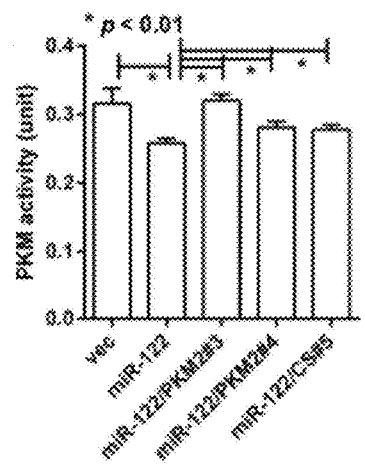
Figure 24L:
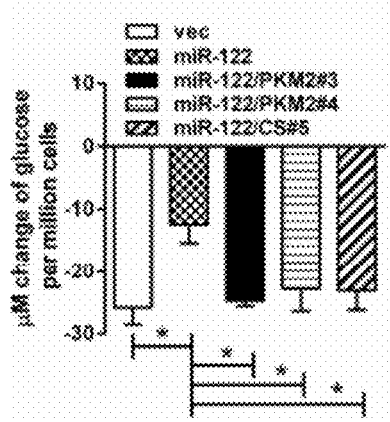

The critical role of PKM2 and CS in glycolysis and TCA cycle urged us to explore the function of miR-122 in regulating glucose metabolism. MCF10A/miR-122 cells exhibited significantly reduced PKM2 (FIG. 31A), CS, and GLUT1 at both RNA and protein levels (FIGS. 24F and 24G), whereas no significant difference was observed with GLUT3, GLUT4, hexokinase 2 (HK2), or glucose phosphate isomerase (GPI; FIG. 24F). Consistent with PKM2 down-regulation, miR-122 also caused a significant reduction of PKM enzymatic activity (FIG. 24H).

To further determine if the miR-122-induced decrease in glucose consumption was mediated by PKM2 and/or CS down-regulation, the expression of these genes was restored in MCF10A/miR-122 cells by over-expressing the PKM2 or CS cDNA that lacked the 3'UTR. Both colonies (PKM2#3 and PKM2#4) with fully or partially restored PKM activity showed restored GLUT1 expression and glucose uptake from the media that were comparable to MCF10A/vec cells (FIGS. 24I, 24J, 24K and 24L). It was observed that restoration of CS by exogenous expression was always accompanied by elevated expression of endogenous PKM2, possibly reflecting a natural feedback mechanism to accommodate the increased need for pyruvate by enhanced CS activity. The results indicate that restoration of PKM2 alone is sufficient to abolish the effect of miR-122 on glucose uptake.

Exosomal miR-122 Down-Regulates Glucose Consumption in Niche Cells

To study the ectopic effect of cancer-secreted miR-122, lung fibroblasts, brain astrocytes, and neurons that are abundantly present in the pre-metastatic sites (lung and brain) of BC were studied. Primary mouse lung fibroblasts and astrocytes exhibited efficient uptake of exosomes regardless of the producer cells (MCF10A or MDA-MB-231) as indicated by the internalization of DiI fluorescence upon incubating the recipient cells with DiI-labelled exosomes.

Figures 25D, 25E:
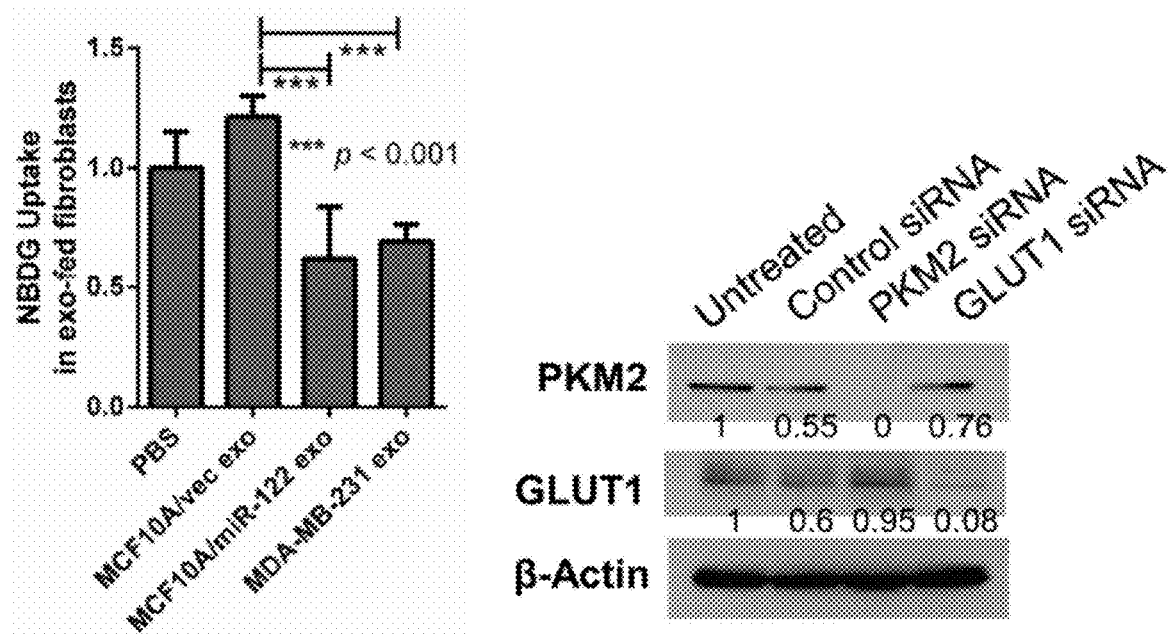

First, the effect of exosomal miR-122 on fibroblasts was examined. Cells were treated with exosomes derived from MCF10A, MCF10A/miR-122, or MDA-MB-231. Exosomes carrying high miR-122 levels (from the latter two lines; FIG. 23A, FIG. 30) caused significantly increased miR-122 (FIG. 25A) and decreased expression of PKM2, CS, and GLUT1 in recipient fibroblasts (FIGS. 25A and 25B; PKM isoform determined in FIG. 31A), along with decreased PKM activity (FIG. 25C). Using a fluorescent analogue of glucose, 2-[N-(7-nitrobenz-2-oxa-1,3-diazol-4-yl)amino]-2-deoxy-D-glucose (2-NBDG), which has been used to assess glucose transport in various cell types (Lloyd et al., Physiol. Res. 48:401-410 (1999); Loaiza, et al., J. Neurosci. 23:7337-7342 (2003); Yamada et al., J. Biol. Chem. 275:22278-22283 (2000); and Itoh et al., J. Cereb. Blood Flow Metab., 24:993-1003 (2004), the glucose uptake was quantified in exosome-treated fibroblasts. Consistent with the suppressive effect of miR-122 on glucose metabolism, high-miR-122 exosomes significantly reduced 2-NBDG uptake in recipient cells (FIG. 25D), demonstrating that suppression of PKM2 by miR-122 caused reduced glucose uptake.

Figures 25F, 25G:
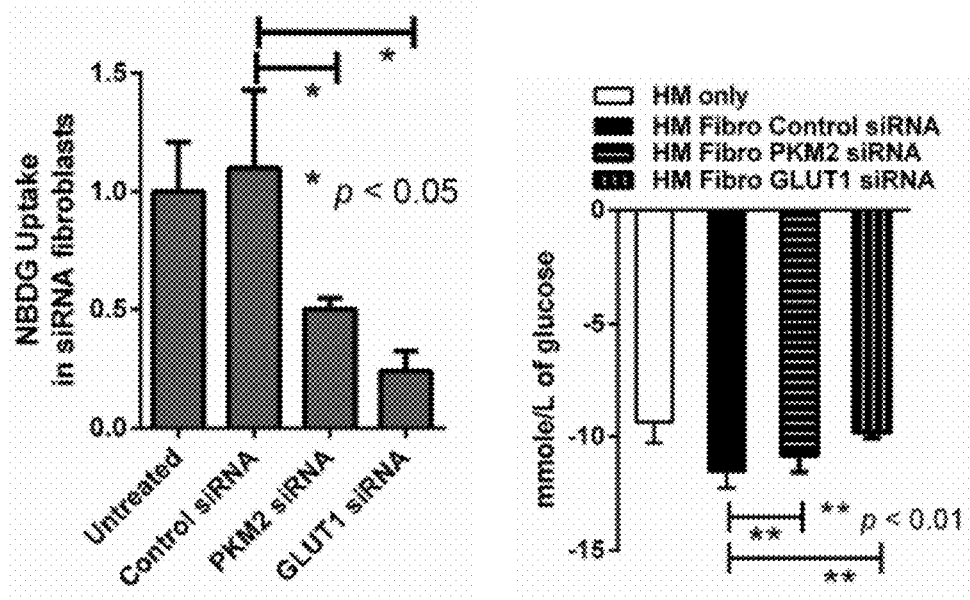

To further validate that the reduction of PKM2 and GLUT1 was responsible for the observed reduction of glucose uptake, siRNA against either PKM2 or GLUT1 was utilized. The efficiency of target knock-down by determined by Western blot analysis (FIG. 25E). Indeed knock-down of either PKM2 or GLUT1 reduced 2-NBDG uptake, with GLUT1 having a more pronounced effect (FIG. 25F), confirming that miR-122 reduces glucose uptake through PKM2 downregulation and concomitant decrease in GLUT1 expression. To confirm that fibroblasts could compete with cancer cells for glucose, a co-culture system was set up using fibroblasts treated with PKM2 or GLUT1 siRNA. Media metabolite analysis showed PKM2 and GLUT1 knockdown resulted in reduced glucose uptake compared to control siRNA and restored glucose consumption similar to MDA-MB-231-HM cells cultured alone (FIG. 25G).

Glucose is the primary energy substrate in the mammalian brain with neurons and astrocytes being the major consumer among other cell types. Therefore, the effect of exosomal miR-122 on glucose consumption was examined in primary mouse astrocytes. Similar to lung fibroblasts, astrocytes treated with exosomes carrying high miR-122 levels had significantly increased miR-122 in recipient cells (FIG. 32A). Consequently, as a result of miR-122 over-expression, a significant decrease of both PKM2 and GLUT1 was observed at the protein level (FIG. 32B; PKM isoform determined in FIG. 31A). The reduction of PKM2 protein also caused a significant reduction of PKM activity (FIG. 32C). In addition, astrocytes that received exosomes carrying high miR-122 exhibited significantly reduced 2-NBDG uptake (FIG. 33D), confirming that exosomal miR-122 also reduces glucose consumption in these cells.

Exosomal miR-122 Reprograms Niche Tissues to Alter their Glucose Consumption

Figure 26D:
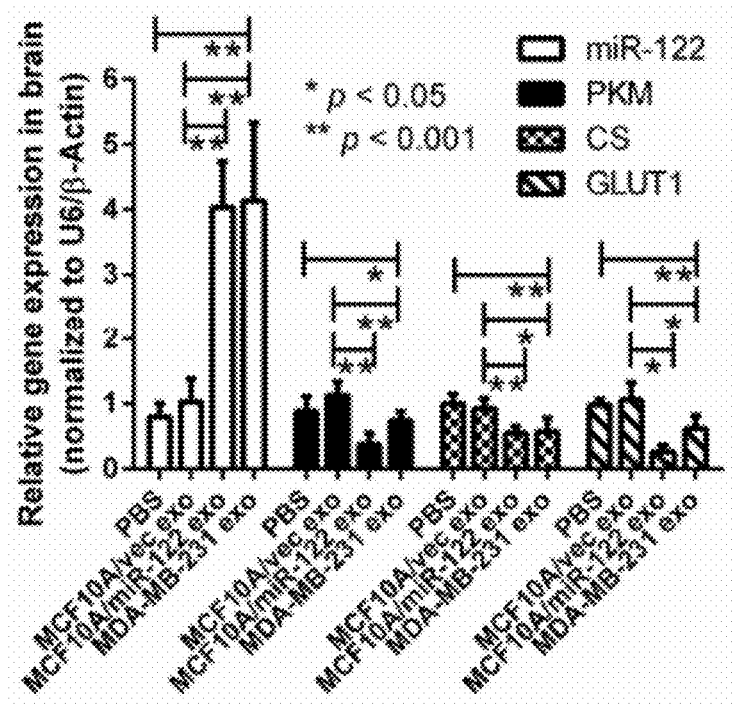
Figure 26E:
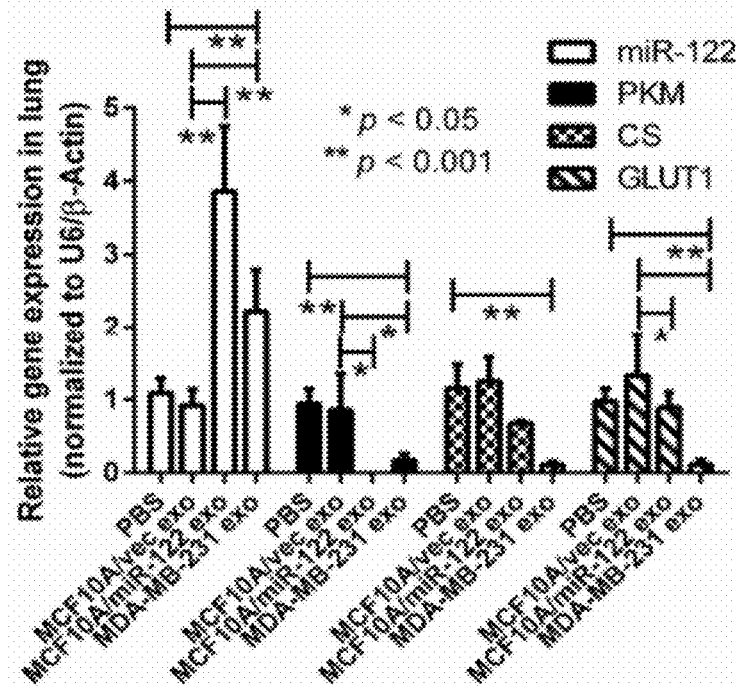

To verify that cancer-secreted exosomal miR-122 results in glucose metabolism modification in vivo, exosomes were isolated from high miR-122-secreting cell lines (MCF10A/miR-122 and MDA-MB-231) and intravenously injected them biweekly for 3.5 weeks in NOD/SCID/IL2Rγ-null (NSG) mice to mimic the secretion of exosomes from a primary tumour and compared them to mice that received exosomes derived from low miR-122-secreting cell line MCF10A/vec and vehicle (PBS). Mice were then injected with 2-NBDG to test glucose uptake in niche tissues. It has been shown that 2-NBDG is able to penetrate the blood-brain barrier in vivo (Itoh et al., J. Cereb. Blood Flow Metab., 24:993-1003 (2004)) and follows a similar metabolic pathway as glucose by entering the cell via glucose transporters and being phosphorylated at the C-6 position by hexokinases (Yamada, et al., J. Biol. Chem., 275:22278-83 (2000)). The brain and lung, two major organs, were examined for BC metastasis. Using coimmunofluorescence, tissues were stained for a cell type specific marker (MAP2 for neurons, GFAP for astrocytes, and fibroblast specific protein-1 (FSP-1) for fibroblasts) and a human specific exosomal marker CD63, demonstrating that exosomes derived from human cell lines can be received by these niche cell types in vivo (FIG. 26A). Both brain and lung showed reduced 2-NBDG uptake as a consequence of receiving miR-122 from circulating exosomes (FIGS. 26B and 26C). Functional analysis of both tissues verified high miR-122 expression as a result of exosomal transfer by RT-qPCR and the causal down-regulation of PKM, CS, and GLUT1 expression (FIGS. 26D and 26E).

To address if the metabolic reprogramming by miR-122 could directly benefit cancer metastasis, mice were pre-treated with high miR-122 exosomes, which was followed by a cancer cell chase using luciferase-labelled MDA-MB-231-HM cells injected intracardiac to systemically distribute the cancer cells. The lung and brain were then analyzed for metastases using luciferase DNA qPCR. The lungs of mice that received high miR-122 exosomes had significant metastatic colonization in all mice (N=5, FIG. 27F). It was also observed that at least 2 cases of metastases in the brains of mice that received high miR-122 (FIG. 27G). No metastases were observed in the lungs and brains of mice treated with low miR-122 (MCF10A/vec and PBS, FIGS. 27F and 27G). This data indicates that cancer-secreted exosomal miR-122 results in reprogramming of niche tissue glucose utilization as a possible mechanism to promote circulating tumour cell colonization by reducing the competition for native glucose.

Figure 27B:
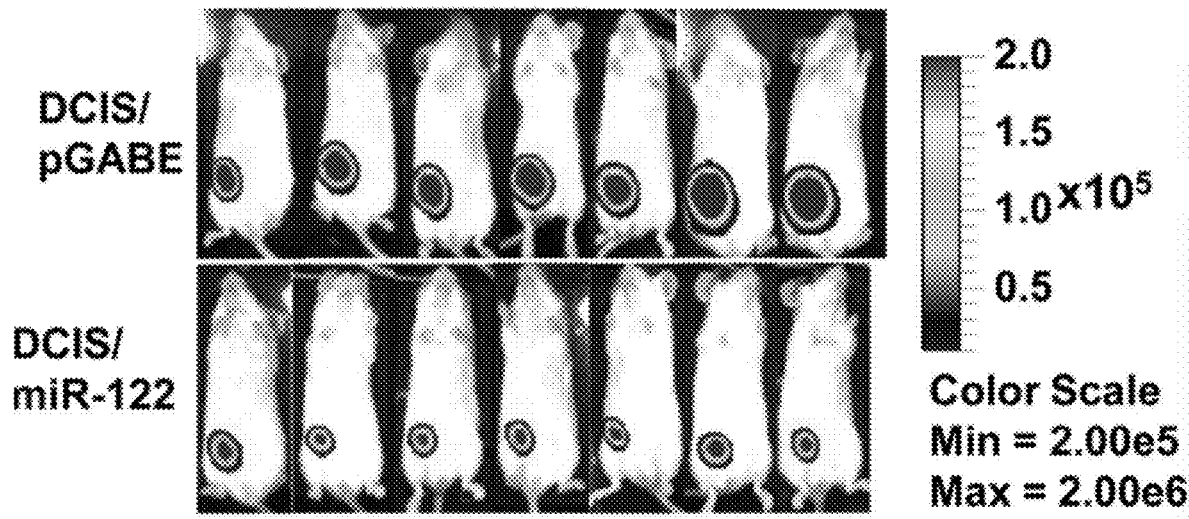
Figure 27C:
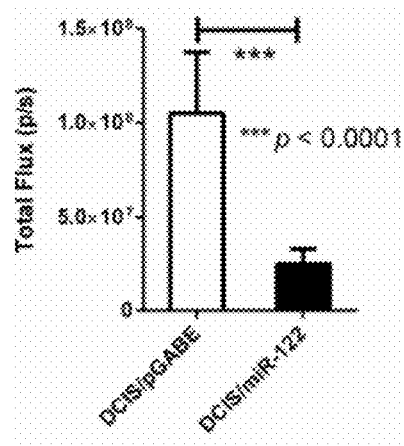

MiR-122 Over-Expression Reduced Primary Tumor Proliferation while Enhancing Metastases To address the effect of miR-122 over-expression on tumour formation, a metastatic orthotopic xenograft model was generated that stably over-expresses miR-122 using MCFDCIS cells (DCIS/miR-122) and the pGABE control vector (DCIS/pGABE) by injecting cells into the mammary fat pad of NSG mice. Similar to MCF10A cells, miR-122 over expression reduced cell proliferation analysed by cell counting and had reduced glucose uptake from the conditioned media (FIGS. 33A and 33B). PKM and CS were validated as miR-122 targets by psiCheck luciferase assay, RT-qPCR, and Western blot analysis (FIGS. 33C, 33D, and 33E). Using DCIS/miR-122 cells, orthotopic xenograft tumours were established in the mammary fat pad of NSG mice. DCIS/miR-122 tumours were significantly smaller than DCIS/pGABE tumours by caliper measurement (FIG. 27A) and by quantification of bioluminescent imaging (BLI) at Week 3 post tumour cell implantation (FIGS. 27B and 27C). To determine if the reduction of tumour burden by miR-122 over-expression was a result of decreased proliferation or increased apoptosis, tumour sections were stained with Ki67 and cleaved caspase 3. Ki67 staining revealed a significant decrease in positive cells (FIGS. 27D and 27E) while no changes were observed for cleaved caspase 3.

Figure 27I:
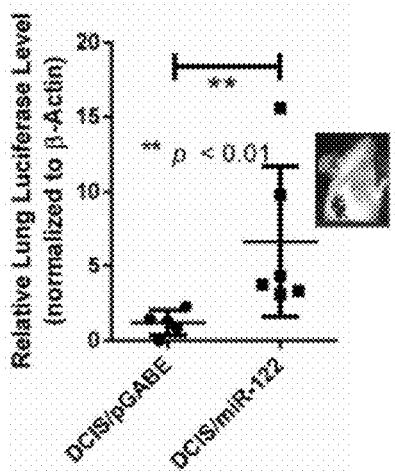

Metastatic niche tissues were analysed for miR-122 expression by RT-qPCR, demonstrating that mice bearing DCIS/miR-122 tumours had increased miR-122 expression in the brain and lung (FIG. 27F). It was also observed that PKM and GLUT1 were decreased in the tumour, brain, and lung as a result of miR-122 over-expression (FIG. 27D). 2-NBDG uptake was significantly reduced in high miR-122 tumours and brains, although not in lungs possibly due to the lower basal expression level of GLUT1 as the lungs are not dependent on glucose (FIG. 27G). Metastatic colonization in the lung, brain, and liver was analyzed by luciferase DNA qPCR, with the brain and lung both having two positive cases of metastases (FIGS. 27H and 27I). No metastases were observed in the liver. These data suggest that miR-122 reduces primary tumour proliferation by restricting glucose uptake while simultaneously reprogramming the premetastatic niche to promote tumour cell colonization and metastatic formation.

Figure 28A:
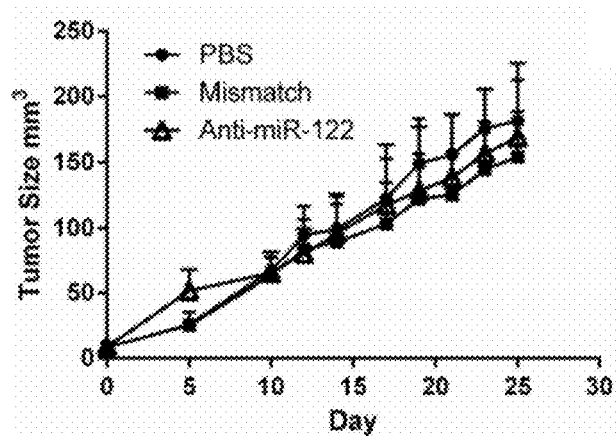
Figure 28B:
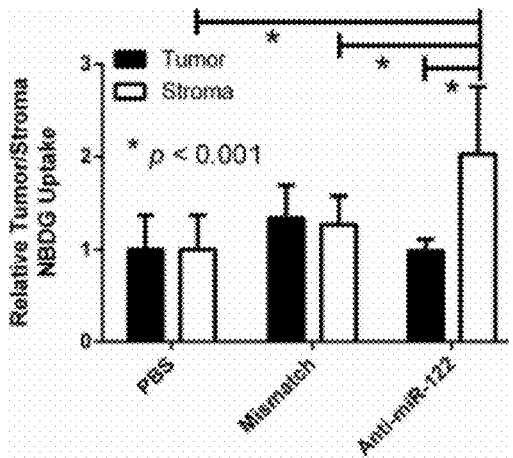
Figure 28C:
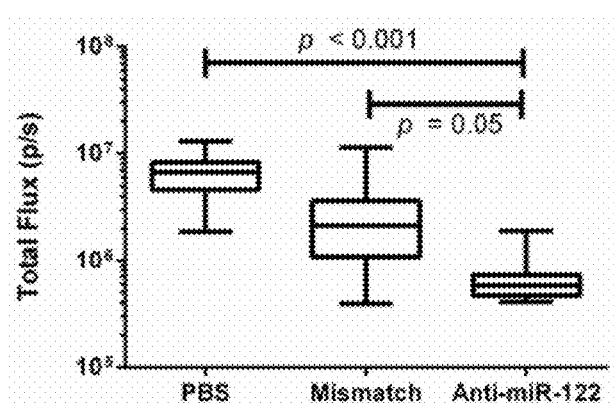
Figure 28D:
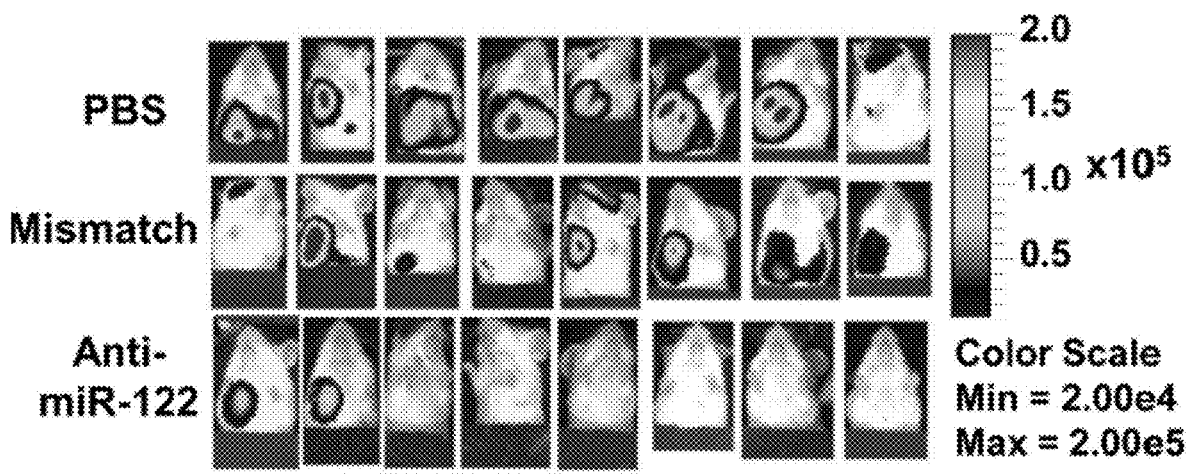

MiR-122 Intervention Alleviates Cancer-Induced Glucose Reallocation In Vivo and Reduces Metastasis The association of circulating miR-122 with BC metastasis and the in vitro data suggest miR-122 may be a therapeutic target for BC. To study the in vivo effect of miR-122 intervention, a metastatic orthotopic xenograft model of BC was established by injecting luciferase-labelled MDA-MB-231-HM cells. Mice were separated into three treatment groups that received PBS (vehicle control), mismatch control oligos, or anti-miR-122 oligos starting 3 days after cancer cell transplantation. Tumor volume measurements and BLI showed no significant difference in the size of the primary tumor among the three groups (FIG. 28A and FIGS. 34A and 34B). 2-NBDG uptake in the tumor and tumor-adjacent stroma is shown in FIG. 28B. BLI at week 5 started to reveal a lower incidence of metastasis in mice receiving antimiR-122 treatment, particularly to the lung and brain (FIGS. 28C and 28D). Metastases were confirmed by H&E staining. Effectiveness of anti-miR-122 treatment was confirmed by in situ hybridization (ISH) for miR-122, which indicated significantly reduced miR-122 in antimiR-122-treated tumours compared to the other two groups (FIG. 34C). Immunohistochemistry (IHC) of tumour sections showed enhanced staining of PKM2 in the tumor-adjacent stromal cells of anti-miR-122-treated mice, whereas no significant change was observed in the tumour cells (FIG. 34C). Additionally, enhanced staining of CS was observed in tumour cells with enhanced staining of GLUT1 observed in both the tumor and tumor-adjacent stromal cells of anti-miR-122-treated mice (FIG. 34C).

Figure 28I:
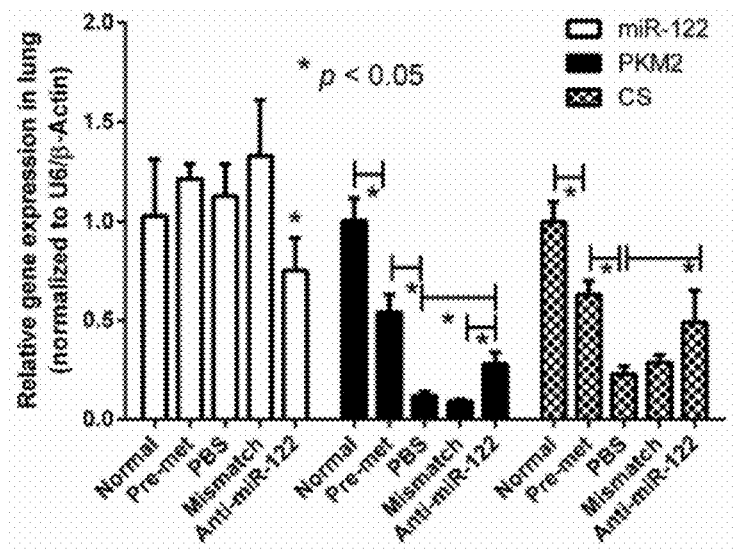
Figure 28J:
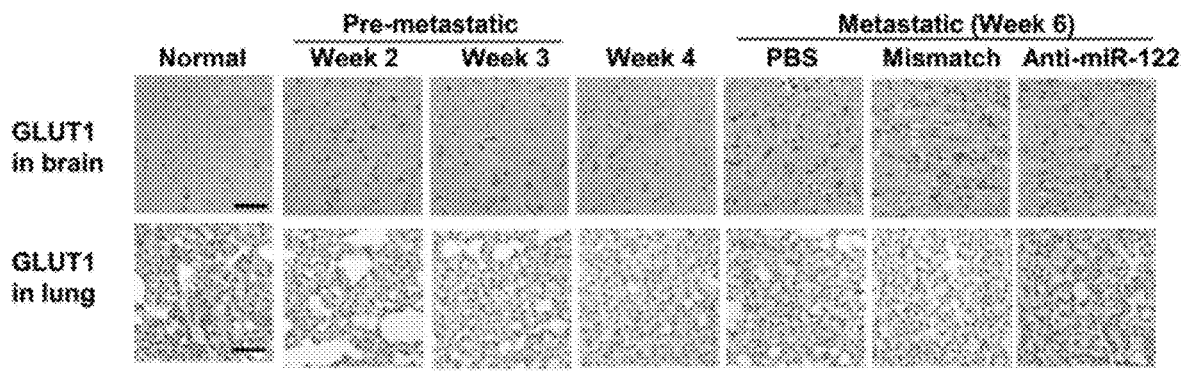

To determine the intercellular effect of the primary tumour on distant tissue glucose utilization, 2-NBDG was injected prior to sacrifice and examined brain and lung of MDA-MB-231-HM tumour-bearing mice that were sacrificed at week 3 in the absence of detectable distant metastases. At this pre-metastatic (pre-met) stage, both brain and lung tissues showed reduced 2-NBDG uptake compared to non-tumour bearing normal mice (FIGS. 28E, 28F and 28G), suggesting that factors secreted by the primary tumour can regulate glucose utilization in a distant organ to condition the niche in preparation for metastasis. This effect became more pronounced as cancer progressed, since a further reduction in 2-NBDG uptake was observed in the metastasis-free areas of brain and lung at week 6 when metastases had developed in these organs (FIGS. 28E, 28F and 28G; PBS and mismatch oligos groups). Notably, treatment with anti-miR-122, but not the mismatch control oligos, significantly alleviated tumour-derived suppression of glucose uptake in the brain although the restoration was not significant in the lung (FIGS. 28E, 28F and 28G). Additionally, the levels of miR-122, PKM, CS, and GLUT1 were examined. In the brain, miR-122 levels increased with tumour progression with a significant reduction in mice receiving anti-miR-122 oligos. Supporting our in vitro data, it was observed that an inverse correlation between miR-122 and the levels of PKM1 (isoform determined in FIG. 31B) and GLUT1 during tumour progression. The suppression of PKM1 and GLUT1 was relieved by anti-miR-122 treatment (FIGS. 28H and 28J). In the lung, anti-miR-122 oligos reduced miR-122 with alleviation of cancer-induced suppression of PKM2 (isoform determined in FIG. 31B) and CS, which was alleviated by antimiR-122 treatment (FIGS. 28I and 28J). Taken together, the in vitro and in vivo data indicates that cancer cells can induce glucose reallocation in the pre-/metastatic tumour microenvironments by suppressing glucose utilization in normal niche cells and allowing for more glucose to be available to cancer cells, thereby facilitating metastatic cancer growth. This effect is at least partially mediated by cancer-secreted miR-122.

MiR-122 and PKM2 Levels are Inversely Correlated in Primary Breast Tumours

Figure 29A:
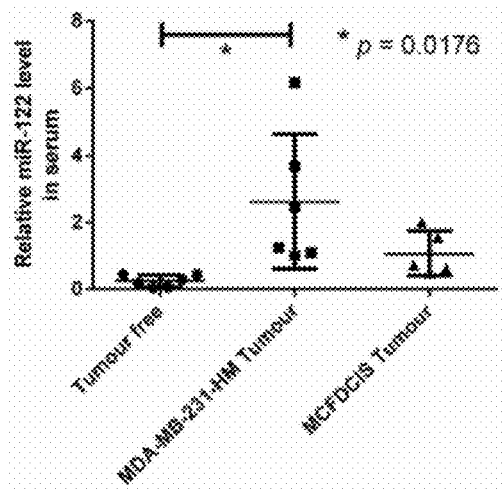
Figure 29B:
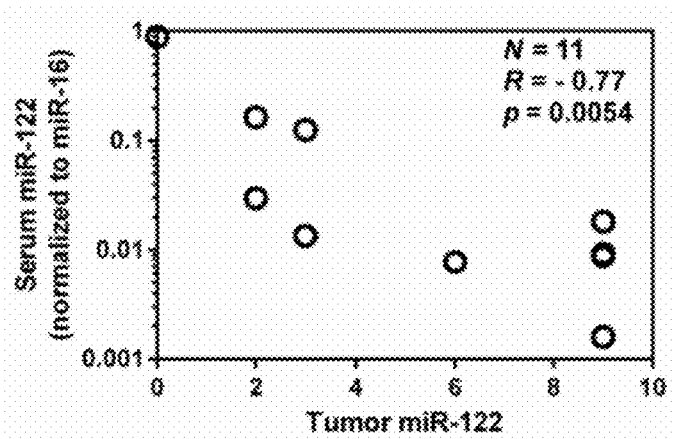

It is demonstrated herein that circulating miR-122 is a marker for predicting metastatic progression in early-stage BC patients. Using an orthotopic xenograft model comparing highly metastatic MDA-MB-231-HM tumours and poorly metastatic MCFDCIS tumours to tumour-free mice at an early, non-metastatic stage, it was found that serum miR-122 levels were significantly higher in mice bearing MDA-MB-231-HM tumours (FIG. 29A). It was then examined whether there was a correlation between the tumour and serum levels of miR-122 in BC patients. Correlation analysis showed a Spearman's coefficient of $-0.77$ (N=11, p=0.0054), demonstrating a strong inverse correlation (FIG. 29B). By fractioning pooled normal or patient serum into an exosome-rich fraction and an exosome-depleted fraction, it was found that miR-122 was significantly enriched in the exosome fraction and was higher in the circulating exosomes from cancer patients (FIG. 29C). In addition, tumour sections were stained for PKM2 to explore the correlation between miR-122 and PKM2 in primary BCs (FIG. 29E). Pearson's coefficient between miR-122 and PKM2 pathology scores was $-0.40$ (N=70, p<0.001), demonstrating a significant inverse correlation (FIG. 29D). These data with clinical specimens further support that PKM2 is a target of miR-122. Taken together, our results suggest that cancer cells may secrete miR-122 as a dual function to reduce intracellular miR-122 in order to maintain high glucose metabolism in cancer cells while simultaneously suppressing glucose uptake by niche cells.

Discussion

This example demonstrates that miR-122 is expressed and highly secreted by BC cells, and therefore provides an understanding of our observation that miR-122 is found in BC patients' blood and its level is correlated to disease progression. Through exosomal transfer, cancer-derived miR-122 can enter and suppress glucose utilization in recipient niche cells including fibroblasts and astrocytes at a distant site. This effect is primarily mediated by down-regulation of PKM. The human PKM gene encodes two isozymes through alternative splicing and both isoforms carry the miR-122-binding site identified herein (FIGS. 24D and 24E). PKM1 is expressed in tissues with limited cell proliferation such as muscle, heart, and brain, whereas PKM2 is the major isoform in proliferative cells such as embryonic tissues and most cancer cells (Mazurek, Int. J. Biochem. Cell Biol., 43:969-980 (2011)). The cell models used in this study all expressed PKM2 as determined at the RNA level (FIG. 31A). PKM2 is also the major isoform in mouse lung tissue, whereas in mouse brain tissue, the M1 isoform is preferentially expressed (FIG. 31B). Down-regulation of brain and lung PKM in tumour-bearing mice and its alleviation by anti-miR-122 treatment were confirmed at the RNA level (FIGS. 28H and 28I), indicating that miR-122 targets both PKM1 and PKM2 to affect a variety of tissues.

PKM2 has been demonstrated to act as a switch for the Warburg effect in cancer cells as its replacement with PKM1 leads to decreased aerobic glycolysis, increased oxygen consumption, and suppressed tumour growth45. Here it is shown that PKM2 down-regulation by miR-122 resulted in decreased expression of GLUT1 at RNA and protein levels in multiple cell types (FIGS. 24-28 and FIGS. 32-33), which suggests that miR-122 regulates glucose uptake through the PKM2-GLUT1 axis. This feedback mechanism to adjust glucose flux into the cells through the reduction of PKM activity and glycolytic rate by miR-122 partially constitutes the cancer-derived glucose reallocation between cancer and niche cells. The simultaneous downregulation of CS by miR-122, which likely leads to a reduced rate of TCA cycling, may further contribute to the coordinated cellular rates of glucose flux, glycolysis, and oxidative phosphorylation to avoid rapid depletion or build-up of intermediates in glucose metabolism. Consistent with this notion, significantly reduced glucose and lactate was observed but little or no difference in most of the TCA cycle intermediates in MCF10A with high miR-122 (FIG. 24B).

Adaptation of a local or distant tumour microenvironment has been recognized as an important means for cancer cells to facilitate their sustained growth and metastasis. Previous work has highlighted the importance of exosomes in facilitating pre-metastatic niche metastasis (Peinado, et al., Nat. Med., 18:883-891 (2012); Grange et al., Cancer Res., 71:5346-5356 (2011); and Hood et al., Cancer Res., 71:3792-3801 (2011)), while other have demonstrated the importance of secreted-factors to enhance angiogenesis within the tumor microenvironment (Maione et al., J. Clin. Invest., 122:1832-1848 (2012); Caner, et al., Cancer Res., 72:6371-6381 (2012); Hiratsuka et al., Nature Communications, 4:1853 (2013); Chang et al., Neoplasia, 15:848-862 (2013)). Herein is shown a unique aspect of nutrient utilization to this paradigm of cancer-host crosstalk. Enhanced glucose uptake is common in cancer as a result of the high energy demand in cancer cells and the low ATP generating efficiency of the Warburg effect. GLUT1 and glycolytic enzymes such as HK have been shown to be up-regulated in BC (Bos et al., J. Clin., Oncol., 20:379-387 (2002); Kang, et al., Jpn. J. Cancer Res., 93:1123-1128 (2002)) as potential mechanisms for increasing glucose uptake. In addition to this enhanced ability, cancer cells also develop strategies to increase their availability to glucose in the niche, such as angiogenesis to gain nutrients from the blood46, 47. Herein is provided the first evidence that cancer cells are not only capable of enhancing their own glucose uptake but also globally suppressing the nutrient utilization by other cell types. This miR-122-mediated mechanism may be more important at an early stage prior to cancer-induced angiogenesis, when the availability of nutrients in the tumour microenvironment become limited to sustain tumour growth, and when disseminated tumour cells arrive to a distant tissue to prepare for colonization and rapid expansion among the surrounding normal niche cells which are native competitors for nutrients. Indeed, it was observed that BC cells at the primary site (mammary gland) were able to affect glucose uptake by brain and lung at a pre-met stage (FIGS. 28E and 28G) through exosomal secretion of miR-122. Elevated level of miR-122 can also be detected in the circulation at this stage in the animal model (FIG. 29A) and in BC patients, heralding the occurrence of metastasis. Importantly, miR-122 intervention using antisense oligos significantly reduced BC metastasis to brain and lung (FIGS. 28C and 28D). Thus, the studies and examples herein indicate that cancer-derived circulating miR-122 is both a predictive marker and therapeutic target for metastatic BC. As miR-122 antagonists are currently in clinical trials for patients with hepatitis C infection and exhibit good tolerance with a low propensity for drug interactions (Elmen, et al., Nucleic Acids Res., 36:1153-1162 (2008); Elmen, et al., Nature, 452:896-899 (2008)), miR-122-targeted therapy in cancer patients seems highly feasible, while the non-invasive blood test for circulating miR-122 would enable accurate selection of patients who may benefit from this treatment.

Methods

Cells, Plasmids, and Viruses

Human cancer cell lines and the non-cancerous cell line MCF10A were obtained from American Type Culture Collection (Manassas, Va.) and cultured in the recommended media. Mouse astrocytes were purchased from Lonza and cultured following the manufacturer's instructions. MCF10DCIS.com (MCFDCIS) cells were purchased from Asterand (Detroit, Mich.). The MDAMB-231-HM cells were generated in the lab through explant culture of a spontaneous meningeal metastasis of MDA-MB-231 cells from an immunocompromised mouse. Mouse lung fibroblasts were isolated from minced lung tissue grown in DMEM supplemented with 10% FBS and 10 µg/ml bFGF (Life Technologies, Carlsbad, Calif.). Purity of the fibroblasts was confirmed by the expression of fibroblast specific protein 1 (FSP-1) in >95% of the cells (FIG. 34). All cells used herein were tested to be free of mycoplasma contamination. To construct the PKM and CS 3'UTR reporter plasmids, annealed oligonucleotides encompassing the wild-type or mutated miR-122 binding sites indicated in FIG. 24A were inserted into the XhoI/NotI sites of psiCHECK-2 vector (Promega; Madison, Wis.) downstream of the Renilla luciferase gene. For miR-122 over expression, the hsa-mir-122 gene was cloned by PCR using primers 5'-GCAGCT-GAATTCGAGCTGACAAGGTTCCCCTA (SEQ ID NO:11) and 5'-TAGTACGTCGACAAAGCAAACGATGC-CAAGAC (SEQ ID NO:12), and ligated into the EcoRI/SalI sites of pBABE-Puro or pBABE-GFP retroviral vector. PKM2 and CS over expressing vectors were constructed by PCR cloning the full-length cDNA of PKM2 or CS using primers 5'-GAAGTTGGATCCAGATCAGGACCTCA-GCA (SEQ ID NO:13) and 5'-GAAGTTGAATTCG-GCTCTGGGGTCCATCAC (SEQ ID NO:14) for PKM2 or 5'-GAAGT4TGGATCCTTACCTCCCCACCAGATCC (SEQ ID NO:15) and 5'-GAAGTTGAATTCACTTTCAC-CCAGTCTCCA (SEQ ID NO:16) for CS from MCF10A cells, and inserting the cDNA fragment into the BamHI/EcoRI sites of pBABE-Puro. All constructs were verified by sequencing. Cell transfection, reporter assays, production of viruses, as well as infection and selection of transduced cells were carried out as previously described (Wang et al., Oncogene, 30:1470-1480 (2011)).

Exosome Purification

Conditioned media (CM) was collected from cells grown in exosome-depleted media (prepared by overnight ultracentrifugation at 156,000 g at 4° C.) for 48 hours. Dead cells and contaminating cell debris were removed by centrifugation at 500 g for 15 min and then at 10,000 g for 20 min at 4° C. Media was then subjected to ultracentrifugation at 110,000 g for 70 min at 4° C. to pellet exosomes. Exosomes were washed with PBS and subjected to an additional round of ultracentrifugation. When indicated, exosomes were incubated in 1 µM 1,1'-dioctadecyl-3,3,3'3'-tetramethylindocarbocyanine perchlorate (DiI) for 20 min in PBS, followed by an additional round of PBS wash. PBS was then used to resuspend exosomes to feed to target cells.

2-NBDG Uptake Assay

After 96 hours post-exosome treatment, recipient cells were labelled with 100 µM 2-NBDG diluted in glucose-free media and incubated for 40 min at 37° C. Fluorescence quantification was performed using a SpectraMax M3 (Molecular Devices; Sunnyvale, Calif.) fluorometer at em 465/ex 540 nm. Values were normalized to protein content.

RNA Extraction and Reverse Transcription (RT) Real-Time qPCR

These procedures were performed as described previously (Tsuyada et al., Cancer Res., 72:2768-2779 (2012); Yu et al., Mol. Cancer Res., 8:1633-1642 (2010)). Primers used in RT-qPCR are indicated in Tables 4 and 5.

TABLE 4

RT-q-PCR primer sequences for human genes.

| Gene | Forward primer | Reverse primer | Isoform |
|---|---|---|---|
| PKM | ATTATTTGAGGAACTCCGCCG CCT (SEQ ID NO: 17) | ATTCCGGGTCACAGCAATGA TGG (SEQ ID NO: 18) | M2 |
| CS | GGTGGCATGAGAGGCATGAA (SEQ ID NO: 19) | TAGCCTTGGGTAGCAGTTTCT (SEQ ID NO: 20) | |
| GLUT1 (SLC2A1) | GGCCAAGAGTGTGCTAAAGA A (SEQ ID NO: 21) | ACAGCGTTGATGCCAGACAG (SEQ ID NO: 22) | |
| GLUT3 (SLC2A3) | GCTGGGCATCGTTGTTGGA (SEQ ID NO: 23) | GCACTTTGTAGGATAGCAGG AAG (SEQ ID NO: 24) | |
| GLUT4 (SLC2A4) | CTGTGCCATCCTGATGACTG (SEQ ID NO: 25) | CGTAGCTCATGGCTGGAACT (SEQ ID NO: 26) | |
| GPI | CCGCGTCTGGTATGTCTCC (SEQ ID NO: 27) | CCTGGGTAGTAAAGGTCTTG GA (SEQ ID NO: 28) | |
| HK2 | AACCATGACCAAGTGCAGAA (SEQ ID NO: 29) | AGCCCTTTCTCCATCTCCTT (SEQ ID NO: 30) | |
| 18S rRNA | CTACCACATCCAAGGAAGGC A (SEQ ID NO: 31) | TTTTTCGTCACTACCTCCCCG (SEQ ID NO: 32) | |

TABLE 5

RT-qPCR primer sequences for mouse genes.

| Gene | Forward primer | Reverse primer | Isoform |
|---|---|---|---|
| Pkm | GCAGGAACCGAAGTACGC (SEQ ID NO: 33) | TGTGTTCCAGGAAGGTGTCA (SEQ ID NO: 34) | M1, M2 |
| Cs | AGGCTAGACTGGTCACACA AT (SEQ ID NO: 35) | AGGACAGGTAAGGGTCTGAAA G (SEQ ID NO: 36) | |
| Glut1 (Slc2a1) | GGGCCTAAGGTCACATGAA G (SEQ ID NO: 37) | CCAGTGTTATAGCCGAACTG (SEQ ID NO: 38) | |
| 18S rRNA | CGCTTCCTTACCTGGTTGAT (SEQ ID NO: 39) | GAGCGACCAAAGGAACCATA (SEQ ID NO: 40) | |
| B-actin | CGAGGCCCAGAGCAAGAGA G (SEQ ID NO: 41) | CGGTTGGCCTTAGGGTTCAG (SEQ ID NO: 42) | |

The miR-122, miR-16 (as internal control for exosomal and circulating miR-122) and U6 primers (as internal control for intracellular miR-122) were purchased from Qiagen (Valencia, Calif.).

Western Blot Analysis and PKM Activity Assay

PKM2 antibody (C-11) was purchased from Santa Cruz Biotechnology (Santa Cruz, Calif.), CS antibody (Cat #16131-1-AP) from Proteintech Group (Chicago, Ill.), and GLUT1 antibody (Cat # ab652) from AbCam (Cambridge, Mass.). β-actin antibody (AC-15) was purchased from Sigma-Aldrich (St. Louis, Mo.). PKM activity was assessed using a protocol modified from Edwards and Watts60 by diluting each protein sample in 228 µl Solution A (110 mmol/L Imidazole-HCl, 165 mmol/L KCl, 5.5 mmol/L MgCl2, 0.19 mmol/L NADH, 5.5 mmol/L ADP, 5.5 mmol/L DTT, pH 7.4) supplemented with 2.5 unit lactate dehydrogenase and 62.5 nmol phosphoenolpyruvate (Sigma-Aldrich). Decreases in absorbance of NADH at 340 nm were followed every minute for 10 min after initiation of the reaction. One unit of PKM activity was defined as the amount that will consume 1 µmol of NADH (molar absorptivity 6.22 cm2/µmol) per minute under the assay condition.

Medium Metabolite Analysis

MCF10A-derived cells seeded at equal number were cultured in growth media containing 3 g/L glucose but no pyruvate for 72 hours before CM was collected, cleared by centrifugation, and subjected to metabolite measurement using a BioProfile 100 Plus (Nova Biomedical; Waltham, Mass.). Media collected from cell-free plates after 72 h incubation was used as the baseline control to calculate the consumption or production of each metabolite, which was further normalized to the cell number in each plate determined at the time of CM collection.

Cell Metabolome Analysis by NMR Spectroscopy

Sample preparation, NMR spectroscopy, and data analyses were performed as described (Cano et al., J. Proteome Res., 9:5382-5388 (2010)). Hydrophilic metabolites dried from the methanol-water fractions were resuspended in 500 L 100% $D_2O$ containing 3.2 M of 4,4-dimethyl-4-silapentane-1-sulfonic acid (DSS), which serves as an internal chemical shift reference and a concentration standard. 1D NMR spectra were acquired at 25 C on a Bruker Avance spectrometer equipped with a cryoprobe operating at 600.19

MHz 1H frequency. Pre-saturation was used to suppress water signal, and the spectra was collected with spectral width of 10 kHz, 32 k data points, 3 s relaxation delay and 1024 transients. $^1$H NMR spectra of the samples were processed using the Chenomx NMR Suite Processor (version 7.5, Chenomx Inc., Edmonton, Canada), and the metabolites were identified and quantified using the Chenomx NMR Suite Profiler. Standard deviation was calculated from triplicate samples.

Animal Models: Exosome Conditioning and Xenografts

All animal procedures were approved by the Institutional Animal Care and Use Committee at City of Hope and in compliance with ethical regulations. Female NOD/SCID/IL2Rγ-null (NSG) mice of 6-8 week old were used in this study. Exosomes were isolated from MCF10A/vec, MCF10A/miR-122, and MDA-MB-231 (~6 μg/mouse) by the above procedure and followed by centrifugation at 14,000 rpm for 10 min at 4° C. Exosomes were then injected into the tail vein of NSG mice biweekly for 3.5 weeks. Orthotopic xenografts were established in NSG mice injected with 2 105 luciferase-labelled MDA-MB-231-HM cells combined with Matrigel (BD Biosciences; San Jose, Calif.) in a 1:1 ratio into the No. 4 mammary fat pad. Weekly bioluminescence imaging (BLI) was carried out using a Xenogen system (Caliper Life Sciences; Alameda, Calif.). Tumour volume was assessed by caliper measurements using the formula (width2×length)/2 (mm3). For the miR-122 intervention study, mice were divided into 3 groups for treatment with PBS, anti-miR-122 oligos (sequence: 5'-CcAttGTcaCaCtCC (SEQ ID NO:4); 2'-deoxy-2'-fluoro-RNA in capitals, DNA in lower case) or mismatch control oligos (5'-CcAttCTcaCaCtGC (SEQ ID NO:43)) with a phosphorothioate backbone synthesized at the City of Hope Core of Synthetic and Biopolymer Chemistry. Starting from day 3 after cancer cell transplantation, oligos (25 mg/kg) were intraperitoneally (i.p.) injected daily for 5 days and then twice weekly until the end of experiment. For 2-NBDG uptake, 15 mg/kg of 2-NBDG was injected through the tail vein 45 min before a transcardiac perfusion with 1% PFA in PBS was carried out to remove the excess dye. Tissues were formaldehyde-fixed and paraffin-embedded or embedded in Tissue-Tek O.C.T. Compound (Sakura; Torrance, Calif.) to make frozen blocks for sectioning and 2-NBDG analysis by fluorescence microscopy. The 2-NBDG signals were quantified using ImagePro 6.3 software (Media Cybernetics; Rockville, Md.). For serum miRNA analysis, blood was collected through cardiac puncture and fractionated by centrifugation, and serum RNA was extracted using Trizol LS (Life Technologies).

Co-Immunofluorescence (IF)

O.C.T. sections were fixed with 4% PFA in PBS, blocked and permeabilised with PBS containing 10% goat serum and 0.05% saponin, prior to incubation with rabbit anti-mouse GFAP (AbCam; Cat # ab7260) for brain or rabbit anti-mouse FSP-1 (AbCam; Cat # ab27957) for lung together with mouse anti-human CD63 (MEM-259; Novus Biologicals; Littleton, Colo.). Primary antibodies were then visualised with goat anti-rabbit Alexa 488 and goat anti-rabbit Alexa 594 (Life Technologies; Grand Island, N.Y.). Images were obtained by fluorescence microscopy then pseudo-coloured and merged using ImagePro 6.3 software (Media Cybernetics; Rockville, Md.).

Immunohistochemistry (IHC)

IHC was performed as previously described (Fong et al., PLoS One, 7:e42265 (2010)) using a 1:400 antibody dilution for PKM2 (C-11) and 1:250 dilution for GLUT1 (AbCam; Cat # ab652). ISH was performed as described (Jorgensen, et al., Methods, 52:375-381 (2010)) using LNA™ microRNA ISH miR-122 optimization kit (Exiqon; Woburn, Mass.) and developed with NBT:BCIP (Vector Laboratories; Burlingame, Calif.) at 30° C. overnight.

Glycogen Staining

Glycogen staining was performed using a Periodic Acid-Schiff (PAS) kit (Sigma-Aldrich, St. Louis, Mo.) following the manufacturer's protocol.

Clinical Specimens

Human BC tissues were obtained from a BC array (US Biomax; Cat # BR1505a; Rockville, Md.). For gene expression analysis using tumour tissues (N=70), FFPE slides stained for miR-122 and PKM2 were scored according to intensity of staining (−: 0; +: 1; ++: 2; and +++: 3) and percentage of tumour cells staining positive for each antigen (0%: 0; 1~29%: 1; 30~69%: 2; and ≥70%: 3). The score for the intensity was multiplied by the score for the percentage of cells staining positive to obtain a final score, which was used in the statistical correlation analysis. Human specimens used in the serum-tumour correlation analysis (N=11) were obtained from voluntarily consenting patients at the City of Hope Medical Center (Duarte, Calif.) under Institutional Review Board-approved protocols. Informed consent was obtained from all subjects. Serum RNA was extracted using Trizol LS and subjected to RT-qPCR using primers for miR-122 and miR-16 as described (Wu, et al., J. Transl. Med., 10:42 (2012)). The clinical characteristics of the patients are described in Table 4.

TABLE 4

Clinical characteristics of patients in the serum-tumour correlation study.

| Parameter | Cohort for serum-tumor correlation N (%) |
| --- | --- |
| Patients (N) | 11 (100) |
| Age (Mean ± SD) | 53 ± 10 |
| ER+ | 7 (64) |
| ER− | 4 (36) |
| PR+ | 3 (27) |
| PR− | 8 (73) |
| HER2+ | 3 (27) |
| HER2− | 8 (73) |
| Stage II | 4 (36) |
| Stage III | 7 (64) |

Values in each column indicate the number of patients with percentage of the cohort in parenthesis.

Statistical Analyses

All results were confirmed in at least three independent experiments, and data from one representative experiment was shown. All quantitative data are presented as mean±standard deviation. For all quantitative data, statistical analyses were performed using GraphPad software. ANOVA testing was used for comparison of quantitative data followed by Student-Newman-Keuls post-test. The linear dependence between miR-122 and PKM2 expression and between serum and tumour miR-122 was evaluated by Pearson and Spearman correlation coefficients, respectively. Values of p<0.05 were considered significant. Sample size was generally chosen based on preliminary data indicating the variance within each group and the differences between groups. For the animal study in FIG. 28, sample size was predetermined to allow an 80% power to detect a difference of 50%. All samples/animals that have received the proper procedures with confidence were included for the analyses. Animals were randomized before treatments in FIGS. 27 and 28. For animal studies, the investigators were blinded to allocation during outcome assessment. For data in FIG. 29, the investigators were blinded to allocation during experiments and outcome assessment. For every figure, statistical tests are justified as appropriate, and the data meet the assumptions of the tests. The variance within each group of data is similar between groups that are being statistically compared.

What is claimed is:

1. A method of measuring a level of miR-105 in a subject that has a breast cancer, the method comprising the steps of:
   (a) obtaining a serum-derived biological sample from the subject that has the breast cancer;
   (b) measuring a level of miR-105 in the serum-derived biological sample, wherein the measuring comprises performing a nucleic acid hybridization;
   (c) detecting an increased level of miR-105 in said serum-derived biological sample compared to a control; and
   (d) administering to said subject an antisense oligonucleotide inhibitor of miR-105.

2. The method of claim 1, wherein the breast cancer is metastatic breast cancer.

3. The method of claim 1, wherein performing a nucleic acid hybridization comprises performing a Northern Blot, RT-PCR, microarray analysis, or sequencing.

4. The method of claim 1, wherein performing a nucleic acid hybridization comprises contacting the biological sample with a probe capable of binding to miR-105 and detecting binding of the one or more probes to the miR-105.

5. The method of claim 4, wherein the probe is a labeled probe.

6. The method of claim 4, wherein the probe is complementary to at least 10 nucleic acid residues of miR-105.

7. The method of claim 6, wherein the probe is fully complementary to said nucleic acid residues of miR-105.

8. The method of claim 6, wherein the 10 nucleic acid residues are contiguous.

9. The method of claim 1, wherein the miR-105 comprises SEQ ID NO:1.

10. The method of claim 1, wherein the miR-105 comprises the mature form of miR-105.

11. The method of claim 1, wherein the breast cancer is a primary breast cancer.

12. A method of measuring a level of miR-105 in a subject that has a breast cancer, the method comprising the steps of:
   (a) obtaining a serum-derived biological sample from the subject that has the breast cancer;
   (b) measuring a level of miR-105 in the serum-derived biological sample, wherein the measuring comprises performing a nucleic acid hybridization
   (c) detecting an increased level of miR-105 in said serum-derived biological sample compared to a control; and
   (d) administering to said subject a cancer therapeutic agent selected from the group consisting of: an aromatase inhibitor, a HER2 antibody, cyclophosphamide, doxorubicin, docetaxel, methotrexate, 5-fluorouracil, trastuzumab, and tamoxifen.

13. The method of claim 12, wherein the breast cancer is metastatic breast cancer.

14. The method of claim 12, wherein performing a nucleic acid hybridization comprises performing a Northern Blot, RT-PCR, microarray analysis, or sequencing.

15. The method of claim 12, wherein performing a nucleic acid hybridization comprises contacting the biological sample with a probe capable of binding to miR-105 and detecting binding of the one or more probes to the miR-105.

16. The method of claim 15, wherein the probe is a labeled probe.

17. The method of claim 15, wherein the probe is complementary to at least 10 nucleic acid residues of miR-105.

18. The method of claim 17, wherein the probe is fully complementary to said nucleic acid residues of miR-105.

19. The method of claim 17, wherein the 10 nucleic acid residues are contiguous.

20. The method of claim 12, wherein the miR-105 comprises SEQ ID NO:1.

21. The method of claim 12, wherein the miR-105 comprises the mature form of miR-105.

22. The method of claim 12, wherein the breast cancer is a primary breast cancer.

23. A method of measuring a level of miR-105 in a subject that has a breast cancer, the method comprising the steps of:
   (a) obtaining a serum-derived biological sample from the subject that has the breast cancer;
   (b) measuring a level of miR-105 in the serum-derived biological sample, wherein the measuring comprises performing a nucleic acid hybridization
   (c) detecting an increased level of miR-105 in said serum-derived biological sample compared to a control; and
   (d) administering to said subject an antisense oligonucleotide inhibitor of miR-122.

24. The method of claim 23, wherein the breast cancer is metastatic breast cancer.

25. The method of claim 23, wherein performing a nucleic acid hybridization comprises performing a Northern Blot, RT-PCR, microarray analysis, or sequencing.

26. The method of claim 23, wherein performing a nucleic acid hybridization comprises contacting the biological sample with a probe capable of binding to miR-105 and detecting binding of the one or more probes to the miR-105.

27. The method of claim 26, wherein the probe is a labeled probe.

28. The method of claim 26, wherein the probe is complementary to at least 10 nucleic acid residues of miR-105.

29. The method of claim 28, wherein the probe is fully complementary to said nucleic acid residues of miR-105.

30. The method of claim 28, wherein the 10 nucleic acid residues are contiguous.

31. The method of claim 23, wherein the miR-105 comprises SEQ ID NO:1.

32. The method of claim 23, wherein the miR-105 comprises the mature form of miR-105.

33. The method of claim 23, wherein the breast cancer is a primary breast cancer.

* * * * *

UNITED STATES PATENT AND TRADEMARK OFFICE
CERTIFICATE OF CORRECTION

PATENT NO. : 10,793,913 B2
APPLICATION NO. : 14/203173
DATED : October 6, 2020
INVENTOR(S) : Shizhen Emily Wang and Xiwei Wu Page 1 of 1

It is certified that error appears in the above-identified patent and that said Letters Patent is hereby corrected as shown below:

In the Specification

Column 1, Lines 16-18, delete the following sentence: "The present was supported at least in part by government funding from the National Institutes of Health, Grant No. R01CA166020, R01CA163586 and P30CA33572." and insert the following sentence: --This invention was made with government support under R01 CA166020, R01 CA163586, and P30 CA033572 awarded by the National Institutes of Health.--

Signed and Sealed this
Seventh Day of January, 2025

Derrick Brent
*Acting Director of the United States Patent and Trademark Office*